US008163506B2

(12) United States Patent
Saito et al.

(10) Patent No.: US 8,163,506 B2
(45) Date of Patent: Apr. 24, 2012

(54) USE OF TOLL-LIKE RECEPTOR-EXPRESSING CELLS

(75) Inventors: Tadao Saito, Miyagi (JP); Takeshi Shimosato, Miyagi (JP); Haruki Kitazawa, Miyagi (JP)

(73) Assignee: Meiji Co., Ltd., Tokyo (JP)

( * ) Notice: Subject to any disclaimer, the term of this patent is extended or adjusted under 35 U.S.C. 154(b) by 820 days.

(21) Appl. No.: 10/561,022

(22) PCT Filed: Mar. 5, 2004

(86) PCT No.: PCT/JP2004/002920
§ 371 (c)(1),
(2), (4) Date: Mar. 8, 2007

(87) PCT Pub. No.: WO2005/001116
PCT Pub. Date: Jan. 6, 2005

(65) Prior Publication Data
US 2007/0298449 A1 Dec. 27, 2007

(30) Foreign Application Priority Data
Jun. 17, 2003 (JP) ................................. 2003-172132

(51) Int. Cl.
G01N 33/567 (2006.01)
C12N 15/117 (2010.01)
C07K 14/705 (2006.01)

(52) U.S. Cl. ....... 435/7.21; 514/885; 530/350; 530/837; 530/844

(58) Field of Classification Search ........................ None
See application file for complete search history.

(56) References Cited

U.S. PATENT DOCUMENTS
2003/0124655 A1 7/2003 Akira et al.

FOREIGN PATENT DOCUMENTS
| | | |
|---|---|---|
| EP | 1 302 541 A1 | 4/2003 |
| JP | 2002-034565 A | 2/2002 |
| JP | 2002-526028 | 8/2002 |
| WO | WO 99/20756 A | 4/1999 |
| WO | WO 02/06482 A1 | 1/2002 |
| WO | WO 03/031573 A2 | 4/2003 |
| WO | WO 2004026888 A2 * | 4/2004 |

OTHER PUBLICATIONS

Ichikawa et al, 2007. Biosci Biotechnol Biochem. 71(12): 3026-3032.*
Fukata et al, 2008. Oncogene. 27: 234-243.*
Wang et al (Nuc. Acids Res. 27: 4609-4618, 1999; p. 4617).*
Kaufman et al (Blood 94: 3178-3184, 1999).*
Zarember et al, 2002. The Journal of Immunology. 168: 554-561.*
Shimosato et al (2003. Biochimica et Biophysica Acta et al. 1627: 56-61).*
Kitazawa et al (2003. International Journal of Food Microbiology. 85(1-2):11-21; published Aug. 15, 2003 but available one Nov. 16, 2002; 17 pages as printed.*
Duval-Iflah et al, 1998. Antonie van Leeuwenhoek. 73: 95-102.*
Wells (1990) Biochemistry 29(37): 8509-8517.*
Ngo et al (1994) "The Protein Folding Problem and Tertiary Structure Prediction, Chapter 14: Computational Complexity Protein Structure Prediction, and the Levinthal Paradox" pp. 433-440 and 492-495 only.*
Bork (2000) Genome Research 10:398.*
Skolnick et al (2000) Trends in Biotech. 18(1): 34.*
Doerks et al (1998) Trends in Genetics 14(6): 248.*
Brenner (1999) Trends in Genetics 15(4): 132.*
Wells et al, 2009 (International Journal of Medical Microbiology. 8 pages).*
Shimosato et al, 2004. Animal Science Journal, 75: 377-382.*
ScienceDirect abstract for Shimosato et al; available atl http://www.sciencedirect.com/science/article/pii/S0167478103000484; 1 page as printed; printed on Sep. 1, 2011.*
Bauer, M. et al., "Bacterial CpG-DNA Triggers Activation and Maturation of Human CD11c⁻, CD123⁺ Dendritic Cell," *The Journal of Immunology*, 2001, pp. 5000-5007, vol. 166.
Hemmi, H. et al., "A Toll-like receptor recognizes bacterial DNA," *Nature*, 2000, pp. 740-745, vol. 408, No. 6813.
Imaeda, H. et al., "In vivo response of neutrophils and epithelial cells to lipopolysaccharide injected into the monkey ileum," *Histochem. Cell Biol.*, 2002, pp. 381-388, vol. 118, No. 5.
Kitazawa, H. et al. "Cloning sTLR1 and 6 that interact with swine Toll-like receptor (sTLR)2 and their expression analysis," *The Annual Meeting of the Japan Society for Bioscience, Biotechnology, and Agrochemistry*, Apr. 2003, 2A04a07, vol. 1.
Klinman, D.M. et al. "CpG DNA: recognition by and activation of monocytes," *Microbes and Infection*, 2002, pp. 897-901, vol. 4.
Shimosato, T. et al. "Cloning Swine Toll-like receptor (sTLR)2 and its expression analysis," *The Annual Meeting of the Japan Society for Bioscience, Biotechnology, and Agrochemistry*, Apr. 2003, 2A04a06, vol. 1.
Takeshita, F. et al., "Role of Toll-Like Receptor 9 in CpG DNA-Induced Activation of Human Cells," *The Journal of Immunology*, 2001, pp. 3555-3558, vol. 167.

(Continued)

*Primary Examiner* — Bridget E Bunner
*Assistant Examiner* — Zachary Howard
(74) *Attorney, Agent, or Firm* — Saliwanchik, Lloyd & Eisenschenk

(57) ABSTRACT

Swine Toll-like receptor 9 (TLR9)-expressing cells are prepared by cloning a TLR9 gene from swine intestinal Peyer's patches. Functional analysis on CpG DNAs using the above cells revealed that swine TLR9 shows a higher recognition ability for a human CpG DNA motif (CpG2006) than for a mouse-specific CpG DNA motif (CpG1826). When the mRNA expression levels in various tissues are compared by the real-time PCR method, it is found out that the mRNA is expressed in Peyer's patches and mesenteric lymph nodes, which play important roles in the intestinal tract immune system, at a level thrice as much as in spleen or more. Thus, the cells expressing an intestinal tract tissue-expressed TLR (for example, TLR9) can be used to identify samples capable of activating the intestinal tract immune system.

6 Claims, 13 Drawing Sheets

OTHER PUBLICATIONS

Takeuchi, O. et al. "Toll-like receptors; their physiological role and signal transduction system," *International Immunopharmacology*, 2001, pp. 625-635, vol. 1.

Yoshimura, A. et al. "Structural requirements of muramylpeptides for induction of Toll-like receptor 2-mediated NF-κb activation in CHO cells,125" *J. Endotoxin Res.*, 2000, pp. 407-410, vol. 6, No. 5.

Tohno et al. "A swine toll-like receptor 2-expressing transfectanr as a potential primary screening system for immunobiotic microorganisms" *FEMS Immunology and Medical Microbiology*, 2005, pp. 283-288, vol. 44.

Tohno et al. "Toll-like receptor 2 and 9 are expressed and functional in gut-associated lymphoid tissues of presuckling newborn swine" *Vet. Res.*, 2006, pp. 791-812, vol. 37.

Database GenBank Accession No. AB071394, "Sus scrofa TLR9 mRNA for Toll-like receptor 9, complete cds," May 21, 2003.

Database GenBank Accession No. AY392087, "Sus scrofa toll-like receptor 2 mRNA, complete cds," Nov. 1, 2003.

Chabot, S., et al., "TLRs Regulate the Gatekeeping Functions of the Intestinal Follicle-Associate Epithelium," *J Immunol*, Apr. 1, 2006, pp. 4275-4283, vol. 176, No. 7.

Kitazawa, H., et al., "Discovery of immunostimulatory DNA motifs from lactic acid bacteria and their application to 'Bio-Defense Foods'," *Journal of the agricultural chemical society of Japan*, 2002, pp. 833-836, vol. 76, No. 9.

Shimosato, T., et al., "Toll-like receptor 9 is expressed on follicle-associated epithelia containing M cells in swine Peyer's patches," *Immunol Lett.*, Apr. 15, 2005, pp. 83-89, vol. 98, No. 1.

Shinkai, H., et al., "Biased distribution of single nucleotide polymorphisms (SNPs) in porcine Toll-like receptor 1 (*TLR1*), *TLR2, TLR4, TLR5*, and *TLR6* genes," *Immunogenetics*, May 2006, pp. 324-330, vol. 58, No. 4.

Tohno, M., et al., "Toll-like receptor 2 is expressed on the intestinal M cells in swine," *Biochem Biophys Res Commun.*, May 6, 2005, pp. 547-554, vol. 330, No. 2.

\* cited by examiner

FIG. 1

```
  -54 AGCTGCGGCCCGGTCTGCCAGCCAGACCCTTTGGAGAAGACCCCACTCCCTGTC
   1 ATGGGCCCCCGCTGCACCCTGCACCCCCTTTCTCTCCTGGTGCAGGTGACAGCGCTGGCT  60
     M   G   P   R   C   T   L   H   P   L   S   L   L   V   Q   V   T   A   L   A
  61 GCGACTCTGGCCCAGGGCAGGCTGCCTGCCTTCCTGCCCTGTGAGCTCCAGCCCCACGGC 120
     A   T   L   A   Q   G   R   L   P   A   F   L   P   C   E   L   Q   P   H   G
 121 CTGGTGAACTGCAACTGGCTCTTCCTGAAGTCCGTGCCCCACTTCTCGGCGGCAGCGCCC 180
     L   V   N   C   N   W   L   F   L   K   S   V   P   H   F   S   A   A   A   P
 181 CGGGCCAACGTCACCAGCCTCTCCTTACTCTCCAACCGCATCCACCACTTGCACGACTCT 240
     R   A   N   V   T   S   L   S   L   L   S   N   R   I   H   H   L   H   D   S
 241 GACTTCGTCCACCTGTCCAGCCTACGAACTCTCAACCTCAAGTGGAACTGCCCCGCCGGCT 300
     D   F   V   H   L   S   S   L   R   T   L   N   L   K   W   N   C   P   P   A
 301 GGCCTCAGCCCCATGCACTTCCCCTGCCACATGACCATCGAGCCCAACACCTTCCTGGCC 360
     G   L   S   P   M   H   F   P   C   H   M   T   I   E   P   N   T   F   L   A
 361 GTGCCCACCCTGGAGGAGCTGAACCTGAGCTACAACAGCATCACGACCGTGCCTGCCCTG 420
     V   P   T   L   E   E   L   N   L   S   Y   N   S   I   T   T   V   P   A   L
 421 CCCGACTCCCTCGTGTCCCTGTCGCTGAGCCGCACCAACATCCTGGTGCTAGACCCCACC 480
     P   D   S   L   V   S   L   S   L   S   R   T   N   I   L   V   L   D   P   T
 481 CACCTCACTGGCCTACATGCCCTGCGCTACCTGTACATGGATGGCAACTGCTACTACAAG 540
     H   L   T   G   L   H   A   L   R   Y   L   Y   M   D   G   N   C   Y   Y   K
 541 AACCCCTGCCAGGGGGCGCTGGAGGTGGTGCCGGGTGCCCTCCTCGGCCTGGGCAACCTC 600
     N   P   C   Q   G   A   L   E   V   V   P   G   A   L   L   G   L   G   N   L
 601 ACACATCTCTCACTCAAGTACAACAATCTCACGGAGGTGCCCCGCAGCCTGCCCCCCAGC 660
     T   H   L   S   L   K   Y   N   N   L   T   E   V   P   R   S   L   P   P   S
 661 CTGGAGACCCTGCTGTTGTCCTACAACCACATTGTCACCCTGACGCCTGAGGACCTGGCC 720
     L   E   T   L   L   L   S   Y   N   H   I   V   T   L   T   P   E   D   L   A
 721 AATCTGACTGCCCTGCGCGTGCTTGATGTGGGGGGGAACTGCCGCCGCTGTGACCATGCC 780
                                                          (SEQ ID NO:1 1-834)
     N   L   T   A   L   R   V   L   D   V   G   G   N   C   R   R   C   D   H   A
                                                          (SEQ ID NO:2 1-260)
```

FIG. 2

```
781 CGCAACCCCTGCAGGGAGTGCCCAAAGGACCACCCCAAGCTGCACTCTGACACCTTCAGC 840
    R  N  P  C  R  E  C  P  K  D  H  P  K  L  H  S  D  T  F  S
841 CACCTGAGCCGCCTCGAAGGCCTGGTGTTGAAAGACAGTTCTCTCTACAACCTGGACGCC 900
    H  L  S  R  L  E  G  L  V  L  K  D  S  S  L  Y  N  L  D  A
901 AGGTGGTTCCGAGGCCTGGACAGGCTCCAAGTGCTGGACCTGAGTGAGAACTTCCTCTAC 960
    R  W  F  R  G  L  D  R  L  Q  V  L  D  L  S  E  N  F  L  Y
961 GACTGCATCACCAAGACCACGGCCTTCCAGGGCCTGGCCCGACTgCGcAAGCTCAACCTG 1020
    D  C  I  T  K  T  T  A  F  Q  G  L  A  R  L  R  K  L  N  L
1021 TCCTTCAATTACCACAAGAAGGTGTCCTTTGCCCACCTGCACCTGGCACCCTCCTTTGGG 1080
    S  F  N  Y  H  K  K  V  S  F  A  H  L  H  L  A  P  S  F  G
1081 CACCTCCGGTCCCTGAAGGAGCTGGACATGCATGGCATCTTCTTCCGCTCGCTCAGTGAG 1140
    H  L  R  S  L  K  E  L  D  M  H  G  I  F  F  R  S  L  S  E
1141 ACCACGCTCCAACCTCTGGTCCAACTGCCTATGCTCCAGACCCTGCGCCTGCAGATGAAC 1200
    T  T  L  Q  P  L  V  Q  L  P  M  L  Q  T  L  R  L  Q  M  N
1201 TTCATTAACCAGGCCCAGCTCAGCATCTTTGGGGCCTTCCCTGGCCTGCTGTACGTGGAC 1260
    F  I  N  Q  A  Q  L  S  I  F  G  A  F  P  G  L  L  Y  V  D
1261 CTATCGGACAACCGCATCAGCGGAGCTGCAAGGCCAGTGGCCATTACTAGGGAGGTGGAT 1320
    L  S  D  N  R  I  S  G  A  A  R  P  V  A  I  T  R  E  V  D
1321 GGTAGGGAGAGGGTCTGGCTGCCTTCCAGGAACCTCGCTCCACGTCCACTGGACACTCTC 1380
    G  R  E  R  V  W  L  P  S  R  N  L  A  P  R  P  L  D  T  L
1381 CGCTCAGAGGACTTCATGCCAAACTGCAAGGCCTTCAGCTTCACCTTGGACCTGTCTCGG 1440
    R  S  E  D  F  M  P  N  C  K  A  F  S  F  T  L  D  L  S  R
1441 AACAACCTGGTGACAATCCAGTCGGAGATGTTTGCTCGCCTCTCACGCCTCGAGTGCCTG 1500
    N  N  L  V  T  I  Q  S  E  M  F  A  R  L  S  R  L  E  C  L
1501 CGTCTGAGCCACAACAGCATCTCCCAGGCGGTCAATGGCTCTCAGTTTGTGCCGCTGACC 1560
    R  L  S  H  N  S  I  S  Q  A  V  N  G  S  Q  F  V  P  L  T
```

(SEQ ID NO:1 835-1614)
(SEQ ID NO:2 261-520)

FIG. 3

```
1561 AGCCTGCGGGTGCTGGACCTGTCCCACAACAAGCTGGACCTGTATCACGGGCGCTCGTTC 1620
       S   L   R   V   L   D   L   S   H   N   K   L   D   L   Y   H   G   R   S   F
1621 ACGGAGCTGCCGCGCCTGGAAGCACTGGACCTCAGCTACAACAGCCAGCCCTTTACCATG 1680
       T   E   L   P   R   L   E   A   L   D   L   S   Y   N   S   Q   P   F   T   M
1681 CAGGGTGTGGGCCACAACCTCAGCTTCGTGGCCCAGCTGCCCGCCCTGCGCTACCTCAGC 1740
       Q   G   V   G   H   N   L   S   F   V   A   Q   L   P   A   L   R   Y   L   S
1741 CTGGCGCACAATGACATCCATAGCCGAGTGTCCCAGCAGCTCTGTAGCGCCTCACTGTGC 1800
       L   A   H   N   D   I   H   S   R   V   S   Q   Q   L   C   S   A   S   L   C
1801 GCCCTGGACTTTAGCGGCAACGATCTGAGCCGGATGTGGGCTGAGGGAGACCTCTATCTC 1860
       A   L   D   F   S   G   N   D   L   S   R   M   W   A   E   G   D   L   Y   L
1861 CGCTTCTTCCAAGGCCTAAGAAGCCTAGTCTGGCTGGACCTGTCCCAGAACCACCTGCAC 1920
       R   F   F   Q   G   L   R   S   L   V   W   L   D   L   S   Q   N   H   L   H
1921 ACCCTCCTGCCACGTGCCCTGGACAACCTCCCCAAAAGCCTGAAGCATCTGCATCTCCGT 1980
       T   L   L   P   R   A   L   D   N   L   P   K   S   L   K   H   L   H   L   R
1981 GACAATAACCTGGCCTTCTTCAACTGGAGCAGCCTGACCCTCCTGCCCAAGCTGGAAACC 2040
       D   N   N   L   A   F   F   N   W   S   S   L   T   L   L   P   K   L   E   T
2041 CTGGACTTGGCTGGAAACCAGCTGAAGGCCCTAAGCAATGGCAGCCTGCCATCTGGCACC 2100
       L   D   L   A   G   N   Q   L   K   A   L   S   N   G   S   L   P   S   G   T
2101 CAGCTGCGGAGGCTGGACCTCAGTGGCAACAGCATCGGCTTTGTGAACCCTGGCTTCTTT 2160
       Q   L   R   R   L   D   L   S   G   N   S   I   G   F   V   N   P   G   F   F
2161 GCCCTGGCCAAGCAGTTAGAAGAGCTCAACCTCAGCGCCAATGCCCTCAAGACAGTGGAG 2220
       A   L   A   K   Q   L   E   E   L   N   L   S   A   N   A   L   K   T   V   E
2221 CCCTCCTGGTTTGGCTCGATGGTGGGCAACCTGAAAGTCCTAGACGTGAGCGCCAACCCT 2280
       P   S   W   F   G   S   M   V   G   N   L   K   V   L   D   V   S   A   N   P
2281 CTGCACTGCGCCTGTGGGGCGACCTTCGTGGGCTTCCTGCTGGAGGTACAGGCTGCCGTG 2340
                                                        (SEQ ID NO:1  1615-2394)
       L   H   C   A   C   G   A   T   F   V   G   F   L   L   E   V   Q   A   A   V
                                                        (SEQ ID NO:2  521-780)
```

FIG. 4

```
2341 CCTGGGCTGCCCAGCCGCGTCAAGTGTGGCAGTCCGGGGCAGCTCCAGGGCCATAGCATC 2400
      P  G  L  P  S  R  V  K  C  G  S  P  G  Q  L  Q  G  H  S  I
2401 TTTGCGCAAGACCTGCGCCTCTGCCTGGATGAGACCCTCTCGTGGAACTGTTTTGGCATC 2460
      F  A  Q  D  L  R  L  C  L  D  E  T  L  S  W  N  C  F  G  I
2461 TCGCTGCTGGCCATGGCCCTGGGCCTGGTTGTGCCCATGCTGCACCACCTCTGCGGCTGG 2520
      S  L  L  A  M  A  L  G  L  V  V  P  M  L  H  H  L  C  G  W
2521 GACCTCTGGTACTGCTTCCACCTGTGCCTGGCCTGGCTGCCCCACCGAGGGCAGCGGCGG 2580
      D  L  W  Y  C  F  H  L  C  L  A  W  L  P  H  R  G  Q  R  R
2581 GGCGCAGACGCCCTGTTCTATGATGCCTTCGTGGTCTTTGACAAAGCTCAGAGTGCTGTG 2640
      G  A  D  A  L  F  Y  D  A  F  V  V  F  D  K  A  Q  S  A  V
2641 GCCGACTGGGTCTACAACGAGCTGCGGGTGCAGCTGGAGGAGCGCCGTGGGCGCCgCGCA 2700
      A  D  W  V  Y  N  E  L  R  V  Q  L  E  E  R  R  G  R  R  A
2701 CTGCGCCTGTGCCTGGAGGAGCGAGACTGGTTACCTGGCAAGACGCTCTTCGAGAACCTG 2760
      L  R  L  C  L  E  E  R  D  W  L  P  G  K  T  L  F  E  N  L
2761 TGGGCCTCAGTCTACAGCAGCCGCAAGACCCTGTTTGTGCTGGCCCACACGGACCGTGTC 2820
      W  A  S  V  Y  S  S  R  K  T  L  F  V  L  A  H  T  D  R  V
2821 AGCGGCCTCTTGCGTGCCAGTTTCCTGCTGGCCCAGCAGCGCCTGCTGGAGGACCGCAAG 2880
      S  G  L  L  R  A  S  F  L  L  A  Q  Q  R  L  L  E  D  R  K
2881 GACGTTGTAGTGCTGGTGATCCTGCGCCCCGATGCCTACCGCTCCCGCTACGTGCGGCTG 2940
      D  V  V  V  L  V  I  L  R  P  D  A  Y  R  S  R  Y  V  R  L
2941 CGCCAgCGCCTCTGCCGCCAGAGTGTCCTCCTCTGGCCCCACCAGCCCCGTGGGCAGGGC 3000
      R  Q  R  L  C  R  Q  S  V  L  L  W  P  H  Q  P  R  G  Q  G
3001 AGCTTCTGGGCCCAGCTGGGCACAGCCCTGACCAGGGACAACCGCCACTTCTATAACCGG 3060
      S  F  W  A  Q  L  G  T  A  L  T  R  D  N  R  H  F  Y  N  R
3061 AACTTCTGCCGGGGCCCCACGACAGCCGAATAG          3093 (SEQ ID NO:1 2395-3147)
      N  F  C  R  G  P  T  T  A  E  *             (SEQ ID NO:2 781-1030)
```

FIG. 6

```
SWINE   1   MGPRCT--LHPLSLLVQVTALAATLAQGRLPAFLPCELQPHGLVNCNWLFLKSVPHFSAA    58  SWINE
HUMAN   1   MGP-CRSALHPLSLLVQAIMLAMTLALGTLPAFLPCELQPHGLVNCNWLFLKSVPHFSMA    59  HUMAN
MOUSE   1   MVLRRRT-LHPLSLLVQAAVLAETLALGTLPAFLPCELKPHGLVDCNWLFLKSVPRFSAA    59  MOUSE
CAT     1   MGP-CHGALHPLSLLVQAAALAVALAQGTLPAFLPCELQPHGLVNCDWLFLKSVPHFSAA    59  CAT
             *  . ********* .  ** .** * ********* **** .* ******** ** *

SWINE   59  APRANVTSLSLLSNRIHHLHDSDFVHLSSLRTLNLKWNCPPAGLSPMHFPCHMTIEPNTF   118  SWINE
HUMAN   60  APRGNVTSLSLSSNRIHHLHDSDFAHLPSLRHLNLKWNCPPVGLSPMHFPCHMTIEPSTF   119  HUMAN
MOUSE   60  ASCSNITRLSLISNRIHHLHNSDFVHLSNLRQLNLKWNCPPTGLSPLHFSCHMTIEPRIF   119  MOUSE
CAT     60  APRGNVTSLSLYSNRIHHLHDSDFVHLSSLRRLNLKWNCPPASLSPMHFPCHMTIEPHTF   119  CAT
             *  *.*.*** ******** *** ** .** ********  ***.** ******  **

SWINE   119 LAVPTLEEINLSYNSITTVPALPDSLVSLSLSRTNILVLDPTHLIGLHALRYLYMDGNCY   178  SWINE
HUMAN   120 LAVPTLEEINLSYNNIMTVPALPKSLISLSLSHTNILMLDSASLAGLHAIRFLFMDGNCY   179  HUMAN
MOUSE   120 LAMRTLEEINLSYNGITTVPRLPSSLVNLSLSHTNILVLDANSIAGLYSIRVLFMDGNCY   179  MOUSE
CAT     120 LAVPTLEEINLSYNSITTVPALPSSLVSLSLSRTNILVLDPANLAGLHSLRFLFIDGNCY   179  CAT
             ** .********** * *** **  **  ****.*** *** **  *.** **  *****

SWINE   179 YKNPCQGALEVVPGALLGLGNLTHLSLKYNNLTEVPRSLPPSLETLLLSYNHIVTLIPED   238  SWINE
HUMAN   180 YKNPCRQAIEVAPGALLGLGNLTHLSLKYNNLTWPRNLPSSLEYLLLSYNRIVKLAPED   239  HUMAN
MOUSE   180 YKNPCTGAVKVTPGALLGLSNLTHLSLKYNNLTKVPRQLPPSLEYLLVSYNLIVKLGPED   239  MOUSE
CAT     180 YKNPCPQALQVAPGALLGLGNLTHLSLKYNNLTAVPRGLPPSLEYLLLSYNHIITLAPED   239  CAT
             *****  *  * ******* ************  **  **.***  **.*  *  .***

SWINE   239 LANLTALRVLDVGGNCRRCDHARNPCRECPKDHPKLHSDTFSHLSRLEGLVLKDSSLYNL   298  SWINE
                                                                  (SEQ ID NO:2 1-298)
HUMAN   240 LANLTALRVLDVGGNCRRCDHAPNPCMECPRHFPQLHPDTFSHLSRLEGLVLKDSSLSWL   299  HUMAN
                                                                  (SEQ ID NO:4 1-299)
MOUSE   240 LANLTSLRVLDVGGNCRRCDHAPNPCIECGQKSLHLHPETFHHLSHLEGLVLKDSSLHTL   299  MOUSE
                                                                  (SEQ ID NO:6 1-299)
CAT     240 LANLTALRVLDVGGNCRRCDHARNPCMECPKGFPHLHPDTFSHLNHLEGLVLKDSSLYNL   299  CAT
             *****.*************** *** **    . ** ** ** *.*********  *
                                                                  (SEQ ID NO:8 1-299)
```

FIG. 7

```
SWINE 299 DARWFRGLDRLQVLDLSENFLYDCITKTTAFQGLARLRKINLSFNYHKKVSFAHLHLAPS 358
HUMAN 300 NASWFRGLGNLRVLDLSENFLYKCITKTKAFQGLTQLRKINLSFNYQKRVSFAHLSLAPS 359
MOUSE 300 NSSWFQGLVNLSVLDLSENFLYESINHTNAFQNLTRLRKINLSFNYRKKVSFARLHLASS 359
CAT   300 NPRWFHALGNLMVLDLSENFLYDCITKTTAFQGLAQLRRLNLSFNYHKKVSFAHLHLAPS 359
              **  *  * ********** .* * *** *  ** ******* * **** * ** *

SWINE 359 FGHLRSLKELDMHGIFFRSLSETTLQPLVQLPMLQTLRLQMNFINQAQLSIFGAFPGLLY 418
HUMAN 360 FGSLVALKELDMHGIFFRSLDETTLRPLARLPMLQTLRLQMNFINQAQLGIFRAFPGLRY 419
MOUSE 360 FKNLVSLQELNMNGIFFRSLNKYTLRWLADLPKLHTLHLQMNFINQAQLSIFGTFRALRF 419
CAT   360 FGSLLSLQQLDMHGIFFRSLSETTLRSLVHLPMLQSLHLQMNFINQAQLSIFGAFPGLRY 419
            *  *   *  * * ******  ** *  **.* * *********. **  *   *

SWINE 419 VDLSDNRISGAARPVAITREVDGR-ERVWLPSRNLAPRPLDTLRSEDFMPNCKAFSFTLD 477
HUMAN 420 VDLSDNRISGASELTATMGEADGG-EKVWLQPGDLAPAPVDTPSSEDFRPNCSTLNFTLD 478
MOUSE 420 VDLSDNRISGPSTLSEATPEEADDAEQEELLSADPHPAPLSTPASKNFMDRCKNFKFTMD 479
CAT   420 VDLSDNRISGAMELAAATGEVDGG-ERVRLPSGDLALGPPGTPSSEGFMPGCKTLNFTLD 478
          **********  .   .   .  .  *  . .   *   *  * *  *    * **.*

SWINE 478 LSRNNLVTIQSEMFARLSRLECLRLSHNSISQAVNGSQFVPLTSLRVLDLSHNKLDLYHG 537
          (SEQ ID NO:2  299-537)
HUMAN 479 LGRNNLVTVQPEMFAQLSHLQCLRLSHNCISQAVNGSQFLPLTGLQVLDLSRNKLDLYHE 538
          (SEQ ID NO:4  300-538)
MOUSE 480 LSRNNLVTIKPEMFVNLSRLQCLSLSHNSIAQAVNGSQFLPLTNLQVLDLSHNKLDLYHW 539
          (SEQ ID NO:6  300-539)
CAT   479 LSRNNLVTIQPEMFARLSRLQCLLLSRNSISQAVNGSQFMPLTSLQVLDLSHNKLDLYHG 538
          *******  *** ** * ** *  * * ********* *** * *******
          (SEQ ID NO:8  300-538)
```

FIG. 8

```
SWINE  538 RSFTELPRLEALDLSYNSQPFTMQGVGHNLSFVAQLPALRYLSLAHNDIHSRVSQQLCSA 597
HUMAN  539 HSFTELPRLEALDLSYNSQPFGMQGVGHNFSFVAHLRTLRHLSLAHNNIHSQVSQQLCST 598
MOUSE  540 KSFSELPQLQALDLGYNSQPFSIKGIGHNFSFVAHLSMLHSLSLAHNDIHTRVSSHLNSN 599
CAT    539 RSFTELPRLEALDLSYNSQPFSMQGVGHNLSFVAQLPALRYLSLAHNDIHSRVSQQLCSA 598
           **.***.*.****.******....*.***.****.*..*.******.**..**..*.*

SWINE  598 SLCALDFSGNDLSRMWAEGDLYLRFFQGLRSLVWLDLSQNHLHTLLPRALDNLPKSLKHL 657
HUMAN  599 SLRALDFSGNALGHMWAEGDLYLHFFQGLSGLIWLDLSQNRLHTLLPQTLRNLPKSLQVL 658
MOUSE  600 SVRFLDFSGNGMGRMWDEGGLYLHFFQGLSGLLKLDLSQNNLHILRPQNLDNLPKSLKLL 659
CAT    599 SLRALDFSGNALSRMWAEGDLYLXFFRGLRSLVRLDLSQNRLHTLLPRTLDNLPKSLRLL 658
           *...******..**.***.*..*.**.**.*..**.**.****.**...*.*

SWINE  658 HLRDNNLAFFNWSSLTLLPKLETLDLAGNQLKALSNGSLPSGTQLRRLDLSGNSIGFVNP 717
HUMAN  659 RLRDNYLAFFKWWSLHFLPKLEVLDLAGNRLKALTNGSLPAGTRLRRLDVSQNSISFVAP 718
MOUSE  660 SLRDNYLSFFNWTSLSFLPNLEVLDLAGNQLKALTNGTLPNGTLLQKLDVSSNSIVSVVP 719
CAT    659 RLRDNYLAFFNWSSLVLLPRLEALDLAGNQLKALSNGSLPNGTQLQRLDLSSNSISFVAS 718
           .****.*.**.*.**...*.*.*.******.****.**.**.**.***.***.*.**.*.

SWINE  718 GFFALAKQLREINLSANALKTVEPSWFGSMVGNLKVLDVSANPLHCACGATFVGFLLEVQ 777
HUMAN  719 GFFSKAKELREINLSANALKTVDHSWFGPIASALQILDVSANPLHCACGAAFMDFLLEVQ 778
MOUSE  720 AFFALAVELKEVNLSHNILKTVDRSWFGPIVMNLTVLDVRSNPLHCACGAAFVDLLLEVQ 779
CAT    719 SFFALATRLREINLSANALKTVEPSWFGSLAGTLKVLDVTGNPLHCACGAAFVDFLLEVQ 778
           .**..*.*.*.****.*.****..****.*..*..***..*********.*..*.****

SWINE  778 AAVPGLPSRVKCGSPGQLQGHSIFAQDLRLCLDETLSWNCFGISLLAMALGLVVPMLHHL 837
                                                    (SEQ ID NO:2  538-837)
HUMAN  779 AAVPGLPSRVKCGSPGQLQGLSIFAQDLRLCLDEALSWDCFALSLLAVALGLGVPMLHHL 838
                                                    (SEQ ID NO:4  539-838)
MOUSE  780 TKVPGLANGVKCGSPGQLQGRSIFAQDLRLCLDEVLSWDCFGLSLLAVAVGMVVPILHHL 839
                                                    (SEQ ID NO:6  540-839)
CAT    779 AAVPGLPGHVKCGSPGQLQGRSIFAQDLRLCLDEALSWDCFGLSLLLVALGLAVPMLHHL 838
           ..****....******.***.************...***.**.**..**.*..**.***
                                                    (SEQ ID NO:8  539-838)
```

FIG. 9

```
SWINE   838 CGWDLWYCFHLCLAWLPHRGQRRGAD--ALFYDAFVVFDKAQSAVADWVYNELRVQLEER 895
HUMAN   839 CGWDLWYCFHLCLAWLPWRGRQSGRDEDALPYDAFVVFDKTQSAVADWVYNELRGQLEEC 898
MOUSE   840 CGWDVWYCFHLCLAWLPLLARSRRSAQA-LPYDAFVVFDKAQSAVADWVYNELRVRLEGR 898
CAT     839 CGWDLWYCFHLCLAWLPRRGRRRGAD--ALPYDAFVVFDKAQSAVADWVYNELRVRLEER 896
            ****.**********   ..  ..  *.********.*************.  **..

SWINE   896 RGRRALRLCLEERDWLPGKTLFENLWASVYSSRKTLFVLAHTDRVSGLLRASFLLAQQRL 955
HUMAN   899 RGRWALRLCLEERDWLPGKTLFENLWASVYGSRKTLFVLAHTDRVSGLLRASFLLAQQRL 958
MOUSE   899 RGRRALRLCLEDRDWLPGQTLFENLWASIYGSRKTLFVLAHTDRVSGLLRTSFLLAQQRL 958
CAT     897 RGRRALRLCLEERDWLPGKTLFENLWASVYSSRKMLFVLAHTDRVSGLLRASFLLAQQRL 956
            ***.*******.***.*********.*.***.*.*************.*********

SWINE   956 LEDRKDVWLVILRPDAYRSRYVRLRQRLCRQSVLLWPHQPRGQGSFWAQLGTALTRDNR 1015
HUMAN   959 LEDRKDVWLVILSPDGRRSRYVRLRQRLCRQSVLLWPHQPSGQRSFWAQLGVALTRDNH 1018
MOUSE   959 LEDRKDVWLVILRPDAHRSRYVRLRQRLCRQSVLFWPQQPNGQGGFWAQLSTALTRDNR 1018
CAT     957 LEDRKDVWLVILRPDAHRSRYVRLRQRLCRQSVLLWPHQPSGQRSFWAQLGTALTRDNQ 1016
            ************ ** .**************** .** ** ..***** ******.

SWINE  1016 HFYNRNFCRGPTTAE  (SEQ ID NO:2  838-1030)                 1030
HUMAN  1019 HFYNRNFCQGP-TAE  (SEQ ID NO:4  839-1032)                 1032
MOUSE  1019 HFYNQNFCRGP-TAE  (SEQ ID NO:6  840-1032)                 1032
CAT    1017 HFYNQNFCRGPTTAE  (SEQ ID NO:8  839-1031)                 1031
            ****.***.**
```

USE OF TOLL-LIKE RECEPTOR-EXPRESSING CELLS

This application is a National Stage Application of International Application Number PCT/JP2004/002920, filed Mar. 5, 2004; which claims priority to Japanese Application 2003-172132, filed Jun. 17, 2003.

TECHNICAL FIELD

The present invention relates to use of cells expressing a Toll-like receptor.

BACKGROUND ART

Two immune systems, innate and acquired, are known in a living body. In contrast to acquired immunity, which is found only in higher organisms such humans, the innate immune system is conserved from insects to humans in a wide range of organisms. When external pathogenic bacteria or such invade, cells responsible for the innate immunity (for example, macrophages and dendritic cells) function as the first-stage prevention of infections: quickly detect pathogenic bacteria or such, directly attack the pathogenic bacteria or such through phagocytosis or such, and release alarm signals such as cytokines to activate the acquired immune system. Toll-like receptors (TLRs) play a role in the first detection of bacteria in a series of immune responses. Ten types of TLRs have been identified in human so far, each being considered a receptor recognizing a different molecular structure (Non-Patent Document 1). Of these, TLR9, which was first reported by the research group of Akira et al. in 2000, was identified as a receptor that recognizes bacterial DNA, in particular the CpG motif (Non-Patent Document 2 and Patent Document 1).

Previous studies have reported the effect of lipopeptides on the expression activity of NF-κB in human TLR2-expressing CHO cells, as well as the effect of various CpG DNA motifs derived from pathogenic *E. coli* on cytokine (IL-8) yield in human TLR9-expressing HEK293 cells (Non-Patent Documents 3 to 5).

Information on prior art documents relevant to the invention of the present application is listed below.

[Patent Document 1] Japanese Patent Application Kokai Publication No. (JP-A) 2002-34565 (unexamined, published Japanese patent application)

[Non-Patent Document 1] O. Takeuchi, S. Akira, International Immunopharmacology 1 (2001) 625-635

[Non-Patent Document 2] H. Hemmi et al., Nature 408 (2000) 740-745

[Non-Patent Document 3] Yoshimura A., Takada H., Kaneko T., Kato I., Golenbock D., Hara Y., "Structural requirements of muramylpeptides for induction of Toll-like receptor 2-mediated NF-kappaB activation in CHO cells." Journal of Endotoxin Research 6 (5): 407-20, 2000.

[Non-Patent Document 4] Klinman D M., Takeshita F., Gursel I., Leifer C., Ishii K J., Verthelyi D., Gursel M., "CpG DNA: recognition by and activation of monocytes." Microbes & Infection 4 (9): 897-901, 2002 July.

[Non-Patent Document 5] Takeshita F., Leifer C A., Gursel I., Ishii K J., Takeshita S., Gursel M., Klinman D M., "Cutting edge: Role of Toll-like receptor 9 in CpG DNA-induced activation of human cells." Journal of Immunology 167 (7): 3555-8, 2001 Oct. 1.

DISCLOSURE OF THE INVENTION

The present inventors have revealed that certain DNA motifs derived from dairy lactic acid bacteria, including probiotic lactobacilli, can exhibit immuno potentiation of the intestinal tract immune system (H. Kitazawa et al., Int. J. Food Microbiol. 65 (2001) 149-162; H. Kitazawa et al., Int. J. Food Microbiol. (2003) in press). This finding implies that TLR9 recognizes not only DNA from pathogenic bacteria, but also DNA from dietary lactobacilli, and thus contributes to immunity activation. In the future, TLR9 can become an important tool not only in the negative evaluation of pathogenic bacteria but also in the development of functional food products using dairy lactic acid bacteria (LAB), provided that recognition towards various DNA motifs and systems for activity assessment can be established.

In the development of functional food products, it is necessary to evaluate their ultimate effects on human, and for obtaining basic findings, investigation using experimental animals and animal cells is essential. To this end, the present invention focused on pigs as an experimental animal, which has great potential utility as a human model system from aspects of organ transplantation and such, and is of great significance in food industry. In order to establish cells in which TLR9 is expressed for use in systems of assessing functional DNA, the present inventors decided to clone a swine TLR9 gene, and introduce the gene to express it in animal cells.

The present invention has been made in view of the above conditions. An objective of the present invention is to provide uses of TLR9-expressing cells.

The present inventors cloned from the Peyer's patches of a swine intestinal tract a gene of Toll-like receptor 9, which is a receptor protein that recognizes the CpG DNA motif derived from pathogenic bacteria, and established animal cells (transfectants) in which swine TLR9 (sTLR9) is expressed. The presence of the sTLR9 protein in these animal cells is confirmed by generation and use of polyclonal antibodies against sTLR9. The sTLR9 transfectant was analyzed for its functionality on CpG DNA, and its application to systems for assessing LAB's DNA activity was sought.

Specifically, this was carried out according to the following (1) through (5):

(1) Total RNA was extracted from the Peyer's patch of a swine intestinal tract. Using primers prepared from highly conserved regions of human and mouse TLR9 genes, RT-PCR and RACE were performed to clone the swine TLR9 gene. The gene's full-length sequence was determined.

(2) The full-length amino acid sequence of swine TLR9 obtained from the genetic information was screened for antigenic determinant sites. The selected region was synthesized by peptide synthesis and used as an antigen for generating a swine TLR9 polyclonal antibody. Rabbits were immunized with the chemically synthesized antigen to generate polyclonal antibodies against swine TLR9 using standard techniques.

(3) HEK293T cells (human embryonic kidney cells) were transfected with the swine TLR9 gene to establish swine TLR9 gene-transfected cells (transfectant).

(4) SwineTLR9 expression in the HEK293T cells was confirmed by detecting swine TLR9 mRNA expression using RT-PCR. The expression of the swine TLR9 protein was confirmed by immunostaining with a swine TLR9 polyclonal antibody using laser microscopy and flow cytometry.

(5) The reactivity of swine TLR9 against oligodeoxynucleotides (CpG2006 and CpG1826), which contain specific CpG DNA motifs that strongly stimulate human and mouse cells respectively, was analyzed.

The swine TLR9 gene, as revealed from the analysis result, is consisted of 3090 bases encoding 1029 amino acid residues. (MW: 115.8 kDa). A 3145 bp-long cDNA sequence comprising the swine TLR9 gene was determined. The amino acid sequence of swine TLR9 shows an extremely high homology to human TLR9 (82.9%) and a 74.9% homology to mouse TLR9, therefore swine TLR9 shows a relatively higher homology to human TLR9 than to mouse TLR9. The results of RT-PCR and immunostaining with a swine TLR9 polyclonal antibody revealed that the swine TLR9 protein was expressed as a membrane protein in the swine TLR9 transfectant, indicating successful creation of the swine TLR transfectant. Functional analysis conducted against CpG DNAs using this transfectant indicated that swine TLR9 has a higher reactivity with CpG2006 than with CpG1826. This analysis revealed that swine TLR9 can recognize a human-specific CpG DNA motif more effectively than a mouse-specific CpG DNA motif. Surprisingly, the results of comparing the levels of mRNA expression in various tissues by real-time PCR revealed that the mRNA expression in the Peyer's patches and mesenteric lymph nodes, which are tissues that have a central role in the intestinal tract immune system, was three or more times higher than in that of the spleen.

Accordingly, the present invention provides the following (1) to (21):

[1] A method for assessing whether a test sample activates the intestinal tract immune system, comprising the steps of:
  (a) contacting a test sample with a cell expressing an intestinal tract tissue-expressed Toll-like receptor; and
  (b) measuring activity of the Toll-like receptor using signal transduction in the cell as an indicator,
  wherein the test sample is judged to be activating the intestinal tract immune system if the activity of the Toll-like receptor is increased as compared to activity of the Toll-like receptor in a cell not contacted with the test sample;
[2] a method of screening for a sample that activates the intestinal tract immune system, comprising the steps of:
  (a) assessing whether a plurality of test samples activate the intestinal tract immune system by the assessment method of [1]; and
  (b) selecting from the plurality of test samples those assessed to activate the intestinal tract immune system;
[3] a method for producing a pharmaceutical composition that activates the intestinal tract immune system, comprising the steps of [2] and a further step of mixing the sample assessed to activate the intestinal tract immune system with a pharmaceutically acceptable carrier;
[4] a method for assessing whether a test microorganism activates the intestinal tract immune system, comprising the steps of:
  (a) preparing an extract from a test microorganism;
  (b) contacting the extract with a cell expressing an intestinal tract tissue-expressed Toll-like receptor; and
  (c) measuring activity of the Toll-like receptor using signal transduction in the cell as an indicator,
  wherein the test microorganism is judged to be activating the intestinal tract immune system if the activity of the Toll-like receptor is increased as compared to activity of the Toll-like receptor in a cell not contacted with the extract;
[5] a method of screening for a microorganism that activates the intestinal tract immune system, comprising the steps of:
  (a) assessing whether a plurality of test microorganisms activate the intestinal tract immune system by the assessment method of [4]; and
  (b) selecting from the plurality of test microorganisms those assessed to activate the intestinal tract immune system;
[6] a method for producing a food composition that activates the intestinal tract immune system, comprising the steps of [5], and a further step of mixing the microorganism assessed to activate the intestinal tract immune system with a dietarily acceptable carrier;
[7] the method of [6], wherein the microorganism is a lactic acid bacterium and the food composition is a dairy product;
[8] the method of any one of [4] to [6], wherein the microorganism is a lactic acid bacterium;
[9] the method of [8], wherein the bacterium is a lactic acid bacterium;
[10] a method for constructing a model intestinal immunocompetent cell, comprising the step of introducing into a cell an expression vector comprising a DNA encoding an intestinal tract tissue-expressed Toll-like receptor;
[11] use of a cell expressing an intestinal tract tissue-expressed Toll-like receptor as a model intestinal immunocompetent cell;
[12] the method of any one of [1] to [11], wherein the intestinal tract tissue is intestinal lymphoid tissue;
[13] the method of [12], wherein the intestinal lymphoid tissue is Peyer's patch or intestinal lymph node;
[14] the method of any one of [1] to [13], wherein the Toll-like receptor is derived from swine;
[15] the method of any one of [1] to [13], wherein the Toll-like receptor is Toll-like receptor 9;
[16] a cell expressing an intestinal tract tissue-expressed Toll-like receptor for use in the method of any one of [1] to [9];
[17] a model intestinal immunocompetent cell constructed by introducing into a cell an expression vector comprising a DNA encoding an intestinal tract tissue-expressed Toll-like receptor;
[18] the cell of [16] or [17], wherein the intestinal tract tissue is intestinal lymphoid tissue;
[19] the cell of [18], wherein the intestinal lymphoid tissue is Peyer's patch or intestinal lymph node;
[20] the cell of any one of [16] to [19], wherein the Toll-like receptor is derived from swine; and
[21] the method of any one of [16] to [19], wherein the Toll-like receptor is Toll-like receptor 9.

Toll-like receptor 9 (TLR9), which is involved in the activation of immune response, has been known to be strongly expressed in the spleen (Zarember K A. and Godowski P J. Journal of Immunology. 168 (2002) 554-561). In contrast, the present inventors discovered for the first time that TLR9 is strongly expressed in intestinal lymphoid tissues, in particular, the Peyer's patches and mesenteric lymph nodes.

The intestinal tract, a boundary tissue between the interior and the exterior of a human body, is constantly exposed to external stimuli (e.g., microorganisms, such as bacteria and viruses, drugs, food additives, residual pesticides in food, and environmental pollutants).

Therefore, the intestinal tract serves not only to absorb orally ingested nutrients, but also as a first biological defense mechanism (first defense line) in the receipt, transportation, response and elimination of foreign substances (Mantis N J. et al., J. Immunol. 169 (2002) 1844-1851). Other defense mechanisms including lymphoid tissues and gut-associated lymphoid tissues (GALT) are present. GALT is made up of diffusive compositions and aggregative compositions. The diffusive compositions include intestinal intraepithelial lymphocytes and lymphocytes of the lamina propria mucosae, and the aggregative compositions include the Peyer's patches, lymphoid follicles and mesenteric lymph nodes (Spahn T W. et al., Eur. J. Immunol. 32 (2002): 1109-1113). The Peyer's patches are covered with follicle-associated epithelium (FAE) and form dorm-like elevations in villus-free areas. The patches include a follicular area where germinal center B-cells are present and a parafollicular area where helper T-cells are present (Owen R L. Sem. Immunol. 11 (1999) 157-163). Membranous epithelial cells (M-cells), which are specialized epithelial cells that serve as the first line of defense in the local immune mechanism of intestinal tract, are dispersed in FAE. M-cells have a deep pocket that serves as a "tunnel" in which antigens are transported through the cytoplasm to the basolateral side, where they are presented to antigen-presenting cells, including B-cells, dendritic cells and macrophages. M-cells have also been found in the epithelial mucosa of trachea and reported to serve as an entry site for pathogens such as *Bacillus* tuberculosis (Teitelbaum R. et al., Immunity. 10 (1999) 641-650). M-cells are also known to serve as an entry site for functional factors contained in food products, as well as for microorganisms and food antigens. Once taken up by M-cells, intestinal luminal antigens (especially macromolecules) are transported to the inside of Peyer's patches, where they come into contact with major histocompatibility complex (MHC) class II-positive antigen-presenting cells such as dendritic cells and macrophages (Kaneko K. et al., J. Veterinary. Med. Sci. 61 (1999) 1175-1177; Gebert A. et al., American J. Pathology. 154 (1999) 1573-1582; Jensen V B. et al., Infection & Immunity. 66 (1988) 3758-3766; Penheiter K L. et al., Mol. Microbiol. 24 (1997) 697-709; Debard N. et al., Gastroenterology. 120 (2001) 1173-1182; Gebert A. et al., Int. Rev. Cytology. 167 (1996) 91-159). Upon antigen stimulation, helper T-cells produce Fc receptors, antigen-binding factors (IBF), IL-2, IL-4, IL-5 and IL-6. T-cells and B-cells which are activated upon antigen presentation then start "homing": migrate via mesenteric lymph nodes into the thymus and are then transported via circulation into tissues under action, such as intestinal lamina propria mucosae, mammary gland, lacrymal gland, salivary gland and urogenital organs. B-cells then become plasma cells to produce IgA. The secretory. IgA acts to eliminate viruses, bacteria, bacteriotoxins and allergens that enter the intestinal tract and other mucous tissues (Vaerman J P. et al., Immunology. 54 (1985) 601-603; Machtinger S, and Moss R., J. Allergy. Clinical. Immunol. 77 (1986) 341-347; Mathewson B. et al, J. Infectious Diseases. 169 (1994) 614-617). Mesenteric lymph nodes develop beneath the Peyer's patches, where more lymphocytes, dendritic cells and macrophages are present across the Peyer's patches. The Peyer's patches and mesenteric lymph nodes thus play a central role in the intestinal tract immune system (immune system in the intestinal tract as above).

Meanwhile, the relation between intestinal mucosal epithelial cells and the uptake of FITC (fluorescein isothiocyanate)-labeled lipopolysaccharide (LPS), which is a known ligand of TLR4 and has been obtained from simian intestinal epithelium were analyzed using a TLR4 antibody and an IRAK antibody. The results indicated that LPS was taken up by the intestinal epithelial cells expressing TLR4 and IRAK and was transported to lamina propria mucosae (Imaeda H. et al., Histochemical Cell Biology. 118 (2002) 381-388). This observation suggests intestinal tract tissue-expressed TLRs, such as TLR9, are involved in the intestinal tract immune system.

In view of the foregoing knowledge, the present invention provides methods for assessing whether a test sample activates the intestinal tract immune system or not. In this method, the test sample is first contacted with cells (TLR transfectant) expressing an intestinal tract tissue-expressed TLR. In this step, the test sample is brought into contact with TLR on the surface of the transfectant. Activity of the TLR is then measured using signal transduction in the TLR transfectant as an indicator. In this assessment method, the test sample is judged to be activating the intestinal tract immune system if the TLR activity is increased as compared to that in a transfectant that has not been contacted with the test sample.

Examples of the test sample in the present invention include, but are not limited to, single compounds such as DNA, DNA fragments, natural compounds, organic compounds, inorganic compounds, proteins and peptides, and compound libraries, expression products of gene libraries, supernatants of nonmammalian cell cultures, extracts of non-mammalian cells, products of microbial fermentation, supernatants of microbial cultures, extracts of microorganisms, extracts of marine organisms and plant extracts. While the DNA fragments may be of any origin, those with a CpG motif, AT motif or CpG-like motif are preferred. Examples of microbial extracts include cell walls, cell membranes, DNA, RNA and flagella. Examples of microorganism include bacteria and yeast. Bacteria include pathogenic bacteria and lactobacillus. When necessary, the test sample may be labeled, for example, with a radiolabel or a fluorescent label.

The "intestinal tract" in the present invention includes, but is not limited to, duodenum, jejunum and ileum. While the intestinal tract tissue in the present invention may be any intestinal tract tissue, it is preferably an intestinal lymphoid tissue, more preferably a Peyer's patch or intestinal lymph node, and even more preferably a Peyer's patch or intestinal lymph node obtained from ileum.

In the present invention, the "intestinal tract tissue-expressed TLR" encompasses all types of TLRs, including, for example, TLR1 to TLR10. Ten different types of TLRs have been identified and reported up to now, each in the TLR family recognizing a different molecule, i.e., bacterial modulin. Bacterial modulins are defined as pathogen-associated molecular patterns (PAMPs) that show ability to induce cytokines in hosts and control their immune responses. TLRs are known to contain leucine-rich repeats (LRRs) on their extracellular domain and an intracellular TIR domain homologous to interleukin 1 receptor. Organisms from which the intestinal tract tissue-expressed TLR is derived include pigs, humans, mice, cats, vertebrates and invertebrates, and general organisms.

Examples of TLR9 in the present invention are proteins comprising the amino acid sequence shown in SEQ ID NO: 2, 4, 6 or 8. DNA coding for the proteins comprising the amino acid sequence shown in SEQ ID NO: 2, 4, 6 or 8 can be prepared by preparing RNA from thymus, lung, spleen, duodenum, Peyer's patch, mesenteric lymph node or such, synthesizing cDNA using reverse transcriptase, performing PCR to amplify the cDNA that codes for an above protein using oligo DNAs that have been synthesized based on SEQ ID NO: 1, 3, 5 or 7 as primers.

The "TLR9" in the present invention also includes proteins functionally equivalent to proteins comprising the amino acid sequence shown in SEQ ID NO: 2, 4, 6 or 8. Such proteins include mutants, alleles, variants and homologues of proteins comprising the amino acid sequence shown in SEQ ID NO: 2, 4, 6 or 8. As used herein, the term "functionally equivalent" means that a protein of interest has biological functions (biological roles) or biochemical functions (biochemical activities) equivalent to those of proteins comprising the amino acid sequence shown in SEQ ID NO: 2, 4, 6 or 8.

On recognizing microbial components, TLRs activate intracellular signal transduction pathways and facilitate translocation of IL-1 receptor-associated kinase (IRAK), TNF receptor-associated factor 6 (TRAF6) and transcription factor NF-κB to the nucleus, via a common adaptor molecule, MyD88. This ultimately induces production of various inflammatory cytokines, such as tumor necrosis factor α (TNF-α), interleukin (IL)-6, IL-12, IL-18 and IFN-γ, and expression of cell surface co-stimulatory molecules (Kaisho T. and Akira S. Trends in Immunology. 22 (2001) 78-83). Since TLRs primarily recognize pathogen carbohydrates, lipids and nucleic acids, they serve to compensate for the acquired immunity, which recognizes proteins.

The biological functions and biochemical functions of proteins comprising the amino acid sequence shown in SEQ ID NO: 2, 4, 6 or 8 include ability to recognize microbial components, ability to activate intracellular signal transduction pathways, ability to induce expression of inflammatory cytokines, and ability to induce expression of cell surface co-stimulatory molecules.

Methods for preparing DNAs encoding a protein functionally equivalent to a certain protein include methods using hybridization techniques (Sambrook, J et al., "Molecular Cloning" 2nd ed., 9.47-9.58, Cold Spring Harbor Lab. Press, 1989). Specifically, the nucleotide sequence shown in SEQ ID NO: 1, 3, 5 or 7, or a fragment thereof, can be used to isolate DNAs encoding proteins that are functionally equivalent to a protein comprising the amino acid sequence shown in SEQ ID NO: 2, 4, 6 or 8.

One skilled in the art may appropriately select the hybridization conditions required for isolating DNAs encoding proteins functionally equivalent to a protein comprising the amino acid sequence shown in SEQ ID NO: 2, 4, 6 or 8, and hybridization conditions such as low-stringency conditions may be used. For low-stringency conditions, the after-hybridization wash is, for example, 42° C., 5×SSC and 0.1% SDS, and more preferably 50° C., 5×SSC and 0.1% SDS. More preferred hybridization conditions are high-stringency conditions, for example, 65° C., 0.1×SSC and 0.1% SDS. Under these conditions, DNAs with higher homology can be efficiently obtained at higher temperatures. It should be noted that a number of parameters affecting the stringency of hybridization, such as temperature and salt concentration, are considered. Those skilled in the art can choose these parameters appropriately to achieve similar stringency.

Alternatively, using primers synthesized based on the sequence information shown in SEQ ID NO: 1, 3, 5 or 7, DNAs encoding proteins functionally equivalent to a protein comprising the amino acid sequence shown in SEQ ID NO: 2, 4, 6 or 8 may be isolated by gene amplification techniques, such as polymerase chain reaction (PCR).

Proteins that are encoded by DNAs isolated using hybridization or gene amplification techniques, and which are functionally equivalent to a protein comprising the amino acid sequence shown in SEQ ID NO: 2, 4, 6 or 8, generally have high homologies to a protein comprising the amino acid sequence shown in SEQ ID NO: 2, 4, 6 or 8 at the amino acid level. The term "high homology" used herein means at least 60% homology, preferably 70% or higher homology, more preferably 80% or higher homology, more preferably 90% or higher homology, still more preferably 95% or higher-homology, and most preferably 98% or higher homology at the amino acid level.

The similarity of amino acid sequences or nucleotide sequences can be determined using the BLAST algorithm by Karlin and Altschul (Proc. Natl. Acad. Sci. USA 90:5873-5877, 1993). Programs such as BLASTN and BLASTX have been developed based on this algorithm (Altschul et al., J. Mol. Biol. 215:403-410, 1990). When nucleotide sequences are analyzed by the BLAST-based BLASTN, parameters are set to, for example, score=100 and word-length=12. When amino acid sequences are analyzed by the BLAST-based BLASTX, parameters are set to, for example, score=50 and word-length=3. When BLAST is used in conjunction with the Gapped BLAST program, default parameters of each program are used. Specific procedures of these analytical techniques are known (http://www.ncbi.nlm.nih.gov.).

The present invention encompasses proteins comprising an amino acid sequence with one or more amino acid mutations in the amino acid sequence shown in SEQ ID NO: 2, 4, 6 or 8. Such amino acid mutations can occur naturally. The number of amino acid mutations is typically 30 amino acids or less, preferably 15 amino acids or less, more preferably 5 amino acids or less, and still more preferably 2 amino acids or less.

The methods of the present invention use the above-described TLR transfectant. The TLR transfectant can be obtained by introducing into a cell an expression vector that comprises a DNA encoding an intestinal tract tissue-expressed TLR. Examples of such an expression vector include mammalian expression vectors (e.g., pcDNA3 (Invitrogen), pEGF-BOS (Nucleic Acids. Res. 1990, 18(17), p 5322), pEF and pCDM8), insect expression vectors (e.g., "Bac-to-BAC baculovirus expression system" (Invitrogen) and pBac-PAK8), animal virus expression vectors (e.g., pHSV, pMV and pAdexLcw) and retroviral expression vectors (e.g., pZIP-neo).

For expression in animal cells such as CHO cells, COS cells and NIH3T3 cells, the expression vector must carry a suitable promoter for cellular expression. Examples of such promoters include SV40 promoter (Mulligan et al., Nature (1979) 277, 108), MMLV-LTR promoter, EF1α promoter (Mizushima et al., Nucleic Acids Res. (1990) 18, 5322) and CMV promoter. More preferably, the expression vector may have a gene for selection of transformed cells (for example, a drug resistance gene that allows selection by a drug such as neomycin or G418).

To ensure stable expression of a gene and amplify copy number of the gene in cells, the gene may be amplified by introducing a vector (e.g., pCHOI) having a complementary dihydrofolate reductase gene (dhfr gene) introduced into CHO cells, whose nucleic acid synthesis pathways are defective, and using methotrexate (MTX). Methods for transiently expressing a gene include those that transform COS cells, which carry an SV40 T antigen-expressing gene on their chromosome, with a vector having an SV40 replication origin (e.g., pcD). The replication origin may be obtained from polyomavirus, adenovirus bovine papillomavirus (BPV) or such. The expression vector may further comprise a selection marker, such as aminoglycoside transferase (APH) gene, thymidine kinase (TK) gene or dhfr gene, to amplify the gene copy number in host cell system.

The host cells include, but are not limited to, mammalian cells and insect cells. Known examples of mammalian cells include HEK293T cells, CHO (J. Exp. Med (1995) 108, 945), COS, NIH3T3, myeloma, BHK (baby hamster kidney), HeLa and Vero. Known examples of insect cells include Sf9, Sf21 and Tn5.

CHO cells, in particular, dhfr-CHO having a defective dhfr gene (Proc. Natl. Acad. Sci. USA (1980) 77, 4216-4220) and CHO K-1 (Proc. Natl. Acad. Sci. USA (1968) 60, 1275), are preferably used. CHO cells are particularly preferred when the objective is to have abundant expression of a gene in animal cells. In addition, immortalized cell lines are preferred host cells.

The vector can be introduced into host cells using methods known by one skilled in the art, including, for example, calcium phosphate, DEAE dextran, cationic ribosome DOTAP (Roche Diagnostics), electroporation, and lipofection.

In the present invention, the TLR activity is measured by using signal transduction in the above-described transfectant as an indicator. For example, the TLR activity can be measured by using expression levels of cytokines (e.g., IL-6, IL-12, IFN-γ and TNF-α), activation of molecules involved in signal transduction pathways (e.g., NF-κB, JNK and IRAK), or such as an indicator. The expression of a cytokine can be detected at the mRNA or protein level. For example, the expression of a cytokine at the protein level can be measured by using existing kits for human, including human IL-6, IL-12, TNF-α and IFN-γ ELISA kits (TRB, INC.). Increase in the activities of molecules in signal transduction pathways can be detected by luciferase assay. For example, a swine TLR transfectant is transfected with a plasmid vector (pGLM-ENH) comprising NF-κB and a luciferase gene, and stimulated with a ligand (e.g., DNA) 18 hours later. The cells are lysed 24 hours after stimulation, and then the cell lysate is collected and stored at −80° C. until use. The luciferase activity is determined by adding a luciferin-containing reaction solution to the cell lysate, and measuring the change in luminescence over an eight-second period starting at 2 seconds after the addition. The same procedure is repeated three times for each sample and averages are taken. Higher luminescence intensity indicates stronger NF-κB activity.

The present invention also provides methods of screening for samples that activate the intestinal tract immune system. In the screening methods of the present invention, a plurality of test samples are assessed for the ability to activate the intestinal tract immune system, using the above-described assessment methods. Samples that are assessed as activating the intestinal tract immune system are selected.

Further, samples that bind to an intestinal tract tissue-expressed TLR may be screened in advance and used as test samples. The TLR used to screen for samples that bind to an intestinal tract tissue-expressed TLR may be a recombinant protein or a naturally occurring protein. The TLR used in screening may be a partial peptide. To screen for samples that bind to an intestinal tract tissue-expressed TLR, a plurality of test samples are first contacted with an intestinal tract tissue-expressed TLR. Binding of the TLR with the test samples is detected. Test samples that bind to the TLR are then selected. The binding of the TLR with the test samples can be detected by methods known to one skilled in the art.

The samples obtained in the above-described assessment methods or screening methods can be used as samples having an immunostimulatory function in the treatment or prevention of diseases, for example, allergies, cancers, and infections.

The present invention further provides methods for producing pharmaceutical compositions that activate the intestinal tract immune system. The pharmaceutical compositions of the present invention can be used as pharmaceutical compositions having an immunostimulatory function in the treatment or prevention of diseases, for example, allergies, cancers, and infections. The pharmaceutical compositions of the present invention are preferably uses as vaccines.

In methods for producing the pharmaceutical compositions of the present invention, a sample that has been assessed as activating the intestinal tract immune system by the above-described screening methods is mixed with a pharmaceutically acceptable carrier. One example of such a pharmaceutically acceptable carrier is adjuvant (antibody production potentiator). Other examples of pharmaceutically acceptable carriers include surfactants, excipients, coloring agents, flavoring agents, preservatives, stabilizing agents, buffering agents, suspending agents, isotonizing agents, binding agents, disintegrating agents, lubricants, fluidity accelerators, and corrigents. Other commonly used carriers may also be used suitably. Specific examples include light silicic acid anhydride, lactose, crystalline cellulose, mannitol, starch, carmellose calcium, carmellose sodium, hydroxypropylcellulose, hydroxypropylmethylcellulose, polyvinylacetal diethylaminoacetate, polyvinylpyrrolidone, gelatin, middle-chain fatty acid triglycerides, polyoxyethylene hydrogenated castor oil 60, sucrose, carboxymethylcellulose, corn starch and inorganic salts. The thus produced pharmaceutical compositions which activate the intestinal tract immune system can be used as oral agents or injections.

The present invention further provides methods for assessing whether a test microorganism activates the intestinal tract immune system. Examples of microorganisms in the present invention include, but are not limited to, bacteria and yeast. The bacteria include, but are not limited to, LAB (e.g., LAB that is indigenous to the intestines and dairy LAB).

In the assessment methods, extracts are prepared from a test microorganism. Examples of such microorganism extracts include cell walls, cell membranes, DNAs, RNAs and flagella. Preferred DNAs are fragments containing a CpG motif, AT motif or CpG-like motif. Such extracts can be prepared from the microorganisms by methods known by one skilled in the art.

An example of the method for preparing fragments containing a CpG motif, AT motif or CpG-like motif from dairy LAB is shown below, but methods of the present invention are not limited thereto.

Lactobacilli and Streptococci are subcultured (37° C., 24 hours) three times in Lactobacilli MRS broth (Difco Laboratories, Detroit, Mich., USA) and in Elliker broth, respectively. Subsequently, the bacteria are inoculated at 1% in a 50 ml medium and are cultured at 37° C. for 16 hours. The cells are then collected by centrifugation (3,000×g, 4° C., 20 min), washed twice by centrifugation (4,000×g, 4° C., 20 min) in TE buffer (10 mM Tris-Cl, 1 mM EDTA pH 7.5), and then resuspended in 5.0 mL of TE buffer. To this suspension, 2.5 ml of lysozyme (30 mg/ml, Seikagaku Co. Ltd., Tokyo) and 20 µl of N-acetylmuramidase SG (250 µg/ml, Seikagaku Co. Ltd., Tokyo) are added and the reaction is carried out at 37° C. for 10 to 30 minutes. To this suspension, 10 ml of 0.1 M Tris-1% SDS solution is then added and the solution was gently stirred. Subsequently, a proteinase K solution (20 mg/ml, 150 µl, TaKaRa, Kyoto) is then added and stirred, and the reaction is carried out at 37° C. overnight. To this mixture, 5 M NaCl solution (2.5 ml) is added and the mixture is transferred to a sterilized beaker. 100% ethanol (50 ml) is then added to precipitate the nucleic acid. The resulting precipitate is picked up using a sterilized glass rod, washed with 70% ethanol, and dissolved in TE buffer (10 ml). The solution is allowed to stand at 4° C. overnight to completely dissolve the precipitate. Following addition of RNase A (10 mg/ml, 100 µl, SIGMA) and subsequent incubation at 37° C. for 60 min, $\frac{1}{10}$ volume of 5 M NaCl (1 ml) and an equal volume of 100% ethanol are added to precipitate the nucleic acid. The resulting precipitate is wound onto a sterilized glass rod, washed with 70% ethanol, and dissolved in a TE buffer (20 ml). The thus purified DNA is then stored at 4° C. until use. The chromosomal DNA is digested with restriction enzyme Sau 3AI and the digest is subjected to 3% agarose gel electrophoresis. The DNA collected from the agarose gel is ligated into a plasmid vector. Sequence of the cloned DNA is then determined on a sequencer to prepare fragments having a CpG motif, AT motif or CpG-like motif.

In the assessment methods, the TLR transfectant is contacted with the extract, and activity of the intestinal tract tissue-expressed TLR is measured by using signal transduction in the transfectant as an indicator. The test microorganism is judged as activating the intestinal tract immune system if the TLR activity is increased when compared to the activity in cells that are not contacted with the extract.

The present invention further provides methods of screening for microorganisms that activate the intestinal tract immune system. In these screening methods, the above-described assessment methods are used to evaluate multiple test microorganisms for their ability to activate the intestinal tract immune system, and the microorganisms evaluated as activating the intestinal tract immune system are selected.

The microorganisms obtained in the assessment methods or screening methods can be used as microorganisms having immunostimulatory function in the treatment or prevention of diseases, for example, allergies, cancers, and infections.

The microorganisms which activate the intestinal tract immune system can be used to make food compositions that activate the intestinal tract immune system. The present invention also provides methods for producing food compositions that activate the intestinal tract immune system. In methods for producing food compositions of the present invention, a microorganism that has been evaluated as activating the intestinal tract immune system by the above-described screening method is mixed with a dietarily acceptable carrier. Examples of a dietarily acceptable carrier include stabilizing agents, preservatives, coloring agents and flavoring agents.

Preferred embodiments of the food compositions of the present invention include food and beverage products containing LAB or yeast. Examples of such food and beverage products containing LAB or yeast include dairy products. Examples of the dairy products of the present invention include fermented milk, cheese, and fermented food products (lactobacillus-containing food products, and Kimchi, etc.). These products can be produced by methods known by one skilled in the art.

The food compositions thus produced can be used in the treatment or prevention of diseases, for example, allergies, cancers, and infections as food products having immunostimulatory function (for example, functional food products, health food products, and food for specified health uses).

The present inventors discovered for the first time the involvement of TLRs in intestinal tract immunity. TLRs have also been known to express in cells responsible for innate immunity (for example, macrophages and dendritic cells) (Gordon S. Cell. 111 (2002) 927-930, Akira S. et al., Nature Immunology. 2 (2001) 675-680). Thus, the TLR transfectants of the present invention can be used in the above-described methods of the present invention as models of intestinal immunocompetent cells. In addition, the TLR transfectants of the present invention, along with the other components used in the methods of the present invention, can be used as kits for the methods of the present invention.

The present invention further provides TLR transfectants that can be used in the methods of the present invention, methods for using the TLR transfectants as models of intestinal immunocompetent cells, methods for producing model cells of the intestinal immunocompetent cells, and the model cells produced by such production methods.

BRIEF DESCRIPTION OF THE DRAWINGS

FIG. 1 shows the nucleotide sequence of swine TLR9 cDNA. The signal peptide region is underlined.

FIG. 2 shows the nucleotide sequence of swine TLR9 cDNA (Continuation of FIG. 1).

FIG. 3 shows the nucleotide sequence of swine TLR9 cDNA (Continuation of FIG. 2).

FIG. 4 shows the nucleotide sequence of swine TLR9 cDNA (Continuation of FIG. 3). The transmembrane domain is underlined.

FIG. 6 shows an alignment of TLR9 amino acid sequences.

FIG. 7 shows an alignment of TLR9 amino acid sequences (Continuation of FIG. 6).

FIG. 8 shows an alignment of TLR9 amino acid sequences (Continuation of FIG. 7).

FIG. 9 shows an alignment of TLR9 amino acid sequences (Continuation of FIG. 8).

BEST MODE FOR CARRYING OUT THE INVENTION

Figure 5:
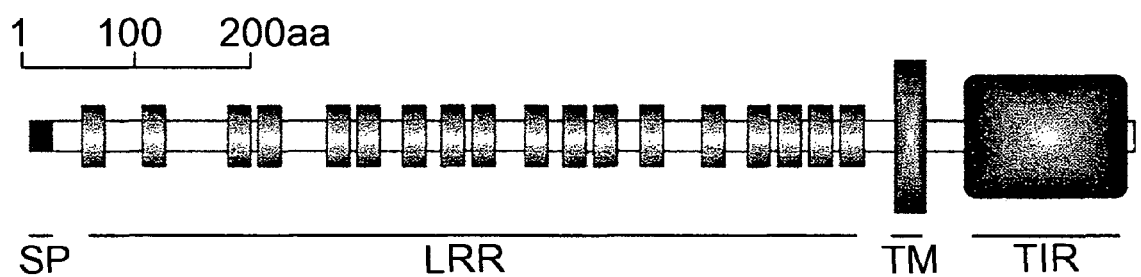
FIG. 5 shows the results of the domain analysis of swine TLR9 by SMART.

Herein below, the present invention will be specifically described using Examples; however, it is not to be construed as being limited thereto.

1) Swine Tissue

Swine tissue was purchased from Funakoshi Co. Ltd.

2) Cloning and Nucleotide Sequencing of Swine TLR9 Gene

Primers were prepared based on the highly conserved region in the gene sequences of human TLR9 and mouse TLR9 published by DDBJ/EMBL/GenBank (Accession Numbers AB045180 and AF348140, respectively). The primers were used in RT-PCR to obtain swine TLR9 fragments from total RNA of the Peyer's patch of swine intestinal tract. The gene fragments were subcloned by ligating into pGEM-T-Easy vector and transfecting E. coli JM109 competent cells with the vector. The DNA sequence was determined using a DNA sequencer Model 4000L (Li-Cor, Lincoln, Nebr., USA). The nucleotide sequence and amino acid sequence were analyzed using GENETYX-SV/RC Ver. 11.0.3.1. The rest of the swine TLR9 gene sequence was obtained by RACE using primers designed from the swine TLR9 gene fragments. The entire TLR9 gene was amplified by PCR and cloned.

3) Preparation of Swine TLR9-Specific Polyclonal Antibody

Results in antigenic determinant (epitope) analysis using GENETYX-SV/RC Ver. 11.0.3.1 and secondary structure analysis of protein showed that the region from amino acids 268 to 284 of swine TLR9 have high antigenicity. We asked Sawady Technologies Co Ltd. for the synthesis of the peptide of that region and preparation of a polyclonal antibody that recognizes the synthetic peptide as antigen.

4) Construction of Swine TLR9 Transfectant

HEK293T (Human Embryonic Kidney) cells, a widely used human cell line for gene introduction, were chosen as the host for introduction of the swine TLR9 gene. Human TLR9-specific primers were used to confirm that HEK293T cells did not express the TLR9 gene. The swine TLR9 gene, excluding the signal peptide, was ligated to pCXN2.1-FLAG gene expression vector (H. Niwa et al., Gene, 108 (1991) 193-199) (courtesy of Dr. Jun-ichi Miyazaki at Osaka University, Graduate School of Medicine, Faculty of Medicine), and HEK293T cells were transfected with the vector by lipofection. Cells that express swine TLR9 were selected on EPICS cell sorter system (BECKMAN COULTER) using antibiotic G418 neomycin (SIGMA).

5) RT-PCR Analysis of Swine TLR9 Expression in the Transfectant

Using TRIzol (Invitrogen), total RNA was extracted from the transfectant. Gene expression of TLR9 mRNA was analyzed by RT-PCR using swine TLR9-specific primers (designed by the present invention), human TLR9-specific primers, and human GAPDH primers (positive control) (K. A. Zarember, P. J. Godowski, J. Immunology, 168 (2002) 554-561).

6) Flow Cytometry and Confocal Laser Microscopy Analyses of Swine TLR9 Expression in the Transfectant The cells were first treated with an anti-FLAG mouse IgG monoclonal antibody (SIGMA) as a primary antibody at 4° C. for 1 hour and then stained with a PerCP-labeled anti-mouse IgG antibody as a secondary antibody at 4° C. for 30 min. The cell nuclei were stained with propidium iodide at 4° C. for 10 min. Analysis was carried out using FACSCalibur™ (JAPAN BECTON DICKINSON). Immunostaining with the swine TLR9 polyclonal antibody is carried out by first treating the cells with the primary antibody mentioned above and subsequently staining with an Alexa 488-labeled anti-rabbit IgG antibody as a secondary antibody at 4° C. for 30 min. The cell nuclei were stained and the cells were analyzed. In addition, the cells were seeded onto type-I collagen-coated disks (IWAKI), treated with a biotin-labeled anti-FLAG mouse IgG antibody (SIGMA) as a primary antibody at 4° C. for 1 hour, and then stained with streptavidin-PE-CyS antibody as a secondary antibody at 4° C. for 30 min. The cell nuclei were stained with propidium iodide at 4° C. for 10 min. Analysis was carried out using a confocal laser microscope (BIO-RAD).

7) Analysis of CpG DNA Uptake using the Transfectant

CpG DNAs used were: CpG2006 derived from E. coli genomic DNA reported to strongly stimulate human immune cells (SEQ ID NO: 9, 5'-TCGTCGTTTTGTCGTTTTGTCGTT-3'); and CpG1826 reported to strongly stimulate mouse immune cells (SEQ ID NO: 10, 5'-TCCATGACGTTCCTGACGTT-3') (S. Pichyangkul et al., J. Immunological Methods, 247 (2001) 83-94). The cells were incubated with 1 M CpG DNA at 37° C. for 1 hour and analyzed using FACSCalibur™ and confocal laser microscope.

8) Real-Time PCR Analysis of TLR9 Expression in Different Swine Tissues.

Total RNA was extracted form different swine tissues (i.e., heart, thymus, lung, spleen, liver, kidney, skeletal muscle, duodenum, jejunum, ileum, ileal Peyer's Patch, and ileal mesenteric lymph node). Using oligo-d(T)$_{18}$ primers, cDNA was synthesized from 1 µg of total RNA and purified. Real-time quantitative PCR was performed on a LightCycler (Roche) using the swine TLR9-specific primers and the purified cDNA. Light Cycler-Fast Start DNA Master SYBR Green (Roche) was used as the reaction kit. The amount of swine TLR9 mRNA was calculated from the ratio of the amount of swine TLR9 gene to the amount of the housekeeping β-actin gene determined from the calibration curve. By setting the expression level of TLR9 in spleen to be 1.000, the amounts of swine TLR9 mRNA in different tissues were compared.

The nucleotide sequences of the primers used in the present invention are summarized in Table 1.

TABLE 1

| sTLR9 gene cloning primers | Forward primers | SEQ ID NO | Reverse primers | SEQ ID NO: |
|---|---|---|---|---|
| sTLR9(2775-3145) | AGACTGGTTACCTGGCAAGA | 11 | GCTATTCDGCDGTDGGAC | 12 |
| sTLR9(2301-2775) | CAACCTGAAAGTCCTAGACG | 13 | GGCAGAAGTTCCGGTTATAG | 14 |
| sTLR9(1708-2347) | AGCTACAACAGCCAGCCCTT | 15 | AGGCGCAGTGCAGAGGGTT | 16 |
| sTLR9(1057-1727) | CTGCGCAAGCTCAACCTGT | 17 | AAGGGCTGGCTGTTGTAGCT | 18 |
| sTLR9(140-1089) | CTGCCTTCCTACCCTGTGA | 19 | GTGGTAATTGAAGGACAGGTT | 20 |
| sTLR9(5'RACE, cDNA synthesis) | | | GCAGTTCCACTTGAGGTTGA | 21 |
| sTLR9(5'RACE, 1st nested PCR) | | | ACGAAGTCAGAGTCGTGCAA | 22 |
| sTLR9(5'RACE, 2nd nested PCR) | | | AGGAAGAGCCAGTTGCAGTT | 23 |
| Primers for analysis of mRNA expression | Forward primers | SEQ ID NO: | Reverse primers | SEQ ID NO: |
| swine TLR9 | CTGAAAGTCTTAGACGTGAG | 24 | TCTTGCCAGGTAACCAGTCT | 25 |
| human TLR9 | GGACCTCTGGTACTGCTTCCA | 26 | AAGCTCGTTGTACACCCAGTCT | 27 |
| human GAPDH | GAAGGTGAAGGTCGGAGTC | 28 | GAAGATGGTGATGGGATTTC | 29 |
| sTLR9 real-time RT-PCR | GTGGAACTGTTTTGGCATC | 30 | CACAGCACTCTGAGCTTTGT | 31 |
| sβ-actin real-time RT-PCR | TGGCATTGTCATGGACTCTG | 32 | AGGGGCGATGATCTTGATCT | 33 |

Example 1

Determination of Swine TLR9 Gene Sequence and its Homology to TLR9s of Other Species In the present invention, the swine TLR9 cDNA sequence determined has 3145 bases (with 54 bases of untranscriptional region at the 5'-end) containing 3090 bases of structural gene (ORF). The ORF encodes 1029 amino acid residues and has a molecular weight of 115.8 kDa (FIGS. 1 to 4). TLR9s of various species were aligned in FIGS. 6 to 9. The amino acid sequence of swine TLR9 had 82.0%, 74.9% and 86.6% homology to human, mouse and cat TLR9s, respectively (Table 2).

TABLE 2

| TLR9 | nucleotide sequence[a] homology (%) | amino acid sequence[a] homology (%) |
|---|---|---|
| human | 84.9 | 82.0 |
| mouse | 78.2 | 74.9 |
| cat | 86.6 | 86.6 |

[a]The sequence information of human, mouse and cat TLR9s can be obtained at DDBJ by accession NOs AB0452180, AF348140 and AY137581, respectively.

Example 2

Expression Analysis of Swine TLR9 Transfectant

Figure 10:
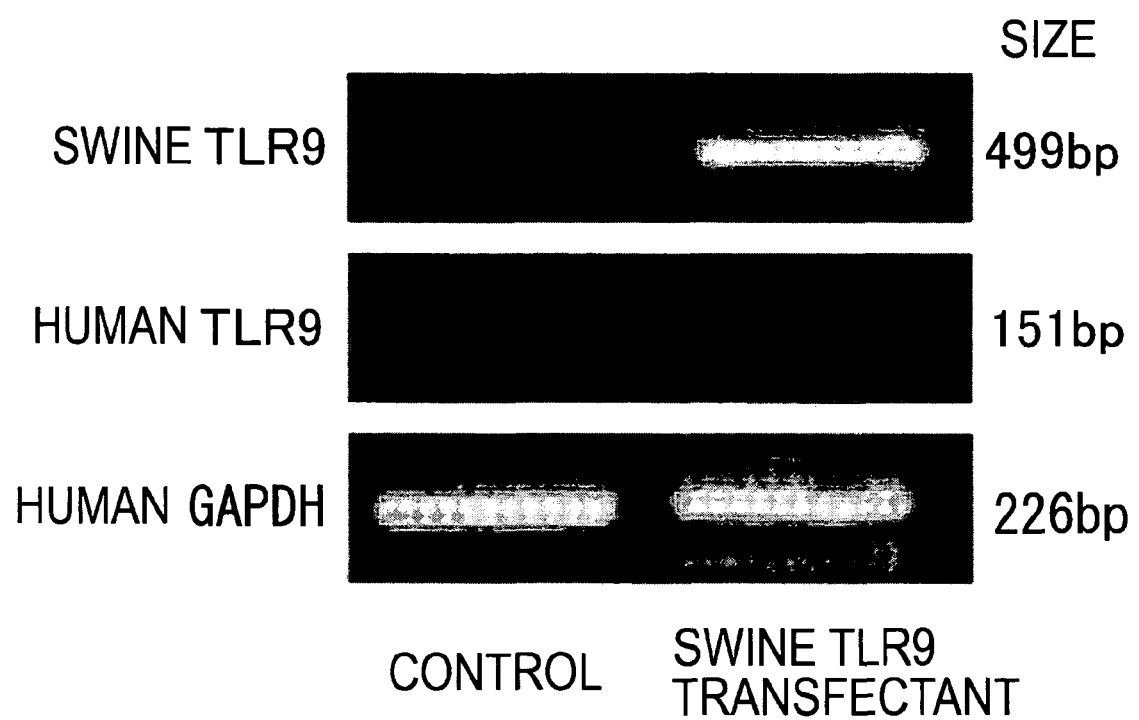
FIG. 10 shows photographs of the expression analysis results of swine TLR9 in transfectant using RT-PCR.

RT-PCT analysis of the expressions of swine TLR9 mRNA and human TLR9 mRNA, using total RNAs obtained from a control cell and the sTLR9 transfectant as templates, revealed strong expression of the swine TLR9 mRNA in the transfectant. Human TLR9 mRNA expression was detected in neither (FIG. 10).

Figure 11:
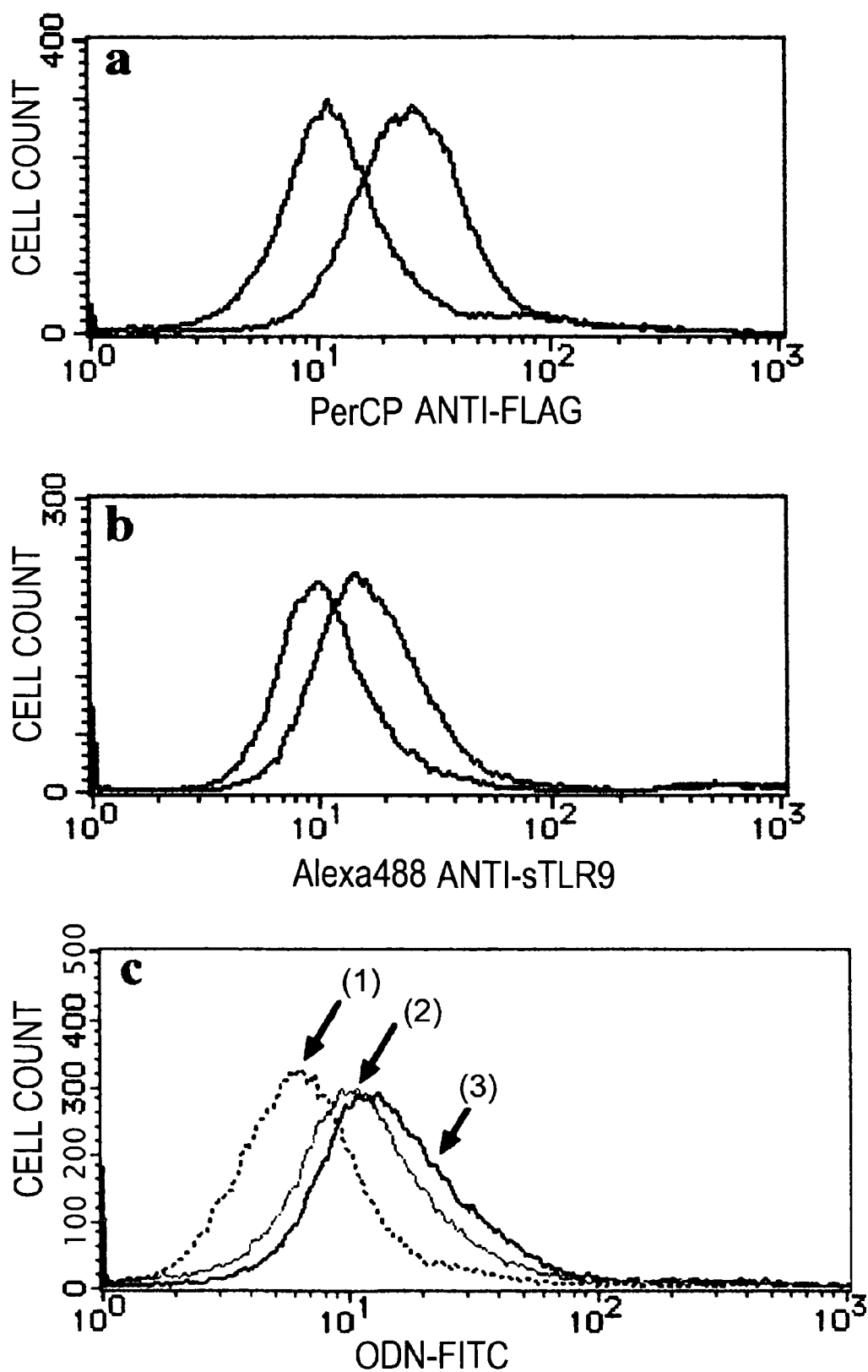
FIG. 11 shows the analysis results of swine TLR9 expression and CpG DNA uptake in transfectant. a: analysis using anti-FLAG antibody. b: analysis using anti-sTLR9 antibody. c: analysis of CpG DNA uptake. Arrow (1) indicates the uptake of CpG1826 and CpG2006 by control cells. Arrow (2) indicates the uptake of CpG1826 in the transfectant. Arrow (3) indicates the uptake of CpG2006 by the transfectant.
Figure 12:
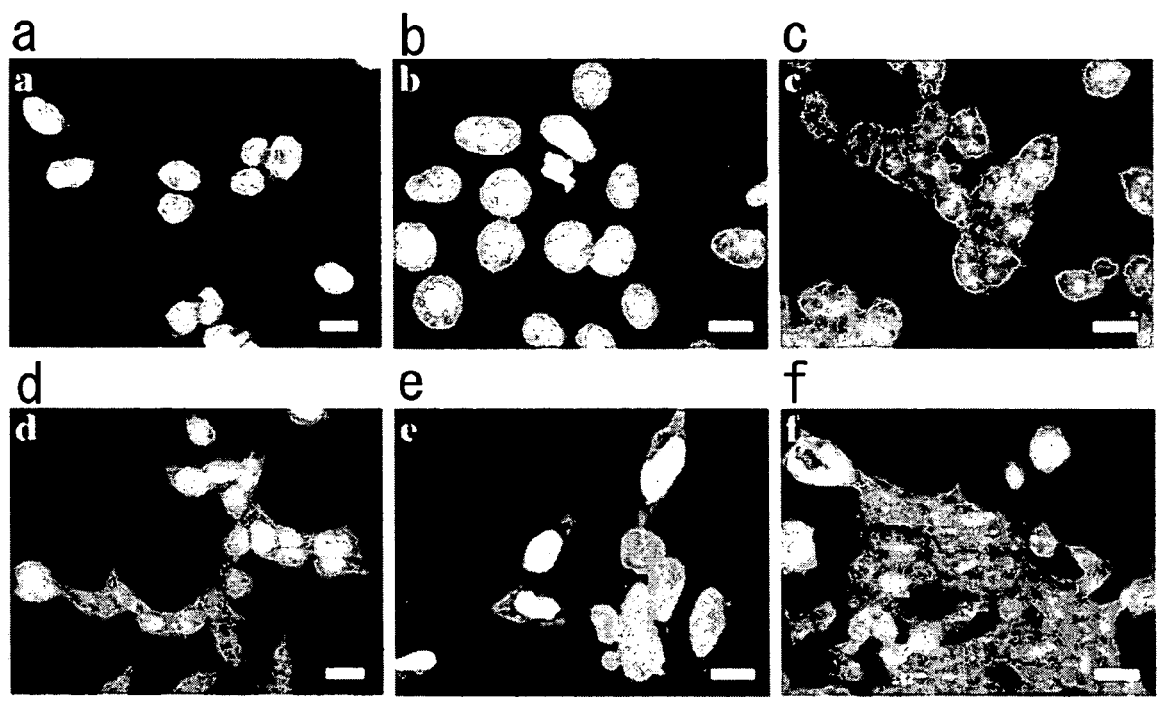
FIG. 12 shows photographs of the analysis results of the transfectants by confocal laser microscopy. a, b, c: control cells; d, e, f: swine TLR9 transfectants. a, d: analysis using anti-FLAG antibody. b, e: analysis using anti-sTLR9 antibody. c, f: analysis of CpG DNA uptake.

When an anti-FLAG antibody was used as the primary antibody, the expression analysis by flow cytometry showed a large shift towards the positive side as compared to the control cell (FIG. 11-a). A shift towards the positive side was also observed for the swine TLR9 antibody (FIG. 11-b). Similarly, the expression was detected by laser microscopy (FIGS. 12-a, c, b and d).

Example 3

Analysis of CpG DNA Uptake

While no significant difference was observed by confocal laser microscopy in the uptake of different CpG DNAs, the flow cytometry of CpG DNA uptake revealed that the swine TLR9 transfectant incorporated relatively larger amounts of human CpG2006 than mouse CpG 1826 (FIGS. 11-c, 12-e and f).

Example 4

Analysis of Swine TLR9 mRNA Expression in Different Tissues

Figure 13:
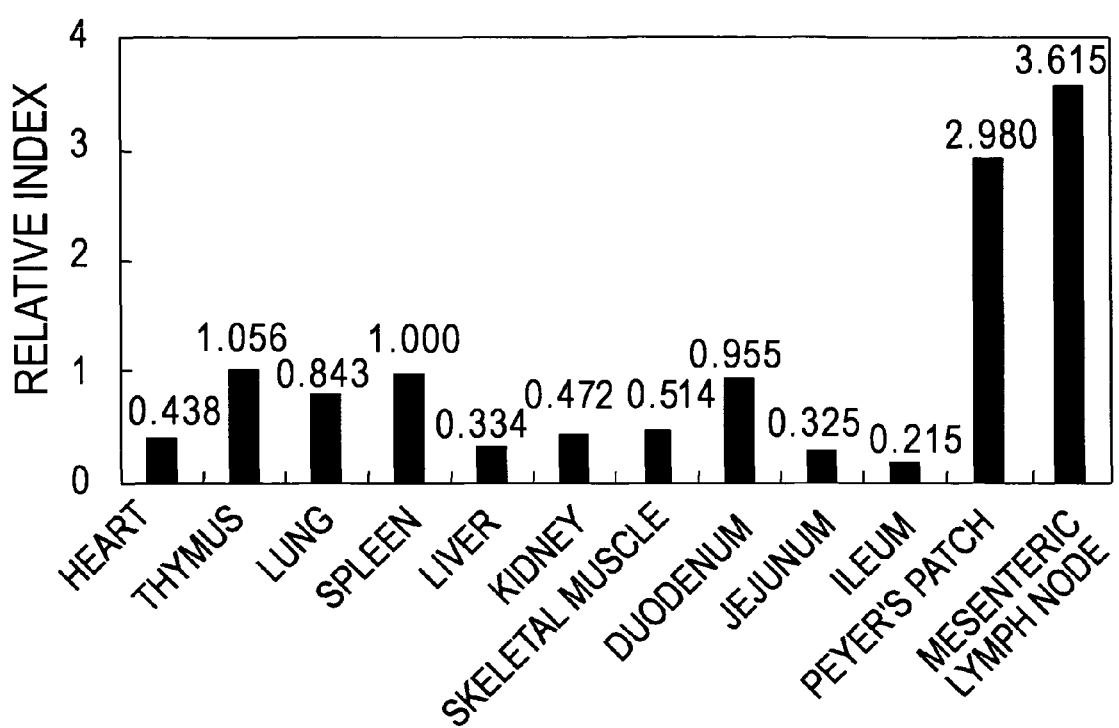
FIG. 13 shows results of the expression analysis of sTLR9 in different tissues using real-time quantitative PCR.

The real-time PCR analysis of swine TLR9 mRNA expression in different tissues showed that swine TLR9 was strongly expressed in the intestinal lymphoid tissue, especially in the Peyer's patch and mesenteric lymph node (FIG. 13).

Examples of the present invention have demonstrated that swine TLR9 has a higher homology to human or cat TLR9 than to mouse TLR9. Previous reports on the expression analysis by real-time PCR indicated that strong expression of TLR9 was observed in spleen. To the contrary, our results prove that the mRNA expression level is about three or more times higher in the Peyer's patches and mesenteric lymph nodes than in spleen. This finding is very interesting in view of the fact that the intestinal mucosal system, which is most likely to be exposed to orally ingested pathogenic bacteria, Peyer's patches and mesenteric lymph nodes play a crucial role in the intestinal immunity. In these Examples, the present inventors have successfully constructed a swine TLR9 transfectant and by using this transfectant in the analysis of CpG DNA uptake, demonstrated that swine TLR9 is more reactive to human CpG DNA than to mouse CpG DNA. These transfectants should serve as a driving force for future analyses of the recognizing ability for the DNA from functional LAB. Through the use of a swine experimental animal as a human model, these transfectants also allow detailed investigation of fundamental studies on the development of functional food products at the molecular level.

Bacterial DNA recognized by TLR9 is known to stimulate macrophages and dendritic cells and promote the production of cytokines and such (M. Bauer et al., J. Immunol. 166 (2001) 5000-5007). The results of these examples are certain to lead to the development of vaccines that take advantage of stimulation by bacterial DNA and recognition by TLR9, as well as of signal transduction systems (R. L. Modlin, Nature 408 (2000) 659-660). Such vaccines can elicit various immune responses, from weak responses that are just enough to prevent infections to highly effective responses that can kill bacteria, and are thus expected to find wide applications in the treatment of tuberculosis and such, as well as cancers, allergies, and such. LAB has recently attracted much attention as an antigen carrier that reaches the intestinal tract alive. In addition to that, the DNA of LAB is shown to have immunostimulatory ability by the present invention and this has substantially raised the expectation of LAB. The present invention has demonstrated strong expression of TLR9 in the Peyer's patches and mesenteric lymph nodes—a strong indication of the important role of TLR9 in the intestinal tract immune system and an implication that the DNAs of intestinal LAB and dietary dairy LAB can stimulate TLR9 and thus activate the immune system. Thus, understanding the TLR9-mediated intestinal tract immune system by LAB DNA is a task that must be accomplished for developing DNA vaccines using intestinal indigenous LAB and dairy LAB.

The strong expression of TLR9 in the Peyer's patches and mesenteric lymph nodes may suggest significant development of an innate immune system in intestinal tract immunity. The intestinal tract immune system has recently received great attention in medical and immunological fields as a critical area of study. Nonetheless, intestinal tract immunity as a field of study is relatively new and little is known about its fundamental mechanisms. Thus, there is much to expect from understanding the mechanisms of the intestinal tract immune system.

The findings of the present invention provide clues to understanding the molecular mechanism of TLR9-mediated recognition in the signal transduction pathways of intestinal tract and serve as a driving force to promote the progress in understanding the innate immunity—a basic immune system.

INDUSTRIAL APPLICABILITY

The present invention provides uses of TLR transfectants. The TLR transfectants can be used as model cells of intestinal immunocompetent cells. By using the TLR transfectants, samples and microorganisms that activate the intestinal tract immune system can be identified, and pharmaceutical compositions and food compositions that activate the intestinal tract immune system can be produced. The samples, microorganisms, pharmaceutical compositions and food compositions can be used in the treatment or prevention of diseases, for example, allergies, cancers, and infections.

The invention claimed is:

1. A method of screening for a sample that activates the intestinal tract immune system, comprising the steps of:
   (a) contacting a test sample with an isolated cell expressing a Toll-like receptor 9 (TLR9) encoded by a DNA comprising the nucleotide sequence shown in SEQ ID NO: 1;
   (b) measuring activity of the TLR9 using signal transduction in the cell as an indicator; and
   (c) selecting the test sample as a sample that activates the intestinal tract immune system if the activity of the TLR9 is increased as compared to activity of the TLR9 in a cell not contacted with the test sample.

2. A method for producing a pharmaceutical composition that activates the intestinal tract immune system, comprising the steps of claim 1, and a further step of mixing the sample selected as a sample that activates the intestinal tract immune system with a pharmaceutically acceptable carrier.

3. A method of screening for microorganisms that activate the intestinal tract immune system, comprising the steps of:
   (a) preparing an extract from a test microorganism;
   (b) contacting the extract with an isolated cell expressing a Toll-like receptor 9 (TLR9) encoded by a DNA comprising the nucleotide sequence shown in SEQ ID NO: 1;
   (c) measuring activity of the TLR9 using signal transduction in the cell as an indicator; and
   (d) selecting the test microorganism as a microorganism that activates the intestinal tract immune system if the activity of the TLR9 is increased as compared to activity of the TLR9 in a cell not contacted with the extract.

4. A method for producing a food composition that activates the intestinal tract immune system, comprising the steps of claim 3, and then mixing the microorganism selected in part (d) of claim 3 with a dietarily acceptable carrier.

5. The method of claim 4, wherein the microorganism is a lactic acid bacterium.

6. The method, according to claim 4, wherein the dietarily acceptable carrier is a dairy product.

* * * * *

SEQUENCE LISTING

<160> NUMBER OF SEQ ID NOS: 33

<210> SEQ ID NO 1
<211> LENGTH: 3329
<212> TYPE: DNA
<213> ORGANISM: Sus scrofa
<220> FEATURE:
<221> NAME/KEY: CDS
<222> LOCATION: (55)..(3147)
<223> OTHER INFORMATION:

<400> SEQUENCE: 1

```
agctgcggcc cggtctgcca gccagaccct ttggagaaga ccccactccc tgtc atg          57
                                                              Met
                                                              1 ggc ccc cgc tgc acc ctg cac ccc ctt tct ctc ctg gtg cag gtg aca         105
Gly Pro Arg Cys Thr Leu His Pro Leu Ser Leu Leu Val Gln Val Thr
        5                  10                  15 gcg ctg gct gcg act ctg gcc cag ggc agg ctg cct gcc ttc ctg ccc         153
Ala Leu Ala Ala Thr Leu Ala Gln Gly Arg Leu Pro Ala Phe Leu Pro
     20                  25                  30 tgt gag ctc cag ccc cac ggc ctg gtg aac tgc aac tgg ctc ttc ctg         201
Cys Glu Leu Gln Pro His Gly Leu Val Asn Cys Asn Trp Leu Phe Leu
 35                  40                  45 aag tcc gtg ccc cac ttc tcg gcg gca gcg ccc cgg gcc aac gtc acc         249
Lys Ser Val Pro His Phe Ser Ala Ala Ala Pro Arg Ala Asn Val Thr
 50                  55                  60                  65 agc ctc tcc tta ctc tcc aac cgc atc cac cac ttg cac gac tct gac         297
Ser Leu Ser Leu Leu Ser Asn Arg Ile His His Leu His Asp Ser Asp
                 70                  75                  80 ttc gtc cac ctg tcc agc cta cga act ctc aac ctc aag tgg aac tgc         345
Phe Val His Leu Ser Ser Leu Arg Thr Leu Asn Leu Lys Trp Asn Cys
             85                  90                  95 ccg ccg gct ggc ctc agc ccc atg cac ttc ccc tgc cac atg acc atc         393
Pro Pro Ala Gly Leu Ser Pro Met His Phe Pro Cys His Met Thr Ile
        100                 105                 110 gag ccc aac acc ttc ctg gcc gtg ccc acc ctg gag gag ctg aac ctg         441
Glu Pro Asn Thr Phe Leu Ala Val Pro Thr Leu Glu Glu Leu Asn Leu
    115                 120                 125 agc tac aac agc atc acg acc gtg cct gcc ctg ccc gac tcc ctc gtg         489
Ser Tyr Asn Ser Ile Thr Thr Val Pro Ala Leu Pro Asp Ser Leu Val
130                 135                 140                 145 tcc ctg tcg ctg agc cgc acc aac atc ctg gtg cta gac ccc acc cac         537
Ser Leu Ser Leu Ser Arg Thr Asn Ile Leu Val Leu Asp Pro Thr His
                150                 155                 160 ctc act ggc cta cat gcc ctg cgc tac ctg tac atg gat ggc aac tgc         585
Leu Thr Gly Leu His Ala Leu Arg Tyr Leu Tyr Met Asp Gly Asn Cys
            165                 170                 175 tac tac aag aac ccc tgc cag ggg gcg ctg gag gtg gtg ccg ggt gcc         633
Tyr Tyr Lys Asn Pro Cys Gln Gly Ala Leu Glu Val Val Pro Gly Ala
        180                 185                 190 ctc ctc ggc ctg ggc aac ctc aca cat ctc tca ctc aag tac aac aat         681
Leu Leu Gly Leu Gly Asn Leu Thr His Leu Ser Leu Lys Tyr Asn Asn
    195                 200                 205 ctc acg gag gtg ccc cgc agc ctg ccc ccc agc ctg gag acc ctg ctg         729
Leu Thr Glu Val Pro Arg Ser Leu Pro Pro Ser Leu Glu Thr Leu Leu
210                 215                 220                 225 ttg tcc tac aac cac att gtc acc ctg acg cct gag gac ctg gcc aat         777
Leu Ser Tyr Asn His Ile Val Thr Leu Thr Pro Glu Asp Leu Ala Asn
                230                 235                 240
```

-continued

| | | |
|---|---|---|
| ctg act gcc ctg cgc gtg ctt gat gtg ggg ggg aac tgc cgc cgc tgt<br>Leu Thr Ala Leu Arg Val Leu Asp Val Gly Gly Asn Cys Arg Arg Cys<br>245 250 255 | 825 | |
| gac cat gcc cgc aac ccc tgc agg gag tgc cca aag gac cac ccc aag<br>Asp His Ala Arg Asn Pro Cys Arg Glu Cys Pro Lys Asp His Pro Lys<br>260 265 270 | 873 | |
| ctg cac tct gac acc ttc agc cac ctg agc cgc ctc gaa ggc ctg gtg<br>Leu His Ser Asp Thr Phe Ser His Leu Ser Arg Leu Glu Gly Leu Val<br>275 280 285 | 921 | |
| ttg aaa gac agt tct ctc tac aac ctg gac gcc agg tgg ttc cga ggc<br>Leu Lys Asp Ser Ser Leu Tyr Asn Leu Asp Ala Arg Trp Phe Arg Gly<br>290 295 300 305 | 969 | |
| ctg gac agg ctc caa gtg ctg gac ctg agt gag aac ttc ctc tac gac<br>Leu Asp Arg Leu Gln Val Leu Asp Leu Ser Glu Asn Phe Leu Tyr Asp<br>310 315 320 | 1017 | |
| tgc atc acc aag acc acg gcc ttc cag ggc ctg gcc cga ctg cgc aag<br>Cys Ile Thr Lys Thr Thr Ala Phe Gln Gly Leu Ala Arg Leu Arg Lys<br>325 330 335 | 1065 | |
| ctc aac ctg tcc ttc aat tac cac aag aag gtg tcc ttt gcc cac ctg<br>Leu Asn Leu Ser Phe Asn Tyr His Lys Lys Val Ser Phe Ala His Leu<br>340 345 350 | 1113 | |
| cac ctg gca ccc tcc ttt ggg cac ctc cgg tcc ctg aag gag ctg gac<br>His Leu Ala Pro Ser Phe Gly His Leu Arg Ser Leu Lys Glu Leu Asp<br>355 360 365 | 1161 | |
| atg cat ggc atc ttc ttc cgc tcg ctc agt gag acc acg ctc caa cct<br>Met His Gly Ile Phe Phe Arg Ser Leu Ser Glu Thr Thr Leu Gln Pro<br>370 375 380 385 | 1209 | |
| ctg gtc caa ctg cct atg ctc cag acc ctg cgc ctg cag atg aac ttc<br>Leu Val Gln Leu Pro Met Leu Gln Thr Leu Arg Leu Gln Met Asn Phe<br>390 395 400 | 1257 | |
| att aac cag gcc cag ctc agc atc ttt ggg gcc ttc cct ggc ctg ctg<br>Ile Asn Gln Ala Gln Leu Ser Ile Phe Gly Ala Phe Pro Gly Leu Leu<br>405 410 415 | 1305 | |
| tac gtg gac cta tcg gac aac cgc atc agc gga gct gca agg cca gtg<br>Tyr Val Asp Leu Ser Asp Asn Arg Ile Ser Gly Ala Ala Arg Pro Val<br>420 425 430 | 1353 | |
| gcc att act agg gag gtg gat ggt agg gag agg gtc tgg ctg cct tcc<br>Ala Ile Thr Arg Glu Val Asp Gly Arg Glu Arg Val Trp Leu Pro Ser<br>435 440 445 | 1401 | |
| agg aac ctc gct cca cgt cca ctg gac act ctc cgc tca gag gac ttc<br>Arg Asn Leu Ala Pro Arg Pro Leu Asp Thr Leu Arg Ser Glu Asp Phe<br>450 455 460 465 | 1449 | |
| atg cca aac tgc aag gcc ttc agc ttc acc ttg gac ctg tct cgg aac<br>Met Pro Asn Cys Lys Ala Phe Ser Phe Thr Leu Asp Leu Ser Arg Asn<br>470 475 480 | 1497 | |
| aac ctg gtg aca atc cag tcg gag atg ttt gct cgc ctc tca cgc ctc<br>Asn Leu Val Thr Ile Gln Ser Glu Met Phe Ala Arg Leu Ser Arg Leu<br>485 490 495 | 1545 | |
| gag tgc ctg cgt ctg agc cac aac agc atc tcc cag gcg gtc aat ggc<br>Glu Cys Leu Arg Leu Ser His Asn Ser Ile Ser Gln Ala Val Asn Gly<br>500 505 510 | 1593 | |
| tct cag ttt gtg ccg ctg acc agc ctg cgg gtg ctg gac ctg tcc cac<br>Ser Gln Phe Val Pro Leu Thr Ser Leu Arg Val Leu Asp Leu Ser His<br>515 520 525 | 1641 | |
| aac aag ctg gac ctg tat cac ggg cgc tcg ttc acg gag ctg ccg cgc<br>Asn Lys Leu Asp Leu Tyr His Gly Arg Ser Phe Thr Glu Leu Pro Arg<br>530 535 540 545 | 1689 | |
| ctg gaa gca ctg gac ctc agc tac aac agc cag ccc ttt acc atg cag<br>Leu Glu Ala Leu Asp Leu Ser Tyr Asn Ser Gln Pro Phe Thr Met Gln<br>550 555 560 | 1737 | |

|  |  |
|---|---|
| ggt gtg ggc cac aac ctc agc ttc gtg gcc cag ctg ccc gcc ctg cgc<br>Gly Val Gly His Asn Leu Ser Phe Val Ala Gln Leu Pro Ala Leu Arg<br>               565                        570                      575 | 1785 |
| tac ctc agc ctg gcg cac aat gac atc cat agc cga gtg tcc cag cag<br>Tyr Leu Ser Leu Ala His Asn Asp Ile His Ser Arg Val Ser Gln Gln<br>       580                        585                        590 | 1833 |
| ctc tgt agc gcc tca ctg tgc gcc ctg gac ttt agc ggc aac gat ctg<br>Leu Cys Ser Ala Ser Leu Cys Ala Leu Asp Phe Ser Gly Asn Asp Leu<br>               595                        600                      605 | 1881 |
| agc cgg atg tgg gct gag gga gac ctc tat ctc cgc ttc ttc caa ggc<br>Ser Arg Met Trp Ala Glu Gly Asp Leu Tyr Leu Arg Phe Phe Gln Gly<br>610                        615                        620                      625 | 1929 |
| cta aga agc cta gtc tgg ctg gac ctg tcc cag aac cac ctg cac acc<br>Leu Arg Ser Leu Val Trp Leu Asp Leu Ser Gln Asn His Leu His Thr<br>                             630                        635                      640 | 1977 |
| ctc ctg cca cgt gcc ctg gac aac ctc ccc aaa agc ctg aag cat ctg<br>Leu Leu Pro Arg Ala Leu Asp Asn Leu Pro Lys Ser Leu Lys His Leu<br>               645                        650                      655 | 2025 |
| cat ctc cgt gac aat aac ctg gcc ttc ttc aac tgg agc agc ctg acc<br>His Leu Arg Asp Asn Asn Leu Ala Phe Phe Asn Trp Ser Ser Leu Thr<br>                 660                       665                   670 | 2073 |
| ctc ctg ccc aag ctg gaa acc ctg gac ttg gct gga aac cag ctg aag<br>Leu Leu Pro Lys Leu Glu Thr Leu Asp Leu Ala Gly Asn Gln Leu Lys<br>               675                       680                      685 | 2121 |
| gcc cta agc aat ggc agc ctg cca tct ggc acc cag ctg cgg agg ctg<br>Ala Leu Ser Asn Gly Ser Leu Pro Ser Gly Thr Gln Leu Arg Arg Leu<br>690                        695                        700                      705 | 2169 |
| gac ctc agt ggc aac agc atc ggc ttt gtg aac cct ggc ttc ttt gcc<br>Asp Leu Ser Gly Asn Ser Ile Gly Phe Val Asn Pro Gly Phe Phe Ala<br>                       710                       715                   720 | 2217 |
| ctg gcc aag cag tta gaa gag ctc aac ctc agc gcc aat gcc ctc aag<br>Leu Ala Lys Gln Leu Glu Glu Leu Asn Leu Ser Ala Asn Ala Leu Lys<br>               725                        730                      735 | 2265 |
| aca gtg gag ccc tcc tgg ttt ggc tcg atg gtg ggc aac ctg aaa gtc<br>Thr Val Glu Pro Ser Trp Phe Gly Ser Met Val Gly Asn Leu Lys Val<br>               740                        745                   750 | 2313 |
| cta gac gtg agc gcc aac cct ctg cac tgc gcc tgt ggg gcg acc ttc<br>Leu Asp Val Ser Ala Asn Pro Leu His Cys Ala Cys Gly Ala Thr Phe<br>755                        760                        765 | 2361 |
| gtg ggc ttc ctg ctg gag gta cag gct gcc gtg cct ggg ctg ccc agc<br>Val Gly Phe Leu Leu Glu Val Gln Ala Ala Val Pro Gly Leu Pro Ser<br>770                        775                        780                      785 | 2409 |
| cgc gtc aag tgt ggc agt ccg ggg cag ctc cag ggc cat agc atc ttt<br>Arg Val Lys Cys Gly Ser Pro Gly Gln Leu Gln Gly His Ser Ile Phe<br>               790                       795                      800 | 2457 |
| gcg caa gac ctg cgc ctc tgc ctg gat gag acc ctc tcg tgg aac tgt<br>Ala Gln Asp Leu Arg Leu Cys Leu Asp Glu Thr Leu Ser Trp Asn Cys<br>               805                        810                      815 | 2505 |
| ttt ggc atc tcg ctg ctg gcc atg gcc ctg ggc ctg gtt gtg ccc atg<br>Phe Gly Ile Ser Leu Leu Ala Met Ala Leu Gly Leu Val Val Pro Met<br>820                        825                        830 | 2553 |
| ctg cac cac ctc tgc ggc tgg gac ctc tgg tac tgc ttc cac ctg tgc<br>Leu His His Leu Cys Gly Trp Asp Leu Trp Tyr Cys Phe His Leu Cys<br>               835                       840                      845 | 2601 |
| ctg gcc tgg ctg ccc cac cga ggg cag cgg cgg ggc gca gac gcc ctg<br>Leu Ala Trp Leu Pro His Arg Gly Gln Arg Arg Gly Ala Asp Ala Leu<br>850                        855                        860                      865 | 2649 |
| ttc tat gat gcc ttc gtg gtc ttt gac aaa gct cag agt gct gtg gcc<br>Phe Tyr Asp Ala Phe Val Val Phe Asp Lys Ala Gln Ser Ala Val Ala<br>                 870                       875                      880 | 2697 |

```
gac tgg gtg tac aac gag ctg cgg gtg cag ctg gag gag cgc cgt ggg    2745
Asp Trp Val Tyr Asn Glu Leu Arg Val Gln Leu Glu Glu Arg Arg Gly
            885                 890                 895 cgc cgc gca ctg cgc ctg tgc ctg gag gag cga gac tgg tta cct ggc    2793
Arg Arg Ala Leu Arg Leu Cys Leu Glu Glu Arg Asp Trp Leu Pro Gly
        900                 905                 910 aag acg ctc ttc gag aac ctg tgg gcc tca gtc tac agc agc cgc aag    2841
Lys Thr Leu Phe Glu Asn Leu Trp Ala Ser Val Tyr Ser Ser Arg Lys
    915                 920                 925 acc ctg ttt gtg ctg gcc cac acg gac cgt gtc agc ggc ctc ttg cgt    2889
Thr Leu Phe Val Leu Ala His Thr Asp Arg Val Ser Gly Leu Leu Arg
930                 935                 940                 945 gcc agt ttc ctg ctg gcc cag cag cgc ctg ctg gag gac cgc aag gac    2937
Ala Ser Phe Leu Leu Ala Gln Gln Arg Leu Leu Glu Asp Arg Lys Asp
            950                 955                 960 gtt gta gtg ctg gtg atc ctg cgc ccc gat gcc tac cgc tcc cgc tac    2985
Val Val Val Leu Val Ile Leu Arg Pro Asp Ala Tyr Arg Ser Arg Tyr
        965                 970                 975 gtg cgg ctg cgc cag cgc ctc tgc cgc cag agt gtc ctc ctc tgg ccc    3033
Val Arg Leu Arg Gln Arg Leu Cys Arg Gln Ser Val Leu Leu Trp Pro
    980                 985                 990 cac cag ccc cgt ggg cag ggc  agc ttc tgg gcc cag  ctg ggc aca gcc  3081
His Gln Pro Arg Gly Gln Gly  Ser Phe Trp Ala Gln  Leu Gly Thr Ala
995                 1000                 1005 ctg  acc agg gac aac cgc  cac ttc tat aac cgg  aac ttc tgc cgg     3126
Leu  Thr Arg Asp Asn Arg  His Phe Tyr Asn Arg  Asn Phe Cys Arg
1010                 1015                 1020 ggc  ccc acg aca gcc gaa  tag cactgagtga cagcccagtt gccccagccc     3177
Gly  Pro Thr Thr Ala Glu
1025                 1030 ccctggatttt gcctctctgc ctgggtgccc aacctgctt tgctcagcca caccactgct    3237
ctgctccctg ttccccaccc caccccccag cctggcatgt aacatgtgcc aataaatgc     3297 taccggaggc caagcaaaaa aaaaaaaaaa aa                                  3329

<210> SEQ ID NO 2
<211> LENGTH: 1030
<212> TYPE: PRT
<213> ORGANISM: Sus scrofa

<400> SEQUENCE: 2

Met Gly Pro Arg Cys Thr Leu His Pro Leu Ser Leu Val Gln Val
1               5                   10                  15

Thr Ala Leu Ala Ala Thr Leu Ala Gln Gly Arg Leu Pro Ala Phe Leu
            20                  25                  30

Pro Cys Glu Leu Gln Pro His Gly Leu Val Asn Cys Asn Trp Leu Phe
        35                  40                  45

Leu Lys Ser Val Pro His Phe Ser Ala Ala Pro Arg Ala Asn Val
    50                  55                  60

Thr Ser Leu Ser Leu Leu Ser Asn Arg Ile His His Leu His Asp Ser
65                  70                  75                  80

Asp Phe Val His Leu Ser Ser Leu Arg Thr Leu Asn Leu Lys Trp Asn
            85                  90                  95

Cys Pro Pro Ala Gly Leu Ser Pro Met His Phe Pro Cys His Met Thr
        100                 105                 110

Ile Glu Pro Asn Thr Phe Leu Ala Val Pro Thr Leu Glu Glu Leu Asn
    115                 120                 125

Leu Ser Tyr Asn Ser Ile Thr Thr Val Pro Ala Leu Pro Asp Ser Leu
130                 135                 140
```

-continued

Val Ser Leu Ser Leu Ser Arg Thr Asn Ile Leu Val Leu Asp Pro Thr
145                 150                 155                 160

His Leu Thr Gly Leu His Ala Leu Arg Tyr Leu Tyr Met Asp Gly Asn
            165                 170                 175

Cys Tyr Tyr Lys Asn Pro Cys Gln Gly Ala Leu Glu Val Val Pro Gly
        180                 185                 190

Ala Leu Leu Gly Leu Gly Asn Leu Thr His Leu Ser Leu Lys Tyr Asn
    195                 200                 205

Asn Leu Thr Glu Val Pro Arg Ser Leu Pro Pro Ser Leu Glu Thr Leu
210                 215                 220

Leu Leu Ser Tyr Asn His Ile Val Thr Leu Thr Pro Glu Asp Leu Ala
225                 230                 235                 240

Asn Leu Thr Ala Leu Arg Val Leu Asp Val Gly Gly Asn Cys Arg Arg
            245                 250                 255

Cys Asp His Ala Arg Asn Pro Cys Arg Glu Cys Pro Lys Asp His Pro
        260                 265                 270

Lys Leu His Ser Asp Thr Phe Ser His Leu Ser Arg Leu Glu Gly Leu
    275                 280                 285

Val Leu Lys Asp Ser Ser Leu Tyr Asn Leu Asp Ala Arg Trp Phe Arg
290                 295                 300

Gly Leu Asp Arg Leu Gln Val Leu Asp Leu Ser Glu Asn Phe Leu Tyr
305                 310                 315                 320

Asp Cys Ile Thr Lys Thr Thr Ala Phe Gln Gly Leu Ala Arg Leu Arg
            325                 330                 335

Lys Leu Asn Leu Ser Phe Asn Tyr His Lys Lys Val Ser Phe Ala His
        340                 345                 350

Leu His Leu Ala Pro Ser Phe Gly His Leu Arg Ser Leu Lys Glu Leu
    355                 360                 365

Asp Met His Gly Ile Phe Phe Arg Ser Leu Ser Glu Thr Thr Leu Gln
370                 375                 380

Pro Leu Val Gln Leu Pro Met Leu Gln Thr Leu Arg Leu Gln Met Asn
385                 390                 395                 400

Phe Ile Asn Gln Ala Gln Leu Ser Ile Phe Gly Ala Phe Pro Gly Leu
            405                 410                 415

Leu Tyr Val Asp Leu Ser Asp Asn Arg Ile Ser Gly Ala Ala Arg Pro
        420                 425                 430

Val Ala Ile Thr Arg Glu Val Asp Gly Arg Glu Arg Val Trp Leu Pro
    435                 440                 445

Ser Arg Asn Leu Ala Pro Arg Pro Leu Asp Thr Leu Arg Ser Glu Asp
450                 455                 460

Phe Met Pro Asn Cys Lys Ala Phe Ser Phe Thr Leu Asp Leu Ser Arg
465                 470                 475                 480

Asn Asn Leu Val Thr Ile Gln Ser Glu Met Phe Ala Arg Leu Ser Arg
            485                 490                 495

Leu Glu Cys Leu Arg Leu Ser His Asn Ser Ile Ser Gln Ala Val Asn
        500                 505                 510

Gly Ser Gln Phe Val Pro Leu Thr Ser Leu Arg Val Leu Asp Leu Ser
    515                 520                 525

His Asn Lys Leu Asp Leu Tyr His Gly Arg Ser Phe Thr Glu Leu Pro
530                 535                 540

Arg Leu Glu Ala Leu Asp Leu Ser Tyr Asn Ser Gln Pro Phe Thr Met
545                 550                 555                 560

Gln Gly Val Gly His Asn Leu Ser Phe Val Ala Gln Leu Pro Ala Leu

```
                565                 570                 575
Arg Tyr Leu Ser Leu Ala His Asn Asp Ile His Ser Arg Val Ser Gln
            580                 585                 590
Gln Leu Cys Ser Ala Ser Leu Cys Ala Leu Asp Phe Ser Gly Asn Asp
            595                 600                 605
Leu Ser Arg Met Trp Ala Glu Gly Asp Leu Tyr Leu Arg Phe Phe Gln
            610                 615                 620
Gly Leu Arg Ser Leu Val Trp Leu Asp Leu Ser Gln Asn His Leu His
625                 630                 635                 640
Thr Leu Leu Pro Arg Ala Leu Asp Asn Leu Pro Lys Ser Leu Lys His
                645                 650                 655
Leu His Leu Arg Asp Asn Asn Leu Ala Phe Phe Asn Trp Ser Ser Leu
                660                 665                 670
Thr Leu Leu Pro Lys Leu Glu Thr Leu Asp Leu Ala Gly Asn Gln Leu
                675                 680                 685
Lys Ala Leu Ser Asn Gly Ser Leu Pro Ser Gly Thr Gln Leu Arg Arg
            690                 695                 700
Leu Asp Leu Ser Gly Asn Ser Ile Gly Phe Val Asn Pro Gly Phe Phe
705                 710                 715                 720
Ala Leu Ala Lys Gln Leu Glu Leu Asn Leu Ser Ala Asn Ala Leu
                725                 730                 735
Lys Thr Val Glu Pro Ser Trp Phe Ser Met Val Gly Asn Leu Lys
                740                 745                 750
Val Leu Asp Val Ser Ala Asn Pro Leu His Cys Ala Cys Gly Ala Thr
                755                 760                 765
Phe Val Gly Phe Leu Leu Glu Val Gln Ala Ala Val Pro Gly Leu Pro
            770                 775                 780
Ser Arg Val Lys Cys Gly Ser Pro Gly Gln Leu Gln Gly His Ser Ile
785                 790                 795                 800
Phe Ala Gln Asp Leu Arg Leu Cys Leu Asp Glu Thr Leu Ser Trp Asn
                805                 810                 815
Cys Phe Gly Ile Ser Leu Leu Ala Met Ala Leu Gly Leu Val Val Pro
                820                 825                 830
Met Leu His His Leu Cys Gly Trp Asp Leu Trp Tyr Cys Phe His Leu
                835                 840                 845
Cys Leu Ala Trp Leu Pro His Arg Gly Gln Arg Arg Gly Ala Asp Ala
            850                 855                 860
Leu Phe Tyr Asp Ala Phe Val Phe Asp Lys Ala Gln Ser Ala Val
865                 870                 875                 880
Ala Asp Trp Val Tyr Asn Glu Leu Arg Val Gln Leu Glu Glu Arg Arg
                885                 890                 895
Gly Arg Arg Ala Leu Arg Leu Cys Leu Glu Glu Arg Asp Trp Leu Pro
            900                 905                 910
Gly Lys Thr Leu Phe Glu Asn Leu Trp Ala Ser Val Tyr Ser Ser Arg
            915                 920                 925
Lys Thr Leu Phe Val Leu Ala His Thr Asp Arg Val Ser Gly Leu Leu
            930                 935                 940
Arg Ala Ser Phe Leu Leu Ala Gln Gln Arg Leu Leu Glu Asp Arg Lys
945                 950                 955                 960
Asp Val Val Val Leu Val Ile Leu Arg Pro Asp Ala Tyr Arg Ser Arg
                965                 970                 975
Tyr Val Arg Leu Arg Gln Arg Leu Cys Arg Gln Ser Val Leu Leu Trp
            980                 985                 990
```

```
                Pro His Gln Pro Arg Gly Gln Gly  Ser Phe Trp Ala Gln  Leu Gly Thr
                         995                 1000                    1005

Ala Leu  Thr Arg Asp Asn Arg  His Phe Tyr Asn Arg  Asn Phe Cys
                    1010                 1015                 1020

Arg Gly  Pro Thr Thr Ala Glu
                    1025                 1030

<210> SEQ ID NO 3
<211> LENGTH: 3868
<212> TYPE: DNA
<213> ORGANISM: Homo sapiens
<220> FEATURE:
<221> NAME/KEY: CDS
<222> LOCATION: (635)..(3733)
<223> OTHER INFORMATION:

<400> SEQUENCE: 3
ggaggtcttg tttccggaag atgttgcaag gctgtggtga aggcaggtgc agcctagcct        60
cctgctcaag ctacaccctg gccctccacg catgaggccc tgcagaactc tggagatggt      120
gcctacaagg gcagaaaagg acaagtcggc agccgctgtc ctgagggcac cagctgtggt      180
gcaggagcca agacctgagg gtggaagtgt cctcttagaa tggggagtgc ccagcaaggt      240 gtaccgcta ctggtgctat ccagaattcc catctctccc tgctctctgc ctgagctctg      300
ggccttagct cctcccgggg cttggtgagg acaggtgtg aggccctcat gggatgtagg      360
ctgtctgaga ggggagtgga agaggaagg ggtgaaggag ctgtctgcca tttgactatg      420
caaatggcct ttgactcatg ggaccctgtc ctcctcactg ggggcagggt ggagtggagg      480
gggagctact aggctggtat aaaaatctta cttcctctat tctctgagcc gctgctgccc      540
ctgtgggaag ggacctcgag tgtgaagcat ccttccctgt agctgctgtc cagtctgccc      600
gccagaccct ctggagaagc ccctgccccc cagc atg ggt ttc tgc cgc agc gcc     655
                                     Met Gly Phe Cys Arg Ser Ala
                                       1               5 ctg cac ccg ctg tct ctc ctg gtg cag gcc atc atg ctg gcc atg acc        703
Leu His Pro Leu Ser Leu Leu Val Gln Ala Ile Met Leu Ala Met Thr
         10                  15                  20 ctg gcc ctg ggt acc ttg cct gcc ttc cta ccc tgt gag ctc cag ccc        751
Leu Ala Leu Gly Thr Leu Pro Ala Phe Leu Pro Cys Glu Leu Gln Pro
     25                  30                  35 cac ggc ctg gtg aac tgc aac tgg ctg ttc ctg aag tct gtg ccc cac        799
His Gly Leu Val Asn Cys Asn Trp Leu Phe Leu Lys Ser Val Pro His
 40                  45                  50                  55 ttc tcc atg gca gca ccc cgt ggc aat gtc acc agc ctt tcc ttg tcc        847
Phe Ser Met Ala Ala Pro Arg Gly Asn Val Thr Ser Leu Ser Leu Ser
                 60                  65                  70 tcc aac cgc atc cac cac ctc cat gat tct gac ttt gcc cac ctg ccc        895
Ser Asn Arg Ile His His Leu His Asp Ser Asp Phe Ala His Leu Pro
             75                  80                  85 agc ctg cgg cat ctc aac ctc aag tgg aac tgc ccg ccg gtt ggc ctc        943
Ser Leu Arg His Leu Asn Leu Lys Trp Asn Cys Pro Pro Val Gly Leu
         90                  95                 100 agc ccc atg cac ttc ccc tgc cac atg acc atc gag ccc agc acc ttc        991
Ser Pro Met His Phe Pro Cys His Met Thr Ile Glu Pro Ser Thr Phe
    105                 110                 115 ttg gct gtg ccc acc ctg gaa gag cta aac ctg agc tac aac aac atc       1039
Leu Ala Val Pro Thr Leu Glu Glu Leu Asn Leu Ser Tyr Asn Asn Ile
120                 125                 130                 135 atg act gtg cct gcg ctg ccc aaa tcc ctc ata tcc ctg tcc ctc agc       1087
Met Thr Val Pro Ala Leu Pro Lys Ser Leu Ile Ser Leu Ser Leu Ser
                140                 145                 150
```

-continued

| | |
|---|---|
| cat acc aac atc ctg atg cta gac tct gcc agc ctc gcc ggc ctg cat<br>His Thr Asn Ile Leu Met Leu Asp Ser Ala Ser Leu Ala Gly Leu His<br>              155                  160                 165 | 1135 |
| gcc ctg cgc ttc cta ttc atg gac ggc aac tgt tat tac aag aac ccc<br>Ala Leu Arg Phe Leu Phe Met Asp Gly Asn Cys Tyr Tyr Lys Asn Pro<br>        170                   175                  180 | 1183 |
| tgc agg cag gca ctg gag gtg gcc ccg ggt gcc ctc ctt ggc ctg ggc<br>Cys Arg Gln Ala Leu Glu Val Ala Pro Gly Ala Leu Leu Gly Leu Gly<br>185                    190                  195 | 1231 |
| aac ctc acc cac ctg tca ctc aag tac aac aac ctc act gtg gtg ccc<br>Asn Leu Thr His Leu Ser Leu Lys Tyr Asn Asn Leu Thr Val Val Pro<br>200                 205                210               215 | 1279 |
| cgc aac ctg cct tcc agc ctg gag tat ctg ctg ttg tcc tac aac cgc<br>Arg Asn Leu Pro Ser Ser Leu Glu Tyr Leu Leu Leu Ser Tyr Asn Arg<br>                  220                  225               230 | 1327 |
| atc gtc aaa ctg gcg cct gag gac ctg gcc aat ctg acc gcc ctg cgt<br>Ile Val Lys Leu Ala Pro Glu Asp Leu Ala Asn Leu Thr Ala Leu Arg<br>              235                  240                245 | 1375 |
| gtg ctc gat gtg ggc gga aat tgc cgc cgc tgc gac cac gct ccc aac<br>Val Leu Asp Val Gly Gly Asn Cys Arg Arg Cys Asp His Ala Pro Asn<br>        250                   255                  260 | 1423 |
| ccc tgc atg gag tgc cct cgt cac ttc ccc cag cta cat ccc gat acc<br>Pro Cys Met Glu Cys Pro Arg His Phe Pro Gln Leu His Pro Asp Thr<br>265                    270                  275 | 1471 |
| ttc agc cac ctg agc cgt ctt gaa ggc ctg gtg ttg aag gac agt tct<br>Phe Ser His Leu Ser Arg Leu Glu Gly Leu Val Leu Lys Asp Ser Ser<br>280                    285                  290               295 | 1519 |
| ctc tcc tgg ctg aat gcc agt tgg ttc cgt ggg ctg gga aac ctc cga<br>Leu Ser Trp Leu Asn Ala Ser Trp Phe Arg Gly Leu Gly Asn Leu Arg<br>                  300                  305               310 | 1567 |
| gtg ctg gac ctg agt gag aac ttc ctc tac aaa tgc atc act aaa acc<br>Val Leu Asp Leu Ser Glu Asn Phe Leu Tyr Lys Cys Ile Thr Lys Thr<br>              315                  320                325 | 1615 |
| aag gcc ttc cag ggc cta aca cag ctg cgc aag ctt aac ctg tcc ttc<br>Lys Ala Phe Gln Gly Leu Thr Gln Leu Arg Lys Leu Asn Leu Ser Phe<br>                  330                  335               340 | 1663 |
| aat tac caa aag agg gtg tcc ttt gcc cac ctg tct ctg gcc cct tcc<br>Asn Tyr Gln Lys Arg Val Ser Phe Ala His Leu Ser Leu Ala Pro Ser<br>345                    350                  355 | 1711 |
| ttc ggg agc ctg gtc gcc ctg aag gag ctg gac atg cac ggc atc ttc<br>Phe Gly Ser Leu Val Ala Leu Lys Glu Leu Asp Met His Gly Ile Phe<br>360                    365                  370               375 | 1759 |
| ttc cgc tca ctc gat gag acc acg ctc cgg cca ctg gcc cgc ctg ccc<br>Phe Arg Ser Leu Asp Glu Thr Thr Leu Arg Pro Leu Ala Arg Leu Pro<br>                  380                  385               390 | 1807 |
| atg ctc cag act ctg cgt ctg cag atg aac ttc atc aac cag gcc cag<br>Met Leu Gln Thr Leu Arg Leu Gln Met Asn Phe Ile Asn Gln Ala Gln<br>              395                  400                405 | 1855 |
| ctc ggc atc ttc agg gcc ttc cct ggc ctg cgc tac gtg gac ctg tcg<br>Leu Gly Ile Phe Arg Ala Phe Pro Gly Leu Arg Tyr Val Asp Leu Ser<br>            410                   415                 420 | 1903 |
| gac aac cgc atc agc gga gct tcg gag ctg aca gcc acc atg ggg gag<br>Asp Asn Arg Ile Ser Gly Ala Ser Glu Leu Thr Ala Thr Met Gly Glu<br>425                    430                  435 | 1951 |
| gca gat gga ggg gag aag gtc tgg ctg cag cct ggg gac ctt gct ccg<br>Ala Asp Gly Gly Glu Lys Val Trp Leu Gln Pro Gly Asp Leu Ala Pro<br>440                    445                  450               455 | 1999 |
| gcc cca gtg gac act ccc agc tct gaa gac ttc agg ccc aac tgc agc<br>Ala Pro Val Asp Thr Pro Ser Ser Glu Asp Phe Arg Pro Asn Cys Ser<br>                  460                  465               470 | 2047 |

| | |
|---|---|
| acc ctc aac ttc acc ttg gat ctg tca cgg aac aac ctg gtg acc gtg<br>Thr Leu Asn Phe Thr Leu Asp Leu Ser Arg Asn Asn Leu Val Thr Val<br>475 480 485 | 2095 |
| cag ccg gag atg ttt gcc cag ctc tcg cac ctg cag tgc ctg cgc ctg<br>Gln Pro Glu Met Phe Ala Gln Leu Ser His Leu Gln Cys Leu Arg Leu<br>490 495 500 | 2143 |
| agc cac aac tgc atc tcg cag gca gtc aat ggc tcc cag ttc ctg ccg<br>Ser His Asn Cys Ile Ser Gln Ala Val Asn Gly Ser Gln Phe Leu Pro<br>505 510 515 | 2191 |
| ctg acc ggt ctg cag gtg cta gac ctg tcc cac aat aag ctg gac ctc<br>Leu Thr Gly Leu Gln Val Leu Asp Leu Ser His Asn Lys Leu Asp Leu<br>520 525 530 535 | 2239 |
| tac cac gag cac tca ttc acg gag cta cca cga ctg gag gcc ctg gac<br>Tyr His Glu His Ser Phe Thr Glu Leu Pro Arg Leu Glu Ala Leu Asp<br>540 545 550 | 2287 |
| ctc agc tac aac agc cag ccc ttt ggc atg cag ggc gtg ggc cac aac<br>Leu Ser Tyr Asn Ser Gln Pro Phe Gly Met Gln Gly Val Gly His Asn<br>555 560 565 | 2335 |
| ttc agc ttc gtg gct cac ctg cgc acc ctg cgc cac ctc agc ctg gcc<br>Phe Ser Phe Val Ala His Leu Arg Thr Leu Arg His Leu Ser Leu Ala<br>570 575 580 | 2383 |
| cac aac aac atc cac agc caa gtg tcc cag cag ctc tgc agt acg tcg<br>His Asn Asn Ile His Ser Gln Val Ser Gln Gln Leu Cys Ser Thr Ser<br>585 590 595 | 2431 |
| ctg cgg gcc ctg gac ttc agc ggc aat gca ctg ggc cat atg tgg gcc<br>Leu Arg Ala Leu Asp Phe Ser Gly Asn Ala Leu Gly His Met Trp Ala<br>600 605 610 615 | 2479 |
| gag gga gac ctc tat ctg cac ttc ttc caa ggc ctg agc ggt ttg atc<br>Glu Gly Asp Leu Tyr Leu His Phe Phe Gln Gly Leu Ser Gly Leu Ile<br>620 625 630 | 2527 |
| tgg ctg gac ttg tcc cag aac cgc ctg cac acc ctc ctg ccc caa acc<br>Trp Leu Asp Leu Ser Gln Asn Arg Leu His Thr Leu Leu Pro Gln Thr<br>635 640 645 | 2575 |
| ctg cgc aac ctc ccc aag agc cta cag gtg ctg cgt ctc cgt gac aat<br>Leu Arg Asn Leu Pro Lys Ser Leu Gln Val Leu Arg Leu Arg Asp Asn<br>650 655 660 | 2623 |
| tac ctg gcc ttc ttt aag tgg tgg agc ctc cac ttc ctg ccc aaa ctg<br>Tyr Leu Ala Phe Phe Lys Trp Trp Ser Leu His Phe Leu Pro Lys Leu<br>665 670 675 | 2671 |
| gaa gtc ctc gac ctg gca gga aac cag ctg aag gcc ctg acc aat ggc<br>Glu Val Leu Asp Leu Ala Gly Asn Gln Leu Lys Ala Leu Thr Asn Gly<br>680 685 690 695 | 2719 |
| agc ctg cct gct ggc acc cgg ctc cgg agg ctg gat gtc agc tgc aac<br>Ser Leu Pro Ala Gly Thr Arg Leu Arg Arg Leu Asp Val Ser Cys Asn<br>700 705 710 | 2767 |
| agc atc agc ttc gtg gcc ccc ggc ttc ttt tcc aag gcc aag gag ctg<br>Ser Ile Ser Phe Val Ala Pro Gly Phe Phe Ser Lys Ala Lys Glu Leu<br>715 720 725 | 2815 |
| cga gag ctc aac ctt agc gcc aac gcc ctc aag aca gtg gac cac tcc<br>Arg Glu Leu Asn Leu Ser Ala Asn Ala Leu Lys Thr Val Asp His Ser<br>730 735 740 | 2863 |
| tgg ttt ggg ccc ctg gcg agt gcc ctg caa ata cta gat gta agc gcc<br>Trp Phe Gly Pro Leu Ala Ser Ala Leu Gln Ile Leu Asp Val Ser Ala<br>745 750 755 | 2911 |
| aac cct ctg cac tgc gcc tgt ggg gcg gcc ttt atg gac ttc ctg ctg<br>Asn Pro Leu His Cys Ala Cys Gly Ala Ala Phe Met Asp Phe Leu Leu<br>760 765 770 775 | 2959 |
| gag gtg cag gct gcc gtg ccc ggt ctg ccc agc cgg gtg aag tgt ggc<br>Glu Val Gln Ala Ala Val Pro Gly Leu Pro Ser Arg Val Lys Cys Gly<br>780 785 790 | 3007 |

```
agt ccg ggc cag ctc cag ggc ctc agc atc ttt gca cag gac ctg cgc    3055
Ser Pro Gly Gln Leu Gln Gly Leu Ser Ile Phe Ala Gln Asp Leu Arg
        795                 800                 805 ctc tgc ctg gat gag gcc ctc tcc tgg gac tgt ttc gcc ctc tcg ctg    3103
Leu Cys Leu Asp Glu Ala Leu Ser Trp Asp Cys Phe Ala Leu Ser Leu
810                 815                 820 ctg gct gtg gct ctg ggc ctg ggt gtg ccc atg ctg cat cac ctc tgt    3151
Leu Ala Val Ala Leu Gly Leu Gly Val Pro Met Leu His His Leu Cys
            825                 830                 835 ggc tgg gac ctc tgg tac tgc ttc cac ctg tgc ctg gcc tgg ctt ccc    3199
Gly Trp Asp Leu Trp Tyr Cys Phe His Leu Cys Leu Ala Trp Leu Pro
840                 845                 850                 855 tgg cgg ggg cgg caa agt ggg cga gat gag gat gcc ctg ccc tac gat    3247
Trp Arg Gly Arg Gln Ser Gly Arg Asp Glu Asp Ala Leu Pro Tyr Asp
                860                 865                 870 gcc ttc gtg gtc ttc gac aaa acg cag agc gca gtg gca gac tgg gtg    3295
Ala Phe Val Val Phe Asp Lys Thr Gln Ser Ala Val Ala Asp Trp Val
            875                 880                 885 tac aac gag ctt cgg ggg cag ctg gag gag tgc cgt ggg cgc tgg gca    3343
Tyr Asn Glu Leu Arg Gly Gln Leu Glu Glu Cys Arg Gly Arg Trp Ala
        890                 895                 900 ctc cgc ctg tgc ctg gag gaa cgc gac tgg ctg cct ggc aaa acc ctc    3391
Leu Arg Leu Cys Leu Glu Glu Arg Asp Trp Leu Pro Gly Lys Thr Leu
905                 910                 915 ttt gag aac ctg tgg gcc tcg gtc tat ggc agc cgc aag acg ctg ttt    3439
Phe Glu Asn Leu Trp Ala Ser Val Tyr Gly Ser Arg Lys Thr Leu Phe
920                 925                 930                 935 gtg ctg gcc cac acg gac cgg gtc agt ggt ctc ttg cgc gcc agc ttc    3487
Val Leu Ala His Thr Asp Arg Val Ser Gly Leu Leu Arg Ala Ser Phe
                940                 945                 950 ctg ctg gcc cag cag cgc ctg ctg gag gac cgc aag gac gtc gtg gtg    3535
Leu Leu Ala Gln Gln Arg Leu Leu Glu Asp Arg Lys Asp Val Val Val
            955                 960                 965 ctg gtg atc ctg agc cct gac ggc cgc cgc tcc cgc tac gtg cgg ctg    3583
Leu Val Ile Leu Ser Pro Asp Gly Arg Arg Ser Arg Tyr Val Arg Leu
        970                 975                 980 cgc cag cgc ctc tgc cgc cag agt gtc ctc ctc tgg ccc cac cag ccc    3631
Arg Gln Arg Leu Cys Arg Gln Ser Val Leu Leu Trp Pro His Gln Pro
985                 990                 995 agt  ggt cag cgc agc ttc  tgg gcc cag ctg ggc  atg gcc ctg acc    3676
Ser  Gly Gln Arg Ser Phe  Trp Ala Gln Leu Gly  Met Ala Leu Thr
1000                 1005                  1010 agg  gac aac cac cac ttc  tat aac cgg aac ttc  tgc cag gga ccc    3721
Arg  Asp Asn His His Phe  Tyr Asn Arg Asn Phe  Cys Gln Gly Pro
1015                 1020                  1025 acg  gcc gaa tag ccgtgagccg gaatcctgca cggtgccacc tccacactca       3773
Thr  Ala Glu
1030 cctcacctct gcctgcctgg tctgacctc ccctgctcgc ctccctcacc ccacacctga    3833 cacagagcag gcactcaata aatgctaccg aaggc                              3868

<210> SEQ ID NO 4
<211> LENGTH: 1032
<212> TYPE: PRT
<213> ORGANISM: Homo sapiens

<400> SEQUENCE: 4

Met Gly Phe Cys Arg Ser Ala Leu His Pro Leu Ser Leu Leu Val Gln
1               5                   10                  15
```

-continued

```
Ala Ile Met Leu Ala Met Thr Leu Ala Leu Gly Thr Leu Pro Ala Phe
         20                  25                  30

Leu Pro Cys Glu Leu Gln Pro His Gly Leu Val Asn Cys Asn Trp Leu
         35                  40                  45

Phe Leu Lys Ser Val Pro His Phe Ser Met Ala Ala Pro Arg Gly Asn
 50                  55                  60

Val Thr Ser Leu Ser Leu Ser Ser Asn Arg Ile His His Leu His Asp
 65                  70                  75                  80

Ser Asp Phe Ala His Leu Pro Ser Leu Arg His Leu Asn Leu Lys Trp
                 85                  90                  95

Asn Cys Pro Pro Val Gly Leu Ser Pro Met His Phe Pro Cys His Met
                100                 105                 110

Thr Ile Glu Pro Ser Thr Phe Leu Ala Val Pro Thr Leu Glu Glu Leu
            115                 120                 125

Asn Leu Ser Tyr Asn Asn Ile Met Thr Val Pro Ala Leu Pro Lys Ser
        130                 135                 140

Leu Ile Ser Leu Ser Leu Ser His Thr Asn Ile Leu Met Leu Asp Ser
145                 150                 155                 160

Ala Ser Leu Ala Gly Leu His Ala Leu Arg Phe Leu Phe Met Asp Gly
                165                 170                 175

Asn Cys Tyr Tyr Lys Asn Pro Cys Arg Gln Ala Leu Glu Val Ala Pro
                180                 185                 190

Gly Ala Leu Leu Gly Leu Gly Asn Leu Thr His Leu Ser Leu Lys Tyr
            195                 200                 205

Asn Asn Leu Thr Val Val Pro Arg Asn Leu Pro Ser Ser Leu Glu Tyr
        210                 215                 220

Leu Leu Leu Ser Tyr Asn Arg Ile Val Lys Leu Ala Pro Glu Asp Leu
225                 230                 235                 240

Ala Asn Leu Thr Ala Leu Arg Val Leu Asp Val Gly Gly Asn Cys Arg
                245                 250                 255

Arg Cys Asp His Ala Pro Asn Pro Cys Met Glu Cys Pro Arg His Phe
                260                 265                 270

Pro Gln Leu His Pro Asp Thr Phe Ser His Leu Ser Arg Leu Glu Gly
            275                 280                 285

Leu Val Leu Lys Asp Ser Ser Leu Ser Trp Leu Asn Ala Ser Trp Phe
        290                 295                 300

Arg Gly Leu Gly Asn Leu Arg Val Leu Asp Leu Ser Glu Asn Phe Leu
305                 310                 315                 320

Tyr Lys Cys Ile Thr Lys Thr Lys Ala Phe Gln Gly Leu Thr Gln Leu
                325                 330                 335

Arg Lys Leu Asn Leu Ser Phe Asn Tyr Gln Lys Arg Val Ser Phe Ala
            340                 345                 350

His Leu Ser Leu Ala Pro Ser Phe Gly Ser Leu Val Ala Leu Lys Glu
        355                 360                 365

Leu Asp Met His Gly Ile Phe Phe Arg Ser Leu Asp Glu Thr Thr Leu
            370                 375                 380

Arg Pro Leu Ala Arg Leu Pro Met Leu Gln Thr Leu Arg Leu Gln Met
385                 390                 395                 400

Asn Phe Ile Asn Gln Ala Gln Leu Gly Ile Phe Arg Ala Phe Pro Gly
                405                 410                 415

Leu Arg Tyr Val Asp Leu Ser Asp Asn Arg Ile Ser Gly Ala Ser Glu
            420                 425                 430

Leu Thr Ala Thr Met Gly Glu Ala Asp Gly Gly Glu Lys Val Trp Leu
        435                 440                 445
```

```
Gln Pro Gly Asp Leu Ala Pro Ala Pro Val Asp Thr Pro Ser Ser Glu
    450                 455                 460

Asp Phe Arg Pro Asn Cys Ser Thr Leu Asn Phe Thr Leu Asp Leu Ser
465                 470                 475                 480

Arg Asn Asn Leu Val Thr Val Gln Pro Glu Met Phe Ala Gln Leu Ser
                    485                 490                 495

His Leu Gln Cys Leu Arg Leu Ser His Asn Cys Ile Ser Gln Ala Val
            500                 505                 510

Asn Gly Ser Gln Phe Leu Pro Leu Thr Gly Leu Gln Val Leu Asp Leu
        515                 520                 525

Ser His Asn Lys Leu Asp Leu Tyr His Glu His Ser Phe Thr Glu Leu
    530                 535                 540

Pro Arg Leu Glu Ala Leu Asp Leu Ser Tyr Asn Ser Gln Pro Phe Gly
545                 550                 555                 560

Met Gln Gly Val Gly His Asn Phe Ser Phe Val Ala His Leu Arg Thr
                    565                 570                 575

Leu Arg His Leu Ser Leu Ala His Asn Asn Ile His Ser Gln Val Ser
            580                 585                 590

Gln Gln Leu Cys Ser Thr Ser Leu Arg Ala Leu Asp Phe Ser Gly Asn
        595                 600                 605

Ala Leu Gly His Met Trp Ala Glu Gly Asp Leu Tyr Leu His Phe Phe
    610                 615                 620

Gln Gly Leu Ser Gly Leu Ile Trp Leu Asp Leu Ser Gln Asn Arg Leu
625                 630                 635                 640

His Thr Leu Leu Pro Gln Thr Leu Arg Asn Leu Pro Lys Ser Leu Gln
                    645                 650                 655

Val Leu Arg Leu Arg Asp Asn Tyr Leu Ala Phe Phe Lys Trp Trp Ser
            660                 665                 670

Leu His Phe Leu Pro Lys Leu Glu Val Leu Asp Leu Ala Gly Asn Gln
        675                 680                 685

Leu Lys Ala Leu Thr Asn Gly Ser Leu Pro Ala Gly Thr Arg Leu Arg
    690                 695                 700

Arg Leu Asp Val Ser Cys Asn Ser Ile Ser Phe Val Ala Pro Gly Phe
705                 710                 715                 720

Phe Ser Lys Ala Lys Glu Leu Arg Glu Leu Asn Leu Ser Ala Asn Ala
                    725                 730                 735

Leu Lys Thr Val Asp His Ser Trp Phe Gly Pro Leu Ala Ser Ala Leu
            740                 745                 750

Gln Ile Leu Asp Val Ser Ala Asn Pro Leu His Cys Ala Cys Gly Ala
        755                 760                 765

Ala Phe Met Asp Phe Leu Leu Glu Val Gln Ala Ala Val Pro Gly Leu
    770                 775                 780

Pro Ser Arg Val Lys Cys Gly Ser Pro Gly Gln Leu Gln Gly Leu Ser
785                 790                 795                 800

Ile Phe Ala Gln Asp Leu Arg Leu Cys Leu Asp Glu Ala Leu Ser Trp
                    805                 810                 815

Asp Cys Phe Ala Leu Ser Leu Leu Ala Val Ala Leu Gly Leu Gly Val
            820                 825                 830

Pro Met Leu His His Leu Cys Gly Trp Asp Leu Trp Tyr Cys Phe His
    835                 840                 845

Leu Cys Leu Ala Trp Leu Pro Trp Arg Gly Arg Gln Ser Gly Arg Asp
850                 855                 860

Glu Asp Ala Leu Pro Tyr Asp Ala Phe Val Val Phe Asp Lys Thr Gln
```

```
                    865                 870                 875                 880
Ser Ala Val Ala Asp Trp Val Tyr Asn Glu Leu Arg Gly Gln Leu Glu
                    885                 890                 895
Glu Cys Arg Gly Arg Trp Ala Leu Arg Leu Cys Leu Glu Glu Arg Asp
                    900                 905                 910
Trp Leu Pro Gly Lys Thr Leu Phe Glu Asn Leu Trp Ala Ser Val Tyr
                    915                 920                 925
Gly Ser Arg Lys Thr Leu Phe Val Leu Ala His Thr Asp Arg Val Ser
                    930                 935                 940
Gly Leu Leu Arg Ala Ser Phe Leu Leu Ala Gln Gln Arg Leu Leu Glu
945                 950                 955                 960
Asp Arg Lys Asp Val Val Leu Val Ile Leu Ser Pro Asp Gly Arg
                    965                 970                 975
Arg Ser Arg Tyr Val Arg Leu Arg Gln Arg Leu Cys Arg Gln Ser Val
                    980                 985                 990
Leu Leu Trp Pro His Gln Pro Ser  Gly Gln Arg Ser Phe  Trp Ala Gln
                    995                1000                1005
Leu Gly  Met Ala Leu Thr Arg  Asp Asn His His Phe  Tyr Asn Arg
   1010                1015                1020
Asn Phe  Cys Gln Gly Pro Thr  Ala Glu
   1025                1030

<210> SEQ ID NO 5
<211> LENGTH: 3340
<212> TYPE: DNA
<213> ORGANISM: Mus musculus
<220> FEATURE:
<221> NAME/KEY: CDS
<222> LOCATION: (86)..(3184)
<223> OTHER INFORMATION:

<400> SEQUENCE: 5
tctctgagag accctggtgt ggaacatcat tctctgccgc ccagtttgtc agagggagcc    60
tcgggagaat cctccatctc ccaac atg gtt ctc cgt cga agg act ctg cac   112
                              Met Val Leu Arg Arg Arg Thr Leu His
                                1               5 ccc ttg tcc ctc ctg gta cag gct gca gtg ctg gct gag act ctg gcc   160
Pro Leu Ser Leu Leu Val Gln Ala Ala Val Leu Ala Glu Thr Leu Ala
 10              15                  20                  25 ctg ggt acc ctg cct gcc ttc cta ccc tgt gag ctg aag cct cat ggc   208
Leu Gly Thr Leu Pro Ala Phe Leu Pro Cys Glu Leu Lys Pro His Gly
                 30                  35                  40 ctg gtg gac tgc aat tgg ctg ttc ctg aag tct gta ccc cgt ttc tct   256
Leu Val Asp Cys Asn Trp Leu Phe Leu Lys Ser Val Pro Arg Phe Ser
             45                  50                  55 gcg gca gca tcc tgc tcc aac atc acc cgc ctc tcc ttg atc tcc aac   304
Ala Ala Ala Ser Cys Ser Asn Ile Thr Arg Leu Ser Leu Ile Ser Asn
         60                  65                  70 cgt atc cac cac ctg cac aac tcc gac ttc gtc cac ctg tcc aac ctg   352
Arg Ile His His Leu His Asn Ser Asp Phe Val His Leu Ser Asn Leu
     75                  80                  85 cgg cag ctg aac ctc aag tgg aac tgt cca ccc act ggc ctt agc ccc   400
Arg Gln Leu Asn Leu Lys Trp Asn Cys Pro Pro Thr Gly Leu Ser Pro
 90                  95                 100                 105 ctg cac ttc tct tgc cac atg acc att gag ccc aga acc ttc ctg gct   448
Leu His Phe Ser Cys His Met Thr Ile Glu Pro Arg Thr Phe Leu Ala
                110                 115                 120 atg cgt aca ctg gag gag ctg aac ctg agc tat aat ggt atc acc act   496
Met Arg Thr Leu Glu Glu Leu Asn Leu Ser Tyr Asn Gly Ile Thr Thr
```

```
                125                 130                 135
gtg ccc cga ctg ccc agc tcc ctg gtg aat ctg agc ctg agc cac acc      544
Val Pro Arg Leu Pro Ser Ser Leu Val Asn Leu Ser Leu Ser His Thr
        140                 145                 150 aac atc ctg gtt cta gat gct aac agc ctc gcc ggc cta tac agc ctg      592
Asn Ile Leu Val Leu Asp Ala Asn Ser Leu Ala Gly Leu Tyr Ser Leu
155                 160                 165 cgc gtt ctc ttc atg gac ggg aac tgc tac tac aag aac ccc tgc aca      640
Arg Val Leu Phe Met Asp Gly Asn Cys Tyr Tyr Lys Asn Pro Cys Thr
170                 175                 180                 185 gga gcg gtg aag gtg acc cca ggc gcc ctc ctg ggc ctg agc aat ctc      688
Gly Ala Val Lys Val Thr Pro Gly Ala Leu Leu Gly Leu Ser Asn Leu
                190                 195                 200 acc cat ctg tct ctg aag tat aac aac ctc aca aag gtg ccc cgc caa      736
Thr His Leu Ser Leu Lys Tyr Asn Asn Leu Thr Lys Val Pro Arg Gln
            205                 210                 215 ctg ccc ccc agc ctg gag tac ctc ctg gtg tcc tat aac ctc att gtc      784
Leu Pro Pro Ser Leu Glu Tyr Leu Leu Val Ser Tyr Asn Leu Ile Val
        220                 225                 230 aag ctg ggg cct gaa gac ctg gcc aat ctg acc tcc ctt cga gta ctt      832
Lys Leu Gly Pro Glu Asp Leu Ala Asn Leu Thr Ser Leu Arg Val Leu
235                 240                 245 gat gtg ggt ggg aat tgc cgt cgc tgc gac cat gcc ccc aat ccc tgt      880
Asp Val Gly Gly Asn Cys Arg Arg Cys Asp His Ala Pro Asn Pro Cys
250                 255                 260                 265 ata gaa tgt ggc caa aag tcc ctc cac ctg cac cct gag acc ttc cat      928
Ile Glu Cys Gly Gln Lys Ser Leu His Leu His Pro Glu Thr Phe His
                270                 275                 280 cac ctg agc cat ctg gaa ggc ctg gtg ctg aag gac agc tct ctc cat      976
His Leu Ser His Leu Glu Gly Leu Val Leu Lys Asp Ser Ser Leu His
            285                 290                 295 aca ctg aac tct tcc tgg ttc caa ggt ctg gtc aac ctc tcg gtg ctg      1024
Thr Leu Asn Ser Ser Trp Phe Gln Gly Leu Val Asn Leu Ser Val Leu
        300                 305                 310 gac cta agc gag aac ttt ctc tat gaa agc atc aac cac acc aat gcc      1072
Asp Leu Ser Glu Asn Phe Leu Tyr Glu Ser Ile Asn His Thr Asn Ala
315                 320                 325 ttt cag aac cta acc cgc ctg cgc aag ctc aac ctg tcc ttc aat tac      1120
Phe Gln Asn Leu Thr Arg Leu Arg Lys Leu Asn Leu Ser Phe Asn Tyr
330                 335                 340                 345 cgc aag aag gta tcc ttt gcc cgc ctc cac ctg gca agt tcc ttc aag      1168
Arg Lys Lys Val Ser Phe Ala Arg Leu His Leu Ala Ser Ser Phe Lys
                350                 355                 360 aac ctg gtg tca ctg cag gag ctg aac atg aac ggc atc ttc ttc cgc      1216
Asn Leu Val Ser Leu Gln Glu Leu Asn Met Asn Gly Ile Phe Phe Arg
            365                 370                 375 tcg ctc aac aag tac acg ctc aga tgg ctg gcc gat ctg ccc aaa ctc      1264
Ser Leu Asn Lys Tyr Thr Leu Arg Trp Leu Ala Asp Leu Pro Lys Leu
        380                 385                 390 cac act ctg cat ctt caa atg aac ttc atc aac cag gca cag ctc agc      1312
His Thr Leu His Leu Gln Met Asn Phe Ile Asn Gln Ala Gln Leu Ser
395                 400                 405 atc ttt ggt acc ttc cga gcc ctt cgc ttt gtg gac ttg tca gac aat      1360
Ile Phe Gly Thr Phe Arg Ala Leu Arg Phe Val Asp Leu Ser Asp Asn
410                 415                 420                 425 cgc atc agt ggg cct tca acg ctg tca gaa gcc acc cct gaa gag gca      1408
Arg Ile Ser Gly Pro Ser Thr Leu Ser Glu Ala Thr Pro Glu Glu Ala
                430                 435                 440 gat gat gca gag cag gag gag ctg ttg tct gcg gat cct cac cca gct      1456
Asp Asp Ala Glu Gln Glu Glu Leu Leu Ser Ala Asp Pro His Pro Ala
```

-continued

```
                      445                 450                  455
cca ctg agc acc cct gct tct aag aac ttc atg gac agg tgt aag aac    1504
Pro Leu Ser Thr Pro Ala Ser Lys Asn Phe Met Asp Arg Cys Lys Asn
        460                 465                 470 ttc aag ttc acc atg gac ctg tct cgg aac aac ctg gtg act atc aag    1552
Phe Lys Phe Thr Met Asp Leu Ser Arg Asn Asn Leu Val Thr Ile Lys
    475                 480                 485 cca gag atg ttt gtc aat ctc tca cgc ctc cag tgt ctt agc ctg agc    1600
Pro Glu Met Phe Val Asn Leu Ser Arg Leu Gln Cys Leu Ser Leu Ser
490                 495                 500                 505 cac aac tcc att gca cag gct gtc aat ggc tct cag ttc ctg ccg ctg    1648
His Asn Ser Ile Ala Gln Ala Val Asn Gly Ser Gln Phe Leu Pro Leu
            510                 515                 520 act aat ctg cag gtg ctg gac ctg tcc cat aac aaa ctg gac ttg tac    1696
Thr Asn Leu Gln Val Leu Asp Leu Ser His Asn Lys Leu Asp Leu Tyr
        525                 530                 535 cac tgg aaa tcg ttc agt gag cta cca cag ttg cag gcc ctg gac ctg    1744
His Trp Lys Ser Phe Ser Glu Leu Pro Gln Leu Gln Ala Leu Asp Leu
    540                 545                 550 ggc tac aac agc cag ccc ttt agc ata aag ggt ata ggc cac aat ttc    1792
Gly Tyr Asn Ser Gln Pro Phe Ser Ile Lys Gly Ile Gly His Asn Phe
555                 560                 565 agt ttt gtg gcc cat ctg tcc atg cta cac agc ctt agc ctg gca cac    1840
Ser Phe Val Ala His Leu Ser Met Leu His Ser Leu Ser Leu Ala His
570                 575                 580                 585 aat gac att cat acc cgt gtg tcc tca cat ctc aac agc aac tca gtg    1888
Asn Asp Ile His Thr Arg Val Ser Ser His Leu Asn Ser Asn Ser Val
            590                 595                 600 agg ttt ctt gac ttc agc ggc aac ggt atg ggc cgc atg tgg gat gag    1936
Arg Phe Leu Asp Phe Ser Gly Asn Gly Met Gly Arg Met Trp Asp Glu
        605                 610                 615 ggg ggc ctt tat ctc cat ttc ttc caa ggc ctg agt ggc ctg ctg aag    1984
Gly Gly Leu Tyr Leu His Phe Phe Gln Gly Leu Ser Gly Leu Leu Lys
    620                 625                 630 ctg gac ctg tct caa aat aac ctg cat atc ctc cgg ccc cag aac ctt    2032
Leu Asp Leu Ser Gln Asn Asn Leu His Ile Leu Arg Pro Gln Asn Leu
635                 640                 645 gac aac ctc ccc aag agc ctg aag ctg ctg agc ctc cga gac aac tac    2080
Asp Asn Leu Pro Lys Ser Leu Lys Leu Leu Ser Leu Arg Asp Asn Tyr
650                 655                 660                 665 cta tct ttc ttt aac tgg acc agt ctg tcc ttc ctg ccc aac ctg gaa    2128
Leu Ser Phe Phe Asn Trp Thr Ser Leu Ser Phe Leu Pro Asn Leu Glu
            670                 675                 680 gtc cta gac ctg gca ggc aac cag cta aag gcc ctg acc aat ggc acc    2176
Val Leu Asp Leu Ala Gly Asn Gln Leu Lys Ala Leu Thr Asn Gly Thr
        685                 690                 695 ctg cct aat ggc acc ctc ctc cag aaa ctg gat gtc agc agc aac agt    2224
Leu Pro Asn Gly Thr Leu Leu Gln Lys Leu Asp Val Ser Ser Asn Ser
    700                 705                 710 atc gtc tct gtg gtc cca gcc ttc ttc gct ctg gcg gtc gag ctg aaa    2272
Ile Val Ser Val Val Pro Ala Phe Phe Ala Leu Ala Val Glu Leu Lys
715                 720                 725 gag gtc aac ctc agc cac aac att ctc aag acg gtg gat cgc tcc tgg    2320
Glu Val Asn Leu Ser His Asn Ile Leu Lys Thr Val Asp Arg Ser Trp
730                 735                 740                 745 ttt ggg ccc att gtg atg aac ctg aca gtt cta gac gtg aga agc aac    2368
Phe Gly Pro Ile Val Met Asn Leu Thr Val Leu Asp Val Arg Ser Asn
            750                 755                 760 cct ctg cac tgt gcc tgt ggg gca gcc ttc gta gac tta ctg ttg gag    2416
Pro Leu His Cys Ala Cys Gly Ala Ala Phe Val Asp Leu Leu Leu Glu
```

-continued

```
                765                 770                 775
gtg cag acc aag gtg cct ggc ctg gct aat ggt gtg aag tgt ggc agc         2464
Val Gln Thr Lys Val Pro Gly Leu Ala Asn Gly Val Lys Cys Gly Ser
        780                 785                 790 ccc ggc cag ctg cag ggc cgt agc atc ttc gca cag gac ctg cgg ctg         2512
Pro Gly Gln Leu Gln Gly Arg Ser Ile Phe Ala Gln Asp Leu Arg Leu
    795                 800                 805 tgc ctg gat gag gtc ctc tct tgg gac tgc ttt ggc ctt tca ctc ttg         2560
Cys Leu Asp Glu Val Leu Ser Trp Asp Cys Phe Gly Leu Ser Leu Leu
810                 815                 820                 825 gct gtg gcc gtg ggc atg gtg gtg cct ata ctg cac cat ctc tgc ggc         2608
Ala Val Ala Val Gly Met Val Val Pro Ile Leu His His Leu Cys Gly
                830                 835                 840 tgg gac gtc tgg tac tgt ttt cat ctg tgc ctg gca tgg cta cct ttg         2656
Trp Asp Val Trp Tyr Cys Phe His Leu Cys Leu Ala Trp Leu Pro Leu
            845                 850                 855 ctg gcc cgc agc cga cgc agc gcc caa gct ctc ccc tat gat gcc ttc         2704
Leu Ala Arg Ser Arg Arg Ser Ala Gln Ala Leu Pro Tyr Asp Ala Phe
        860                 865                 870 gtg gtg ttc gat aag gca cag agc gca gtt gcg gac tgg gtg tat aac         2752
Val Val Phe Asp Lys Ala Gln Ser Ala Val Ala Asp Trp Val Tyr Asn
    875                 880                 885 gag ctg cgg gtg cgg ctg gag ggg cgg cgc ggt cgc gac cgc cta cgc         2800
Glu Leu Arg Val Arg Leu Glu Gly Arg Arg Gly Arg Arg Ala Leu Arg
890                 895                 900                 905 ttg tgt ctg gag gac cga gat tgg ctg cct ggc cag acg ctc ttc gag         2848
Leu Cys Leu Glu Asp Arg Asp Trp Leu Pro Gly Gln Thr Leu Phe Glu
                910                 915                 920 aac ctc tgg gct tcc atc tat ggg agc cgc aag act cta ttt gtg ctg         2896
Asn Leu Trp Ala Ser Ile Tyr Gly Ser Arg Lys Thr Leu Phe Val Leu
            925                 930                 935 gcc cac acg gac cgc gtc agt ggc ctc ctg cgc acc agc ttc ctg ctg         2944
Ala His Thr Asp Arg Val Ser Gly Leu Leu Arg Thr Ser Phe Leu Leu
        940                 945                 950 gct cag cag cgc ctg ttg gaa gac cgc aag gac gtg gtg gtg ttg gtg         2992
Ala Gln Gln Arg Leu Leu Glu Asp Arg Lys Asp Val Val Val Leu Val
    955                 960                 965 atc ctg cgt ccg gat gcc cac cgc tcc cgc tat gtg cga ctg cgc cag         3040
Ile Leu Arg Pro Asp Ala His Arg Ser Arg Tyr Val Arg Leu Arg Gln
970                 975                 980                 985 cgt ctc tgc cgc cag agt gtg ctc ttt tgg ccc cag cag ccc aac  ggg        3088
Arg Leu Cys Arg Gln Ser Val Leu Phe Trp Pro Gln Gln Pro Asn  Gly
                990                 995                 1000 cag ggg ggc ttc tgg gcc cag ctg agt  aca gcc ctg act agg  gac           3133
Gln Gly Gly Phe Trp Ala Gln Leu Ser Thr Ala Leu Thr Arg  Asp
            1005                1010                 1015 aac cgc cac ttc tat aac cag aac ttc  tgc cgg gga cct aca  gca           3178
Asn Arg His Phe Tyr Asn Gln Asn Phe  Cys Arg Gly Pro Thr  Ala
        1020                1025                 1030 gaa tag ctcagagcaa cagctggaaa cagctgcatc ttcatgcctg gttcccgagt         3234
Glu tgctctgcct gccttgctct gtcttactac accgctattt ggcaagtgcg caatatatgc      3294
taccaagcca ccgggcccac ggagcaaagg ttggctgtaa aggta                      3340
```

<210> SEQ ID NO 6
<211> LENGTH: 1032
<212> TYPE: PRT
<213> ORGANISM: Mus musculus

<400> SEQUENCE: 6

```
Met Val Leu Arg Arg Arg Thr Leu His Pro Leu Ser Leu Val Gln
1               5                   10                  15

Ala Ala Val Leu Ala Glu Thr Leu Ala Leu Gly Thr Leu Pro Ala Phe
            20                  25                  30

Leu Pro Cys Glu Leu Lys Pro His Gly Leu Val Asp Cys Asn Trp Leu
        35                  40                  45

Phe Leu Lys Ser Val Pro Arg Phe Ser Ala Ala Ser Cys Ser Asn
    50                  55                  60

Ile Thr Arg Leu Ser Leu Ile Ser Asn Arg Ile His His Leu His Asn
65                  70                  75                  80

Ser Asp Phe Val His Leu Ser Asn Leu Arg Gln Leu Asn Leu Lys Trp
                85                  90                  95

Asn Cys Pro Pro Thr Gly Leu Ser Pro Leu His Phe Ser Cys His Met
            100                 105                 110

Thr Ile Glu Pro Arg Thr Phe Leu Ala Met Arg Thr Leu Glu Glu Leu
            115                 120                 125

Asn Leu Ser Tyr Asn Gly Ile Thr Thr Val Pro Arg Leu Pro Ser Ser
    130                 135                 140

Leu Val Asn Leu Ser Leu Ser His Thr Asn Ile Leu Val Leu Asp Ala
145                 150                 155                 160

Asn Ser Leu Ala Gly Leu Tyr Ser Leu Arg Val Leu Phe Met Asp Gly
                165                 170                 175

Asn Cys Tyr Tyr Lys Asn Pro Cys Thr Gly Ala Val Lys Val Thr Pro
            180                 185                 190

Gly Ala Leu Leu Gly Leu Ser Asn Leu Thr His Leu Ser Leu Lys Tyr
        195                 200                 205

Asn Asn Leu Thr Lys Val Pro Arg Gln Leu Pro Pro Ser Leu Glu Tyr
    210                 215                 220

Leu Leu Val Ser Tyr Asn Leu Ile Val Lys Leu Gly Pro Glu Asp Leu
225                 230                 235                 240

Ala Asn Leu Thr Ser Leu Arg Val Leu Asp Val Gly Gly Asn Cys Arg
                245                 250                 255

Arg Cys Asp His Ala Pro Asn Pro Cys Ile Glu Cys Gly Gln Lys Ser
            260                 265                 270

Leu His Leu His Pro Glu Thr Phe His His Leu Ser His Leu Glu Gly
        275                 280                 285

Leu Val Leu Lys Asp Ser Ser Leu His Thr Leu Asn Ser Ser Trp Phe
    290                 295                 300

Gln Gly Leu Val Asn Leu Ser Val Leu Asp Leu Ser Glu Asn Phe Leu
305                 310                 315                 320

Tyr Glu Ser Ile Asn His Thr Asn Ala Phe Gln Asn Leu Thr Arg Leu
                325                 330                 335

Arg Lys Leu Asn Leu Ser Phe Asn Tyr Arg Lys Lys Val Ser Phe Ala
            340                 345                 350

Arg Leu His Leu Ala Ser Ser Phe Lys Asn Leu Val Ser Leu Gln Glu
        355                 360                 365

Leu Asn Met Asn Gly Ile Phe Phe Arg Ser Leu Asn Lys Tyr Thr Leu
    370                 375                 380

Arg Trp Leu Ala Asp Leu Pro Lys Leu His Thr Leu His Leu Gln Met
385                 390                 395                 400

Asn Phe Ile Asn Gln Ala Gln Leu Ser Ile Phe Gly Thr Phe Arg Ala
                405                 410                 415

Leu Arg Phe Val Asp Leu Ser Asp Asn Arg Ile Ser Gly Pro Ser Thr
```

-continued

```
                420             425             430
Leu Ser Glu Ala Thr Pro Glu Ala Asp Asp Ala Glu Gln Glu Glu
            435                 440                 445
Leu Leu Ser Ala Asp Pro His Pro Ala Pro Leu Ser Thr Pro Ala Ser
    450                 455                 460
Lys Asn Phe Met Asp Arg Cys Lys Asn Phe Lys Phe Thr Met Asp Leu
465                 470                 475                 480
Ser Arg Asn Asn Leu Val Thr Ile Lys Pro Glu Met Phe Val Asn Leu
                485                 490                 495
Ser Arg Leu Gln Cys Leu Ser Leu Ser His Asn Ser Ile Ala Gln Ala
                500                 505                 510
Val Asn Gly Ser Gln Phe Leu Pro Leu Thr Asn Leu Gln Val Leu Asp
                515                 520                 525
Leu Ser His Asn Lys Leu Asp Leu Tyr His Trp Lys Ser Phe Ser Glu
        530                 535                 540
Leu Pro Gln Leu Gln Ala Leu Asp Leu Gly Tyr Asn Ser Gln Pro Phe
545                 550                 555                 560
Ser Ile Lys Gly Ile Gly His Asn Phe Ser Phe Val Ala His Leu Ser
                565                 570                 575
Met Leu His Ser Leu Ser Leu Ala His Asn Asp Ile His Thr Arg Val
        580                 585                 590
Ser Ser His Leu Asn Ser Asn Ser Val Arg Phe Leu Asp Phe Ser Gly
        595                 600                 605
Asn Gly Met Gly Arg Met Trp Asp Glu Gly Gly Leu Tyr Leu His Phe
        610                 615                 620
Phe Gln Gly Leu Ser Gly Leu Leu Lys Leu Asp Leu Ser Gln Asn Asn
625                 630                 635                 640
Leu His Ile Leu Arg Pro Gln Asn Leu Asp Asn Leu Pro Lys Ser Leu
                645                 650                 655
Lys Leu Leu Ser Leu Arg Asp Asn Tyr Leu Ser Phe Phe Asn Trp Thr
                660                 665                 670
Ser Leu Ser Phe Leu Pro Asn Leu Glu Val Leu Asp Leu Ala Gly Asn
        675                 680                 685
Gln Leu Lys Ala Leu Thr Asn Gly Thr Leu Pro Asn Gly Thr Leu Leu
    690                 695                 700
Gln Lys Leu Asp Val Ser Ser Asn Ser Ile Val Ser Val Val Pro Ala
705                 710                 715                 720
Phe Phe Ala Leu Ala Val Glu Leu Lys Glu Val Asn Leu Ser His Asn
                725                 730                 735
Ile Leu Lys Thr Val Asp Arg Ser Trp Phe Gly Pro Ile Val Met Asn
                740                 745                 750
Leu Thr Val Leu Asp Val Arg Ser Asn Pro Leu His Cys Ala Cys Gly
        755                 760                 765
Ala Ala Phe Val Asp Leu Leu Glu Val Gln Thr Lys Val Pro Gly
    770                 775                 780
Leu Ala Asn Gly Val Lys Cys Gly Ser Pro Gly Gln Leu Gln Gly Arg
785                 790                 795                 800
Ser Ile Phe Ala Gln Asp Leu Arg Leu Cys Leu Asp Glu Val Leu Ser
                805                 810                 815
Trp Asp Cys Phe Gly Leu Ser Leu Leu Ala Val Ala Val Gly Met Val
                820                 825                 830
Val Pro Ile Leu His His Leu Cys Gly Trp Asp Val Trp Tyr Cys Phe
                835                 840                 845
```

```
His Leu Cys Leu Ala Trp Leu Pro Leu Leu Ala Arg Ser Arg Arg Ser
        850                 855                 860

Ala Gln Ala Leu Pro Tyr Asp Ala Phe Val Val Phe Asp Lys Ala Gln
865                 870                 875                 880

Ser Ala Val Ala Asp Trp Val Tyr Asn Glu Leu Arg Val Arg Leu Glu
            885                 890                 895

Gly Arg Arg Gly Arg Arg Ala Leu Arg Leu Cys Leu Glu Asp Arg Asp
                900                 905                 910

Trp Leu Pro Gly Gln Thr Leu Phe Glu Asn Leu Trp Ala Ser Ile Tyr
        915                 920                 925

Gly Ser Arg Lys Thr Leu Phe Val Leu Ala His Thr Asp Arg Val Ser
    930                 935                 940

Gly Leu Leu Arg Thr Ser Phe Leu Leu Ala Gln Gln Arg Leu Leu Glu
945                 950                 955                 960

Asp Arg Lys Asp Val Val Leu Val Ile Leu Arg Pro Asp Ala His
                965                 970                 975

Arg Ser Arg Tyr Val Arg Leu Arg Gln Arg Leu Cys Arg Gln Ser Val
            980                 985                 990

Leu Phe Trp Pro Gln Gln Pro Asn  Gly Gln Gly Gly Phe  Trp Ala Gln
        995                 1000                1005

Leu Ser  Thr Ala Leu Thr Arg  Asp Asn Arg His Phe  Tyr Asn Gln
    1010                1015                1020

Asn Phe  Cys Arg Gly Pro Thr  Ala Glu
    1025                1030

<210> SEQ ID NO 7
<211> LENGTH: 3332
<212> TYPE: DNA
<213> ORGANISM: Felis Catus
<220> FEATURE:
<221> NAME/KEY: misc_feature
<222> LOCATION: (1952)..(1952)
<223> OTHER INFORMATION: "n"=A,T,G or C
<220> FEATURE:
<221> NAME/KEY: CDS
<222> LOCATION: (88)..(3183)
<223> OTHER INFORMATION:

<400> SEQUENCE: 7
aagggtctgc gagctccagg cattcttctc tgccatcgct gcccagtctg ccatccagac      60
cctctggaga agcccccact ccctgtc atg ggc ccc tgc cat ggc gcc ctg cac     114
                              Met Gly Pro Cys His Gly Ala Leu His
                                1               5 ccc ctg tct ctc ctg gtg cag gct gcc gcg ctg gcc gtg gcc ctg gcc     162
Pro Leu Ser Leu Leu Val Gln Ala Ala Ala Leu Ala Val Ala Leu Ala
10              15                  20                  25 cag ggc acc ctg cct gcc ttt ctg ccc tgt gag ctc cag cgc cac ggc     210
Gln Gly Thr Leu Pro Ala Phe Leu Pro Cys Glu Leu Gln Arg His Gly
                30                  35                  40 ctg gtg aat tgc gac tgg ctg ttc ctc aag tcc gtg ccc cac ttc tcg     258
Leu Val Asn Cys Asp Trp Leu Phe Leu Lys Ser Val Pro His Phe Ser
            45                  50                  55 gcg gca gcg ccc cgt ggt aac gtc acc agc ctt tcc ctg tac tcc aac     306
Ala Ala Ala Pro Arg Gly Asn Val Thr Ser Leu Ser Leu Tyr Ser Asn
        60                  65                  70 cgc atc cac cac ctc cac gac tcc gac ttt gtc cac ctg tcc agc ctg     354
Arg Ile His His Leu His Asp Ser Asp Phe Val His Leu Ser Ser Leu
    75                  80                  85 cgg cgt ctc aac ctc aaa tgg aac tgc cca ccc gcc agc ctc agc ccc     402
Arg Arg Leu Asn Leu Lys Trp Asn Cys Pro Pro Ala Ser Leu Ser Pro
```

```
                    90                  95                  100                 105
atg cac ttc ccc tgt cac atg acc att gag ccc cac acc ttc ctg gcc        450
Met His Phe Pro Cys His Met Thr Ile Glu Pro His Thr Phe Leu Ala
                110                 115                 120 gtg ccc acc ctg gag gag ctg aac ctg agc tac aac agc atc acg aca        498
Val Pro Thr Leu Glu Glu Leu Asn Leu Ser Tyr Asn Ser Ile Thr Thr
            125                 130                 135 gta ccc gcc ctg ccc agt tcc ctc gtg tcc ctg tcc ttg agc cgt acc        546
Val Pro Ala Leu Pro Ser Ser Leu Val Ser Leu Ser Leu Ser Arg Thr
        140                 145                 150 aac atc ctg gtg ctg gac cct gcc aac ctc gca ggg ctg cac tcc ctg        594
Asn Ile Leu Val Leu Asp Pro Ala Asn Leu Ala Gly Leu His Ser Leu
    155                 160                 165 cgc ttt ctg ttc ctg gat ggc aac tgc tac tat aag aac ccc tgc ccg        642
Arg Phe Leu Phe Leu Asp Gly Asn Cys Tyr Tyr Lys Asn Pro Cys Pro
170                 175                 180                 185 cag gcc ctg cag gtg gcc ccg ggc gcc ctc ctt ggc ctg ggc aac ctt        690
Gln Ala Leu Gln Val Ala Pro Gly Ala Leu Leu Gly Leu Gly Asn Leu
                190                 195                 200 acg cac ctg tca ctc aag tac aac aac ctc act gcg gtg ccc cgc ggc        738
Thr His Leu Ser Leu Lys Tyr Asn Asn Leu Thr Ala Val Pro Arg Gly
            205                 210                 215 ctg ccc ccc agc ctg gag tac ctg cta ttg tcc tac aac cac atc atc        786
Leu Pro Pro Ser Leu Glu Tyr Leu Leu Leu Ser Tyr Asn His Ile Ile
        220                 225                 230 acc ctg gca cct gag gac ctg gcc aac ctg acc gcc ctg cgt gtg ctc        834
Thr Leu Ala Pro Glu Asp Leu Ala Asn Leu Thr Ala Leu Arg Val Leu
    235                 240                 245 gat gtg ggt gga aac tgc cgt cgc tgt gac cac gcc cgc aac ccc tgt        882
Asp Val Gly Gly Asn Cys Arg Arg Cys Asp His Ala Arg Asn Pro Cys
250                 255                 260                 265 atg gag tgc ccc aag ggc ttc ccg cac ctg cac cct gac acc ttc agc        930
Met Glu Cys Pro Lys Gly Phe Pro His Leu His Pro Asp Thr Phe Ser
                270                 275                 280 cac ctg aac cac ctc gaa ggc ctg gtg ttg aag gac agc tct ctc tac        978
His Leu Asn His Leu Glu Gly Leu Val Leu Lys Asp Ser Ser Leu Tyr
            285                 290                 295 aac ctg aac ccc aga tgg ttc cat gcc ctg ggc aac ctc atg gtg ctg       1026
Asn Leu Asn Pro Arg Trp Phe His Ala Leu Gly Asn Leu Met Val Leu
        300                 305                 310 gac ctg agt gag aac ttc cta tat gac tgc atc acc aaa acc aca gcc       1074
Asp Leu Ser Glu Asn Phe Leu Tyr Asp Cys Ile Thr Lys Thr Thr Ala
    315                 320                 325 ttc cag ggc ctg gcc cag ctg cgc aga ctc aac ttg tct ttc aat tac       1122
Phe Gln Gly Leu Ala Gln Leu Arg Arg Leu Asn Leu Ser Phe Asn Tyr
330                 335                 340                 345 cac aag aag gtg tcc ttt gcc cac ctg cat ctg gcg ccc tcc ttc ggg       1170
His Lys Lys Val Ser Phe Ala His Leu His Leu Ala Pro Ser Phe Gly
                350                 355                 360 agc ctg ctc tcc ctg cag cag ctg gac atg cat ggc atc ttc ttc cgc       1218
Ser Leu Leu Ser Leu Gln Gln Leu Asp Met His Gly Ile Phe Phe Arg
            365                 370                 375 tcg ctc agc gag acc acg ctc cgg tcg ctg gtc cac ctg ccc atg ctc       1266
Ser Leu Ser Glu Thr Thr Leu Arg Ser Leu Val His Leu Pro Met Leu
        380                 385                 390 cag agt ctg cac ctg cag atg aac ttc atc aat cag gcc cag ctc agc       1314
Gln Ser Leu His Leu Gln Met Asn Phe Ile Asn Gln Ala Gln Leu Ser
    395                 400                 405 atc ttc ggg gcc ttc cct ggc ctg cga tac gtg gac ctg tca gac aac       1362
Ile Phe Gly Ala Phe Pro Gly Leu Arg Tyr Val Asp Leu Ser Asp Asn
```

```
       410                 415                 420                 425
cgc ata agt gga gcc atg gag ctg gcg gct gcc acg ggg gag gtg gat         1410
Arg Ile Ser Gly Ala Met Glu Leu Ala Ala Ala Thr Gly Glu Val Asp
                    430                 435                 440 ggt ggg gag aga gtc cgg ctg cca tct ggg gac cta gct ctg ggc cca         1458
Gly Gly Glu Arg Val Arg Leu Pro Ser Gly Asp Leu Ala Leu Gly Pro
                445                 450                 455 ccg ggc acc cct agc tcc gag ggc ttc atg cca ggc tgc aag acc ctc         1506
Pro Gly Thr Pro Ser Ser Glu Gly Phe Met Pro Gly Cys Lys Thr Leu
            460                 465                 470 aac ttc acc ttg gac ctg tca cgg aac aac cta gtg aca atc cag cca         1554
Asn Phe Thr Leu Asp Leu Ser Arg Asn Asn Leu Val Thr Ile Gln Pro
        475                 480                 485 gag atg ttt gcc cgg ctc tcg cgc ctc cag tgc ctg ctc ctg agc cgc         1602
Glu Met Phe Ala Arg Leu Ser Arg Leu Gln Cys Leu Leu Leu Ser Arg
490                 495                 500                 505 aac agc atc tcg cag gca gtc aac ggc tca caa ttt atg ccg ctg acc         1650
Asn Ser Ile Ser Gln Ala Val Asn Gly Ser Gln Phe Met Pro Leu Thr
                510                 515                 520 agc ctg cag gtg ctg gac ctg tcc cat aac aag ctg gac ctg tac cat         1698
Ser Leu Gln Val Leu Asp Leu Ser His Asn Lys Leu Asp Leu Tyr His
                525                 530                 535 ggg cgc tct ttc acg gag ctg ccg cgg ctg gag gcc ctg gac ctc agc         1746
Gly Arg Ser Phe Thr Glu Leu Pro Arg Leu Glu Ala Leu Asp Leu Ser
            540                 545                 550 tac aac agc cag ccc ttc agc atg cag ggc gtg ggt cac aac ctc agc         1794
Tyr Asn Ser Gln Pro Phe Ser Met Gln Gly Val Gly His Asn Leu Ser
        555                 560                 565 ttt gtg gca cag ctg ccg gcc ctg cgc tat ctc agc ctg gcg cac aac         1842
Phe Val Ala Gln Leu Pro Ala Leu Arg Tyr Leu Ser Leu Ala His Asn
570                 575                 580                 585 gac atc cac agc cgt gtg tcc cag cag ctc tgc agc gcc tcg ctg cgg         1890
Asp Ile His Ser Arg Val Ser Gln Gln Leu Cys Ser Ala Ser Leu Arg
                590                 595                 600 gcc ttg gac ttc agc ggc aat gcc ttg agc cgg atg tgg gcc gag gga         1938
Ala Leu Asp Phe Ser Gly Asn Ala Leu Ser Arg Met Trp Ala Glu Gly
                605                 610                 615 gac ctg tat ctc cnc ttc ttc cga ggc ctg agg agc ctg gtc cgg ttg         1986
Asp Leu Tyr Leu Xaa Phe Phe Arg Gly Leu Arg Ser Leu Val Arg Leu
            620                 625                 630 gat ctg tcc cag aat cgc ctg cat acc ctc ttg cca cgc acc ctg gac         2034
Asp Leu Ser Gln Asn Arg Leu His Thr Leu Leu Pro Arg Thr Leu Asp
        635                 640                 645 aac ctc ccc aag agc ctg cgg ctg ctg cgt ctc cgt gac aat tat ctg         2082
Asn Leu Pro Lys Ser Leu Arg Leu Leu Arg Leu Arg Asp Asn Tyr Leu
650                 655                 660                 665 gct ttc ttc aac tgg agc agc ctg gtc ctc ctc ccc agg ctg gaa gcc         2130
Ala Phe Phe Asn Trp Ser Ser Leu Val Leu Leu Pro Arg Leu Glu Ala
                670                 675                 680 ctg gac ctg gcg gga aac cag ctg aag gcc ctg agc aac ggc agc ttg         2178
Leu Asp Leu Ala Gly Asn Gln Leu Lys Ala Leu Ser Asn Gly Ser Leu
                685                 690                 695 cct aat gga acc cag ctc cag agg ctg gac ctc agc agc aac agt atc         2226
Pro Asn Gly Thr Gln Leu Gln Arg Leu Asp Leu Ser Ser Asn Ser Ile
            700                 705                 710 agc ttc gtg gcc tcc agc ttt ttt gct ctg gcc acc agg ctg cga gag         2274
Ser Phe Val Ala Ser Ser Phe Phe Ala Leu Ala Thr Arg Leu Arg Glu
        715                 720                 725 ctc aac ctc agt gcc aac gcc ctc aag acg gtg gag ccc tcc tgg ttc         2322
Leu Asn Leu Ser Ala Asn Ala Leu Lys Thr Val Glu Pro Ser Trp Phe
```

```
                    730                735                740                745
ggt tct cta gcg ggc acc ctg aaa gtc cta gat gtg act ggc aac ccc           2370
Gly Ser Leu Ala Gly Thr Leu Lys Val Leu Asp Val Thr Gly Asn Pro
                750                755                760 ctg cac tgc gcc tgc ggg gcg gcc ttc gtg gac ttc ttg ctg gag gtg           2418
Leu His Cys Ala Cys Gly Ala Ala Phe Val Asp Phe Leu Leu Glu Val
                765                770                775 cag gct gca gtg ccc ggc ctg cca ggc cac gtc aag tgt ggc agt cca           2466
Gln Ala Ala Val Pro Gly Leu Pro Gly His Val Lys Cys Gly Ser Pro
                780                785                790 ggt cag ctc cag ggc cgc agc atc ttt gcg cag gat ctg cgc ctc tgc           2514
Gly Gln Leu Gln Gly Arg Ser Ile Phe Ala Gln Asp Leu Arg Leu Cys
            795                800                805 ctg gat gag gcc ctc tcc tgg gac tgt ttt ggc ctc tcg ctg ctg acc           2562
Leu Asp Glu Ala Leu Ser Trp Asp Cys Phe Gly Leu Ser Leu Leu Thr
810                815                820                825 gtg gcc ctg ggc ctg gcc gtg ccc atg ctg cac cac ctc tgt ggc tgg           2610
Val Ala Leu Gly Leu Ala Val Pro Met Leu His His Leu Cys Gly Trp
                830                835                840 gac ctc tgg tac tgc ttc cac ctg tgc ctg gcc tgg ctg ccc cgg cgg           2658
Asp Leu Trp Tyr Cys Phe His Leu Cys Leu Ala Trp Leu Pro Arg Arg
                845                850                855 ggg cgg cgg cgg ggc gcg gat gcc ctg ccc tac gat gcc ttt gtg gtc           2706
Gly Arg Arg Arg Gly Ala Asp Ala Leu Pro Tyr Asp Ala Phe Val Val
                860                865                870 ttc gac aag gca cag agc gcg gtg gcc gac tgg gtg tac aac gag ctg           2754
Phe Asp Lys Ala Gln Ser Ala Val Ala Asp Trp Val Tyr Asn Glu Leu
                875                880                885 cgg gta cgg cta gag gag cgc cgt gga cgc cga gcg ctc cgc ctg tgc           2802
Arg Val Arg Leu Glu Glu Arg Arg Gly Arg Arg Ala Leu Arg Leu Cys
890                895                900                905 ctg gag gaa cgt gac tgg cta ccc ggt aaa acg ctc ttt gag aac ctg           2850
Leu Glu Glu Arg Asp Trp Leu Pro Gly Lys Thr Leu Phe Glu Asn Leu
                910                915                920 tgg gcc tca gtt tac agc agc cgc aag atg ctg ttt gtg ctg gcc cac           2898
Trp Ala Ser Val Tyr Ser Ser Arg Lys Met Leu Phe Val Leu Ala His
                925                930                935 aca gac agg gtc agc ggc ctc ttg cgc gcc agc ttt ctg ctg gcc cag           2946
Thr Asp Arg Val Ser Gly Leu Leu Arg Ala Ser Phe Leu Leu Ala Gln
                940                945                950 cag cgc ctg ctg gag gac cgc aag gac gtt gtg gtg ctg gtg atc ctg           2994
Gln Arg Leu Leu Glu Asp Arg Lys Asp Val Val Val Leu Val Ile Leu
            955                960                965 cgc ccc gac gcc cac cgc tcc cgc tat gtg cgg ctg cgc cag cgc ctc           3042
Arg Pro Asp Ala His Arg Ser Arg Tyr Val Arg Leu Arg Gln Arg Leu
970                975                980                985 tgc cgc cag agc gtc ctc ctc tgg ccc cac cag ccc agt ggc cag  cgc          3090
Cys Arg Gln Ser Val Leu Leu Trp Pro His Gln Pro Ser Gly Gln  Arg
                990                995                1000 agc ttc tgg gcc  cag ctg ggc acg gcc  ctg acc agg gac aac  cag            3135
Ser Phe Trp Ala  Gln Leu Gly Thr Ala  Leu Thr Arg Asp Asn  Gln
                1005               1010               1015 cac ttc tat aac  cag aac ttc tgc cgg  ggc ccc acg acg gca  gag            3180
His Phe Tyr Asn  Gln Asn Phe Cys Arg  Gly Pro Thr Thr Ala  Glu
                1020               1025               1030 tga ccgcccagca ccccaagcct cctacacctt gcctgtctgc ctgggatgcc                3233
gggcctgctg gccctgcaac accactgctc tgcctcccca actcccaccc ctggcatata         3293
gcagatgctc aataaatgct actagtaggc tgaacggct                                3332
```

```
<210> SEQ ID NO 8
<211> LENGTH: 1031
<212> TYPE: PRT
<213> ORGANISM: Felis Catus
<220> FEATURE:
<221> NAME/KEY: misc_feature
<222> LOCATION: (622)..(622)
<223> OTHER INFORMATION: The 'Xaa' at location 622 stands for His,
      Arg, Pro, or Leu.

<400> SEQUENCE: 8

Met Gly Pro Cys His Gly Ala Leu His Pro Leu Ser Leu Leu Val Gln
1               5                   10                  15

Ala Ala Ala Leu Ala Val Ala Leu Ala Gln Gly Thr Leu Pro Ala Phe
            20                  25                  30

Leu Pro Cys Glu Leu Gln Arg His Gly Leu Val Asn Cys Asp Trp Leu
        35                  40                  45

Phe Leu Lys Ser Val Pro His Phe Ser Ala Ala Pro Arg Gly Asn
    50                  55                  60

Val Thr Ser Leu Ser Leu Tyr Ser Asn Arg Ile His His Leu His Asp
65                  70                  75                  80

Ser Asp Phe Val His Leu Ser Ser Leu Arg Arg Leu Asn Leu Lys Trp
                85                  90                  95

Asn Cys Pro Pro Ala Ser Leu Ser Pro Met His Phe Pro Cys His Met
            100                 105                 110

Thr Ile Glu Pro His Thr Phe Leu Ala Val Pro Thr Leu Glu Glu Leu
        115                 120                 125

Asn Leu Ser Tyr Asn Ser Ile Thr Thr Val Pro Ala Leu Pro Ser Ser
    130                 135                 140

Leu Val Ser Leu Ser Leu Ser Arg Thr Asn Ile Leu Val Leu Asp Pro
145                 150                 155                 160

Ala Asn Leu Ala Gly Leu His Ser Leu Arg Phe Leu Phe Leu Asp Gly
                165                 170                 175

Asn Cys Tyr Tyr Lys Asn Pro Cys Pro Gln Ala Leu Gln Val Ala Pro
            180                 185                 190

Gly Ala Leu Leu Gly Leu Gly Asn Leu Thr His Leu Ser Leu Lys Tyr
        195                 200                 205

Asn Asn Leu Thr Ala Val Pro Arg Gly Leu Pro Pro Ser Leu Glu Tyr
    210                 215                 220

Leu Leu Leu Ser Tyr Asn His Ile Ile Thr Leu Ala Pro Glu Asp Leu
225                 230                 235                 240

Ala Asn Leu Thr Ala Leu Arg Val Leu Asp Val Gly Gly Asn Cys Arg
                245                 250                 255

Arg Cys Asp His Ala Arg Asn Pro Cys Met Glu Cys Pro Lys Gly Phe
            260                 265                 270

Pro His Leu His Pro Asp Thr Phe Ser His Leu Asn His Leu Glu Gly
        275                 280                 285

Leu Val Leu Lys Asp Ser Ser Leu Tyr Asn Leu Asn Pro Arg Trp Phe
    290                 295                 300

His Ala Leu Gly Asn Leu Met Val Leu Asp Leu Ser Glu Asn Phe Leu
305                 310                 315                 320

Tyr Asp Cys Ile Thr Lys Thr Thr Ala Phe Gln Gly Leu Ala Gln Leu
                325                 330                 335

Arg Arg Leu Asn Leu Ser Phe Asn Tyr His Lys Lys Val Ser Phe Ala
            340                 345                 350

His Leu His Leu Ala Pro Ser Phe Gly Ser Leu Leu Ser Leu Gln Gln
```

```
                355                 360                 365
Leu Asp Met His Gly Ile Phe Phe Arg Ser Leu Ser Glu Thr Thr Leu
370                 375                 380

Arg Ser Leu Val His Leu Pro Met Leu Gln Ser Leu His Leu Gln Met
385                 390                 395                 400

Asn Phe Ile Asn Gln Ala Gln Leu Ser Ile Phe Gly Ala Phe Pro Gly
                405                 410                 415

Leu Arg Tyr Val Asp Leu Ser Asp Asn Arg Ile Ser Gly Ala Met Glu
                420                 425                 430

Leu Ala Ala Ala Thr Gly Glu Val Asp Gly Gly Glu Arg Val Arg Leu
                435                 440                 445

Pro Ser Gly Asp Leu Ala Leu Gly Pro Pro Gly Thr Pro Ser Ser Glu
450                 455                 460

Gly Phe Met Pro Gly Cys Lys Thr Leu Asn Phe Thr Leu Asp Leu Ser
465                 470                 475                 480

Arg Asn Asn Leu Val Thr Ile Gln Pro Glu Met Phe Ala Arg Leu Ser
                485                 490                 495

Arg Leu Gln Cys Leu Leu Leu Ser Arg Asn Ser Ile Ser Gln Ala Val
                500                 505                 510

Asn Gly Ser Gln Phe Met Pro Leu Thr Ser Leu Gln Val Leu Asp Leu
                515                 520                 525

Ser His Asn Lys Leu Asp Leu Tyr His Gly Arg Ser Phe Thr Glu Leu
                530                 535                 540

Pro Arg Leu Glu Ala Leu Asp Leu Ser Tyr Asn Ser Gln Pro Phe Ser
545                 550                 555                 560

Met Gln Gly Val Gly His Asn Leu Ser Phe Val Ala Gln Leu Pro Ala
                565                 570                 575

Leu Arg Tyr Leu Ser Leu Ala His Asn Asp Ile His Ser Arg Val Ser
                580                 585                 590

Gln Gln Leu Cys Ser Ala Ser Leu Arg Ala Leu Asp Phe Ser Gly Asn
                595                 600                 605

Ala Leu Ser Arg Met Trp Ala Glu Gly Asp Leu Tyr Leu Xaa Phe Phe
                610                 615                 620

Arg Gly Leu Arg Ser Leu Val Arg Leu Asp Leu Ser Gln Asn Arg Leu
625                 630                 635                 640

His Thr Leu Leu Pro Arg Thr Leu Asp Asn Leu Pro Lys Ser Leu Arg
                645                 650                 655

Leu Leu Arg Leu Arg Asp Asn Tyr Leu Ala Phe Phe Asn Trp Ser Ser
                660                 665                 670

Leu Val Leu Leu Pro Arg Leu Glu Ala Leu Asp Leu Ala Gly Asn Gln
                675                 680                 685

Leu Lys Ala Leu Ser Asn Gly Ser Leu Pro Asn Gly Thr Gln Leu Gln
                690                 695                 700

Arg Leu Asp Leu Ser Ser Asn Ser Ile Ser Phe Val Ala Ser Ser Phe
705                 710                 715                 720

Phe Ala Leu Ala Thr Arg Leu Arg Glu Leu Asn Leu Ser Ala Asn Ala
                725                 730                 735

Leu Lys Thr Val Glu Pro Ser Trp Phe Gly Ser Leu Ala Gly Thr Leu
                740                 745                 750

Lys Val Leu Asp Val Thr Gly Asn Pro Leu His Cys Ala Cys Gly Ala
                755                 760                 765

Ala Phe Val Asp Phe Leu Leu Glu Val Gln Ala Ala Val Pro Gly Leu
                770                 775                 780
```

```
Pro Gly His Val Lys Cys Gly Ser Pro Gly Gln Leu Gln Gly Arg Ser
785                 790                 795                 800

Ile Phe Ala Gln Asp Leu Arg Leu Cys Leu Asp Glu Ala Leu Ser Trp
                805                 810                 815

Asp Cys Phe Gly Leu Ser Leu Leu Thr Val Ala Leu Gly Leu Ala Val
                820                 825                 830

Pro Met Leu His His Leu Cys Gly Trp Asp Leu Trp Tyr Cys Phe His
                835                 840                 845

Leu Cys Leu Ala Trp Leu Pro Arg Arg Gly Arg Arg Gly Ala Asp
        850                 855                 860

Ala Leu Pro Tyr Asp Ala Phe Val Val Phe Asp Lys Ala Gln Ser Ala
865                 870                 875                 880

Val Ala Asp Trp Val Tyr Asn Glu Leu Arg Val Arg Leu Glu Glu Arg
                885                 890                 895

Arg Gly Arg Arg Ala Leu Arg Leu Cys Leu Glu Glu Arg Asp Trp Leu
                900                 905                 910

Pro Gly Lys Thr Leu Phe Glu Asn Leu Trp Ala Ser Val Tyr Ser Ser
                915                 920                 925

Arg Lys Met Leu Phe Val Leu Ala His Thr Asp Arg Val Ser Gly Leu
                930                 935                 940

Leu Arg Ala Ser Phe Leu Leu Ala Gln Gln Arg Leu Leu Glu Asp Arg
945                 950                 955                 960

Lys Asp Val Val Val Leu Val Ile Leu Arg Pro Asp Ala His Arg Ser
                965                 970                 975

Arg Tyr Val Arg Leu Arg Gln Arg Leu Cys Arg Gln Ser Val Leu Leu
                980                 985                 990

Trp Pro His Gln Pro Ser Gly Gln Arg Ser Phe Trp Ala Gln Leu Gly
                995                 1000                1005

Thr Ala Leu Thr Arg Asp Asn Gln His Phe Tyr Asn Gln Asn Phe
        1010                1015                1020

Cys Arg Gly Pro Thr Thr Ala Glu
        1025                1030

<210> SEQ ID NO 9
<211> LENGTH: 24
<212> TYPE: DNA
<213> ORGANISM: Artificial
<220> FEATURE:
<223> OTHER INFORMATION: An artificially synthesized primer sequence

<400> SEQUENCE: 9
tcgtcgtttt gtcgttttgt cgtt                                          24

<210> SEQ ID NO 10
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 10
tccatgacgt tcctgacgtt                                               20

<210> SEQ ID NO 11
<211> LENGTH: 20
<212> TYPE: DNA
<213> ORGANISM: Artificial
<220> FEATURE:
<223> OTHER INFORMATION: An artificially synthesized primer sequence
```

```
<400> SEQUENCE: 11
agactggtta cctggcaaga                                          20

<210> SEQ ID NO 12
<211> LENGTH: 18
<212> TYPE: DNA
<213> ORGANISM: Artificial
<220> FEATURE:
<223> OTHER INFORMATION: An artificially synthesized primer sequence

<400> SEQUENCE: 12
gctattcdgc dgtdggac                                            18

<210> SEQ ID NO 13
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 13
caacctgaaa gtcctagacg                                          20

<210> SEQ ID NO 14
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 14
ggcagaagtt ccggttatag                                          20

<210> SEQ ID NO 15
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 15
agctacaaca gccagcccTT                                          20

<210> SEQ ID NO 16
<211> LENGTH: 19
<212> TYPE: DNA
<213> ORGANISM: Artificial
<220> FEATURE:
<223> OTHER INFORMATION: An artificially synthesized primer sequence

<400> SEQUENCE: 16
aggcgcagtg cagagggtt                                           19

<210> SEQ ID NO 17
<211> LENGTH: 19
<212> TYPE: DNA
<213> ORGANISM: Artificial
<220> FEATURE:
<223> OTHER INFORMATION: An artificially synthesized primer sequence

<400> SEQUENCE: 17
ctgcgcaagc tcaacctgt                                           19

<210> SEQ ID NO 18
<211> LENGTH: 20
<212> TYPE: DNA
```

```
<213> ORGANISM: Artificial
<220> FEATURE:
<223> OTHER INFORMATION: An artificially synthesized primer sequence

<400> SEQUENCE: 18
aagggctggc tgttgtagct                                              20

<210> SEQ ID NO 19
<211> LENGTH: 19
<212> TYPE: DNA
<213> ORGANISM: Artificial
<220> FEATURE:
<223> OTHER INFORMATION: An artificially synthesized primer sequence

<400> SEQUENCE: 19
ctgccttcct accctgtga                                               19

<210> SEQ ID NO 20
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 20
gtggtaattg aaggacaggt t                                            21

<210> SEQ ID NO 21
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 21
gcagttccac ttgaggttga                                              20

<210> SEQ ID NO 22
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 22
acgaagtcag agtcgtgcaa                                              20

<210> SEQ ID NO 23
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 23
aggaagagcc agttgcagtt                                              20

<210> SEQ ID NO 24
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 24
ctgaaagtcc tagacgtgag                                              20
```

```
<210> SEQ ID NO 25
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 25
tcttgccagg taaccagtct                                                    20

<210> SEQ ID NO 26
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 26
ggacctctgg tactgcttcc a                                                  21

<210> SEQ ID NO 27
<211> LENGTH: 22
<212> TYPE: DNA
<213> ORGANISM: Artificial
<220> FEATURE:
<223> OTHER INFORMATION: An artificially synthesized primer sequence

<400> SEQUENCE: 27
aagctcgttg tacacccagt ct                                                 22

<210> SEQ ID NO 28
<211> LENGTH: 19
<212> TYPE: DNA
<213> ORGANISM: Artificial
<220> FEATURE:
<223> OTHER INFORMATION: An artificially synthesized primer sequence

<400> SEQUENCE: 28
gaaggtgaag gtcggagtc                                                     19

<210> SEQ ID NO 29
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 29
gaagatggtg atgggatttc                                                    20

<210> SEQ ID NO 30
<211> LENGTH: 19
<212> TYPE: DNA
<213> ORGANISM: Artificial
<220> FEATURE:
<223> OTHER INFORMATION: An artificially synthesized primer sequence

<400> SEQUENCE: 30
gtggaactgt tttggcatc                                                     19

<210> SEQ ID NO 31
<211> LENGTH: 20
<212> TYPE: DNA
<213> ORGANISM: Artificial
<220> FEATURE:
<223> OTHER INFORMATION: An artificially synthesized primer sequence
```

```
<400> SEQUENCE: 31
cacagcactc tgagctttgt                                              20

<210> SEQ ID NO 32
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 32
tggcattgtc atggactctg                                              20

<210> SEQ ID NO 33
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 33
aggggcgatg atcttgatct                                              20
```